(12) United States Patent
Scharenberg et al.

(10) Patent No.: US 10,378,026 B2
(45) Date of Patent: Aug. 13, 2019

(54) RNA BASED METHOD TO OBTAIN STABLY INTEGRATED RETROVIRAL VECTORS

(71) Applicant: CELLECTIS, Paris (FR)

(72) Inventors: Andrew Scharenberg, Seattle, WA (US); Julianne Smith, Le Plessis-Robinson (FR); Roman Galetto, Paris (FR)

(73) Assignee: CELLECTIS, Paris (FR)

( * ) Notice: Subject to any disclaimer, the term of this patent is extended or adjusted under 35 U.S.C. 154(b) by 207 days.

(21) Appl. No.: 14/915,434

(22) PCT Filed: Sep. 2, 2014

(86) PCT No.: PCT/EP2014/068606
§ 371 (c)(1),
(2) Date: Feb. 29, 2016

(87) PCT Pub. No.: WO2015/028683
PCT Pub. Date: Mar. 5, 2015

(65) Prior Publication Data
US 2016/0222410 A1 Aug. 4, 2016

(30) Foreign Application Priority Data

Sep. 2, 2013 (DK) .................... 2013 70492

(51) Int. Cl.
*C12N 15/86* (2006.01)
*C12N 7/00* (2006.01)

(52) U.S. Cl.
CPC .............. *C12N 15/86* (2013.01); *C12N 7/00* (2013.01); *C12N 2740/17043* (2013.01); *C12N 2740/17052* (2013.01)

(58) Field of Classification Search
CPC .................. C12N 15/86; C12N 7/00; C12N 2740/17043; C12N 2740/17052
See application file for complete search history.

(56) References Cited

U.S. PATENT DOCUMENTS

2012/0141440 A1* 6/2012 Rethwilm .............. C12N 15/86
424/93.21

FOREIGN PATENT DOCUMENTS

| WO | 38/13511 A1 | 4/1998 | |
|---|---|---|---|
| WO | 00/36130 A1 | 6/2000 | |
| WO | WO-0036130 A1 * | 6/2000 | .......... C07K 14/005 |
| WO | 02/079482 A2 | 10/2002 | |
| WO | 2010/111608 A1 | 9/2010 | |
| WO | 2012/152632 A1 | 11/2012 | |

OTHER PUBLICATIONS

Heinkelein et al.; Retrotransposition and Cell-to-Cell Transfer of Foamy Viruses; Journal of Virology, vol. 77, No. 21; Nov. 2003, p. 11855-11858 (Year: 2003).*
WO 00/36130 translation, pp. 1-5, accessed Jun. 23, 2018; http://translationportal.epo.org/emtp/translate/?ACTION= description-retrieval&COUNTRY=WO&ENGINE=google&FORMAT=docdb &KIND=A1&LOCALE=en_EP&NUMBER=0036130&OPS=ops.epo.org%2F3.2&SRCLANG=de&apikey= TSMqTfrVAvNtryGL8QLfbozj8D (Year: 2018).*
Lindemann Dirk et al: "Foamy virus biology and its application for vector development", Viruses, MDPI, CH, Vol. 3, No. 5, May 2011, pp. 561-585.
Rethwilm Axel: "Foamy virus vectors: an awaited alternative to gammaretro- and lentiviral vectors", Current Gene Therapy, Bentham Science Publishers Ltd, NL, vol. 7, No. 4, Aug. 2007, pp. 261-271.
BLA Magnus et al: "Enhanced gene expression from retroviral vectors", BMC Biotechnology, Biomed Central Ltd. London, GB, vol. 8, No. 1, Feb. 25, 2008, p. 19.
Heinkelein et al: "Retrotransposition and Cell-to-Cell Transfer of Foamy Viruses", Journal of Virology, vol. 77, No. 21, Oct. 13, 2003, pp. 11855-11858.
European Patent Office, International Search Report, PCT/EP2014/68606, dated Sep. 2, 2014.
European Patent Office, Written Opinion PCT/EP2014/68606, dated Sep. 2, 2014.

\* cited by examiner

*Primary Examiner* — Antonio Galisteo Gonzalez
(74) *Attorney, Agent, or Firm* — Arrigo, Lee, Guttman & Mouta-Bellum LLP

(57) ABSTRACT

The present invention relates to viral transformation method, particularly foamy virus-mediated transformation method. The present invention relates to the transfer of transgene into cells by the safe and efficient transfer of RNA encoding foamy components. The present invention has therefore therapeutic interest, especially in the field of gene therapy.

Figure 1:
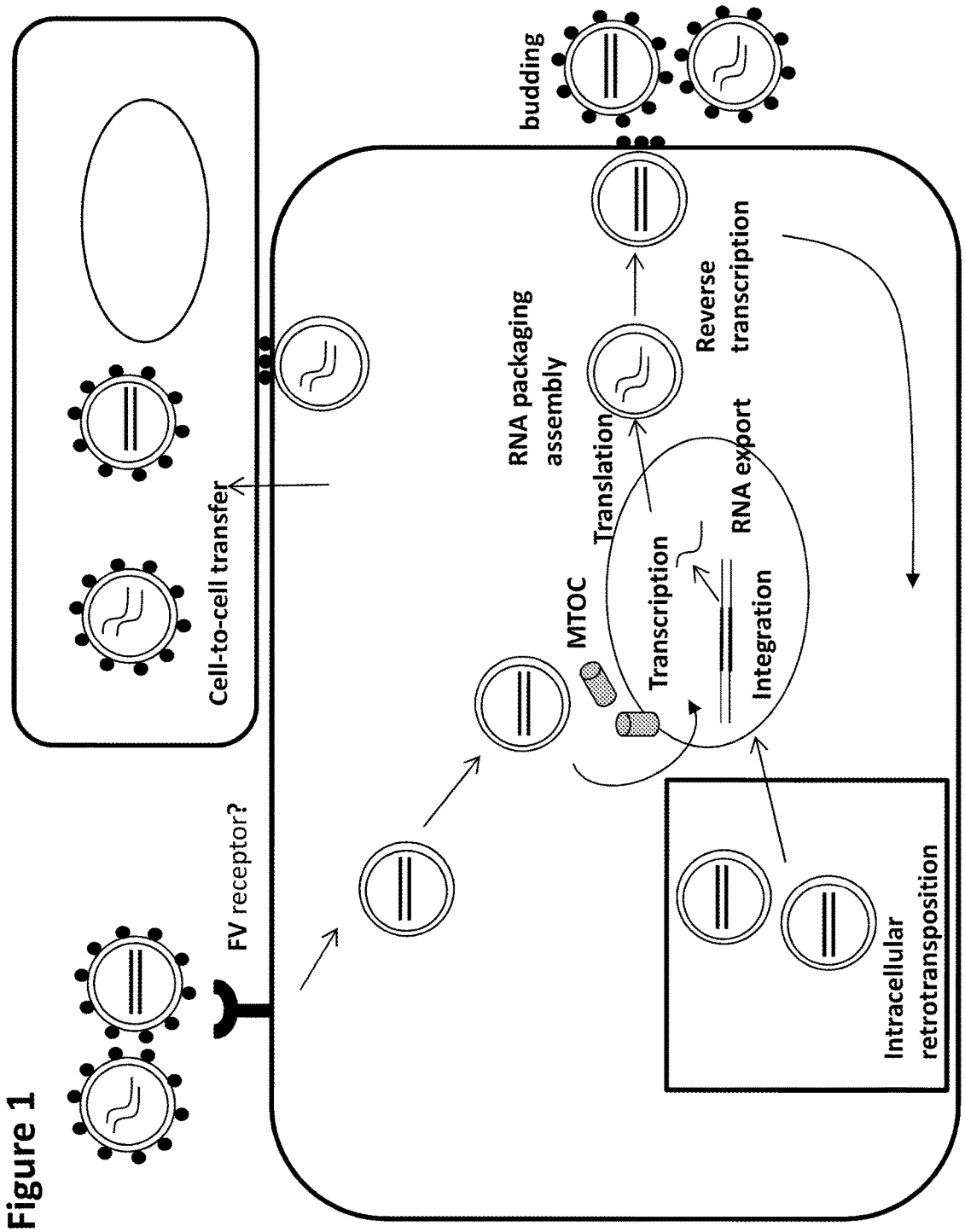

11 Claims, 3 Drawing Sheets
Specification includes a Sequence Listing.

SEQUENCE LISTING

<160> NUMBER OF SEQ ID NOS: 46

<210> SEQ ID NO 1
<211> LENGTH: 1955
<212> TYPE: DNA
<213> ORGANISM: artificial sequence
<220> FEATURE:
<223> OTHER INFORMATION: Description of artificial sequence: Synthetic polynucleotide
<220> FEATURE:
<223> OTHER INFORMATION: FV_Gag_HCO_Seq

<400> SEQUENCE: 1

```
ccatggccag cggcagcaac gtggaggaat acgagctgga cgtggaggcc ctggtggtga      60
tcctgcggga ccggaacatc ccccggaacc ccctgcacgg cgaggtgatc ggcctgcggc     120
tgaccgaggg gtggtgggc cagatcgagc ggttccagat ggtgcggctg atcctgcagg     180
acgacgacaa cgagcccctg cagcggccca gatacgaggt gatccagagg gccgtgaacc     240
cccacaccat gttcatgatc agcggccctc tggccgagct gcagctggcc ttccaggacc     300
tggacctgcc cgagggcccc ctgagattcg cccccctggc caacggccac tacgtgcagg     360
gcgaccccta cagcagcagc taccggcccg tgactatggc cgagaccgcc cagatgaccc     420
gggacgagct ggaagatgtg ctgaacaccc agagcgagat cgagatccag atgatcaacc     480
tgctggaact gtacgaggtg gagaccaggg ccctgcggag gcagctggcc gagcggagca     540
gcacaggcca gggcggcatc agccctggcg cccctagaag cagacccccc gtgagcagct     600
tcagcggcct gcccagcctg cctagcatcc ccggcatcca ccccagagcc cccagccccc     660
ccagagccac ctccaccccc ggcaacatcc cttggagcct gggcgacgac aaccccccct     720
ccagcagctt ccctggcccc agccagccca gagtgagctt ccaccccggc aatcccttcg     780
tggaggaaga gggccaccgg cccagaagcc agagccggga gcggcggaga gagatcctgc     840
ctgcccccgt gcctagcgcc cctcccatga tccagtacat cccccgtgccc cctcccccctc     900 ccatcggcac cgtgatcccc atccagcaca tcagaagcgt gaccggcgag cccccccagaa     960 accccagaga gatccccatc tggctgggcc ggaacgcccc agccatcgac ggcgtgttcc    1020
ccgtgaccac ccccgacctg cggtgccgga tcatcaacgc catcctgggc ggcaacatcg    1080
gcctgagcct gaccccctggc gactgcctga cctgggacag cgccgtggcc accctgttca    1140
tccggaccca cggcaccttc cccatgcacc agctgggcaa cgtgatcaag ggcatcgtgg    1200
accaggaagg cgtcgccacc gcctacaccc tgggcatgat gctgtccggc cagaactacc    1260
agctggtgtc cggcatcatc cggggctacc tgcccggaca ggccgtggtg accgccctgc    1320
agcagcggct ggatcaggaa atcgacgacc agaccagagc cgagccttc atccagcacc    1380 tgaacgccgt gtacgagatc ctgggcctga atgccagggg ccagagcatc cgggccgcg    1440 tgacccccca gcccaggccc agccggggca gaggcagagg ccagaacacc tcccggccca    1500
gccagggacc cgccaacagc ggcagaggcc ggcagagacc cgccagcggc cagtccaacc    1560
ggggcagcag cacccagaac cagaaccagg acaacctgaa ccagggcggc tacaacctgc    1620
ggcccaggac ctaccagccc cagagatatg cggcggacg gggcaggcgg tggaacgaca    1680
acaccaacaa ccaggaaagc cggcccagcg accagggcag ccagaccccc aggcccaacc    1740
aggccggctc cggcgtgagg ggcaaccaga gccagacacc ccggcctgcc gccggaagag    1800
```

```
gcggcagggg caatcacaac cggaaccaga gaagcagcgg agccggcgac agcagagccg   1860
tgaacaccgt gacccagagc gccacctcca gcaccgatga aagcagcagc gccgtgaccg   1920
ccgcctctgg cggcgaccag cgggactgac tcgag                              1955
```

<210> SEQ ID NO 2
<211> LENGTH: 1947
<212> TYPE: RNA
<213> ORGANISM: artificial sequence
<220> FEATURE:
<223> OTHER INFORMATION: Description of artificial sequence: Synthetic
      polynucleotide
<220> FEATURE:
<223> OTHER INFORMATION: FV_Gag_HCO_Seq

<400> SEQUENCE: 2

```
auggccagcg gcagcaacgu ggaggaauac gagcuggacg uggaggcccu ggugugauc     60 cugcgggacc ggaacauccc ccggaacccc cugcacggcg aggugaucgg ccugcggcug   120
accgaggggu gguggggcca gaucgagcgg uuccagaugg ugcggcugau ccugcaggac   180
gacgacaacg agcccuugca gcggcccaga uacgagguga ccagagggc cgugaacccc    240 cacaccaugu ucaugaucag cggcccucug gccgagcugc agcuggccuu ccaggaccug   300
gaccugcccg agggccccccu gagauucggc ccccuggcca acggccacua cgugcagggc   360
gaccccuaca gcagcagcua ccggcccgug acuauggccg agaccgccca gaugacccgg   420
gacgagcugg aagaugugcu gaacacccag agcgagaucg agauccagau gaucaaccug   480
cuggaacugu acgagguggga ccagggcc cucggaggc agcuggccga gcggagcagc     540
acaggccagg gcggcaucag cccuggcgcc ccuagaagca gaccccccgu gagcagcuuc   600
agcggccugc ccagccugcc uagcauccc ggcauccacc ccagagcccc cagcccccccc   660 agagccaccu ccaccccccgg caacauccu uggagccugg gcgacgacaa ccccccccucc   720 agcagcuucc cuggccccag ccagcccaga gugagcuucc accccggcaa ucccuucgug   780
gaggaagagg ccaccggcc cagaagccag agccgggagc ggcggagaga gauccugccu    840
gcccccgugc cuagcgcccc ucccaugauc caguacauc ccgugcccccc ucccccuccc   900 aucggcaccg ugauccccau ccagcacauc agaagcguga ccggcgagcc cccccagaaac   960 cccagagaga uccccaucug gcugggccgg aacgcccag ccaucgacgg cguguuccc    1020 gugaccaccc ccgaccugcg gugccggauc aucaacgcca uccugggcgg caacaucggc   1080
cugagccuga ccccuggcga cugccugacc ugggacagcg ccguggccac ccuguucauc   1140
cggacccacg gcaccuuccc caugcaccag cugggcaacg ugaucaaggg caucguggac   1200
caggaaggcg ucgccaccgc cuacacccug ggcaugaugc uguccggcca gaacuaccag   1260
cugguguccg gcaucauccg gggcuaccug cccggacagg ccguggugac cgcccugcag   1320
cagcggcugg aucaggaaau cgacgaccag accagagccg agaccuucau ccagcaccug   1380
aacgccgugu acgagauccu gggccugaau ccaggggcc agagcauccg gccagcgug    1440 acccccaagc ccaggcccag ccggggcaga ggcagaggcc agaacaccuc ccggcccagc   1500
cagggacccg ccaacagcgg cagaggccgg cagagacccg ccagcggcca guccaaccgg   1560
ggcagcagca cccagaacca gaaccaggac aaccugaacc agggcggcua caaccugcgg   1620
cccaggaccu accagcccca gagauauggc ggcggacggg caggcgguug aacgacaac     1680 accaacaacc aggaaagccg gcccagcgac cagggcagcc agaccccccag gcccaaccag   1740 gccggcuccg gcgugagggg caaccagagc cagacacccc ggccugccgc cggaagaggc   1800
```

-continued

```
ggcagggca aucacaaccg gaaccagaga agcagcggag ccggcgacag cagagccgug    1860
aacaccguga cccagagcgc caccuccagc accgaugaaa gcagcagcgc cgugaccgcc    1920
gccucuggcg gcgaccagcg ggacuga                                        1947
```

<210> SEQ ID NO 3
<211> LENGTH: 648
<212> TYPE: PRT
<213> ORGANISM: artificial sequence
<220> FEATURE:
<223> OTHER INFORMATION: Description of artificial sequence: Synthetic
      polypeptide
<220> FEATURE:
<223> OTHER INFORMATION: Gag_engineered sequence

<400> SEQUENCE: 3

```
Met Ala Ser Gly Ser Asn Val Glu Glu Tyr Glu Leu Asp Val Glu Ala
1               5                   10                  15

Leu Val Val Ile Leu Arg Asp Arg Asn Ile Pro Arg Asn Pro Leu His
            20                  25                  30

Gly Glu Val Ile Gly Leu Arg Leu Thr Glu Gly Trp Trp Gly Gln Ile
        35                  40                  45

Glu Arg Phe Gln Met Val Arg Leu Ile Leu Gln Asp Asp Asn Glu
    50                  55                  60

Pro Leu Gln Arg Pro Arg Tyr Glu Val Ile Gln Arg Ala Val Asn Pro
65                  70                  75                  80

His Thr Met Phe Met Ile Ser Gly Pro Leu Ala Glu Leu Gln Leu Ala
                85                  90                  95

Phe Gln Asp Leu Asp Leu Pro Glu Gly Pro Leu Arg Phe Gly Pro Leu
            100                 105                 110

Ala Asn Gly His Tyr Val Gln Gly Asp Pro Tyr Ser Ser Ser Tyr Arg
        115                 120                 125

Pro Val Thr Met Ala Glu Thr Ala Gln Met Thr Arg Asp Glu Leu Glu
    130                 135                 140

Asp Val Leu Asn Thr Gln Ser Glu Ile Glu Ile Gln Met Ile Asn Leu
145                 150                 155                 160

Leu Glu Leu Tyr Glu Val Glu Thr Arg Ala Leu Arg Arg Gln Leu Ala
                165                 170                 175

Glu Arg Ser Ser Thr Gly Gln Gly Gly Ile Ser Pro Gly Ala Pro Arg
            180                 185                 190

Ser Arg Pro Pro Val Ser Ser Phe Ser Gly Leu Pro Ser Leu Pro Ser
        195                 200                 205

Ile Pro Gly Ile His Pro Arg Ala Pro Ser Pro Pro Arg Ala Thr Ser
    210                 215                 220

Thr Pro Gly Asn Ile Pro Trp Ser Leu Gly Asp Asp Asn Pro Ser
225                 230                 235                 240

Ser Ser Phe Pro Gly Pro Ser Gln Pro Arg Val Ser Phe His Pro Gly
                245                 250                 255

Asn Pro Phe Val Glu Glu Gly His Arg Pro Arg Ser Gln Ser Arg
            260                 265                 270

Glu Arg Arg Arg Glu Ile Leu Pro Ala Pro Val Pro Ser Ala Pro Pro
        275                 280                 285

Met Ile Gln Tyr Ile Pro Val Pro Pro Pro Ile Gly Thr Val
    290                 295                 300

Ile Pro Ile Gln His Ile Arg Ser Val Thr Gly Glu Pro Pro Arg Asn
305                 310                 315                 320
```

```
Pro Arg Glu Ile Pro Ile Trp Leu Gly Arg Asn Ala Pro Ile Asp
            325                 330                 335

Gly Val Phe Pro Val Thr Thr Pro Asp Leu Arg Cys Arg Ile Ile Asn
        340                 345                 350

Ala Ile Leu Gly Gly Asn Ile Gly Leu Ser Leu Thr Pro Gly Asp Cys
            355                 360                 365

Leu Thr Trp Asp Ser Ala Val Ala Thr Leu Phe Ile Arg Thr His Gly
        370                 375                 380

Thr Phe Pro Met His Gln Leu Gly Asn Val Ile Lys Gly Ile Val Asp
385                 390                 395                 400

Gln Glu Gly Val Ala Thr Ala Tyr Thr Leu Gly Met Met Leu Ser Gly
                405                 410                 415

Gln Asn Tyr Gln Leu Val Ser Gly Ile Ile Arg Gly Tyr Leu Pro Gly
            420                 425                 430

Gln Ala Val Val Thr Ala Leu Gln Gln Arg Leu Asp Gln Glu Ile Asp
        435                 440                 445

Asp Gln Thr Arg Ala Glu Thr Phe Ile Gln His Leu Asn Ala Val Tyr
    450                 455                 460

Glu Ile Leu Gly Leu Asn Ala Arg Gly Gln Ser Ile Arg Ala Ser Val
465                 470                 475                 480

Thr Pro Gln Pro Arg Pro Ser Arg Gly Arg Gly Arg Gly Gln Asn Thr
                485                 490                 495

Ser Arg Pro Ser Gln Gly Pro Ala Asn Ser Gly Arg Gly Arg Gln Arg
            500                 505                 510

Pro Ala Ser Gly Gln Ser Asn Arg Gly Ser Ser Thr Gln Asn Gln Asn
        515                 520                 525

Gln Asp Asn Leu Asn Gly Gly Tyr Asn Leu Arg Pro Arg Thr Tyr
    530                 535                 540

Gln Pro Gln Arg Tyr Gly Gly Arg Gly Arg Arg Trp Asn Asp Asn
545                 550                 555                 560

Thr Asn Asn Gln Glu Ser Arg Pro Ser Asp Gln Gly Ser Gln Thr Pro
                565                 570                 575

Arg Pro Asn Gln Ala Gly Ser Gly Val Arg Gly Asn Gln Ser Gln Thr
            580                 585                 590

Pro Arg Pro Ala Ala Gly Arg Gly Gly Arg Gly Asn His Asn Arg Asn
        595                 600                 605

Gln Arg Ser Ser Gly Ala Gly Asp Ser Arg Ala Val Asn Thr Val Thr
    610                 615                 620

Gln Ser Ala Thr Ser Ser Thr Asp Glu Ser Ser Ala Val Thr Ala
625                 630                 635                 640

Ala Ser Gly Gly Asp Gln Arg Asp
                645

<210> SEQ ID NO 4
<211> LENGTH: 648
<212> TYPE: PRT
<213> ORGANISM: Human foamy virus
<220> FEATURE:
<223> OTHER INFORMATION: Gag (Genbank: CAA68996.1)

<400> SEQUENCE: 4

Met Ala Ser Gly Ser Asn Val Glu Glu Tyr Glu Leu Asp Val Glu Ala
1               5                   10                  15

Leu Val Val Ile Leu Arg Asp Arg Asn Ile Pro Arg Asn Pro Leu His
                20                  25                  30
```

-continued

```
Gly Glu Val Ile Gly Leu Arg Leu Thr Glu Gly Trp Trp Gly Gln Ile
         35                  40                  45

Glu Arg Phe Gln Met Val Arg Leu Ile Leu Gln Asp Asp Asn Glu
 50                  55                  60

Pro Leu Gln Arg Pro Arg Tyr Glu Val Ile Gln Arg Ala Val Asn Pro
 65                  70                  75                  80

His Thr Met Phe Met Ile Ser Gly Pro Leu Ala Glu Leu Gln Leu Ala
                 85                  90                  95

Phe Gln Asp Leu Asp Leu Pro Glu Gly Pro Leu Arg Phe Gly Pro Leu
             100                 105                 110

Ala Asn Gly His Tyr Val Gln Gly Asp Pro Tyr Ser Ser Ser Tyr Arg
             115                 120                 125

Pro Val Thr Met Ala Glu Thr Ala Gln Met Thr Arg Asp Glu Leu Glu
 130                 135                 140

Asp Val Leu Asn Thr Gln Ser Glu Ile Glu Ile Gln Met Ile Asn Leu
145                 150                 155                 160

Leu Glu Leu Tyr Glu Val Gly Thr Arg Ala Leu Arg Arg Gln Leu Ala
                165                 170                 175

Glu Arg Ser Ser Thr Gly Gln Gly Ile Ser Pro Gly Ala Pro Arg
             180                 185                 190

Ser Arg Pro Pro Val Ser Ser Phe Ser Gly Leu Pro Ser Leu Pro Ser
             195                 200                 205

Ile Pro Gly Ile His Pro Arg Ala Pro Ser Pro Pro Arg Ala Thr Ser
 210                 215                 220

Thr Pro Gly Asn Ile Pro Trp Ser Leu Gly Asp Asp Ser Pro Pro Ser
225                 230                 235                 240

Ser Ser Phe Pro Gly Pro Ser Gln Pro Arg Val Ser Phe His Pro Gly
                245                 250                 255

Asn Pro Phe Val Glu Glu Gly His Arg Pro Arg Ser Gln Ser Arg
             260                 265                 270

Glu Arg Arg Arg Glu Ile Leu Pro Ala Pro Val Pro Ser Ala Pro Pro
             275                 280                 285

Met Ile Gln Tyr Ile Pro Val Pro Pro Pro Ile Gly Thr Val
             290                 295                 300

Ile Pro Ile Gln His Ile Arg Ser Val Thr Gly Glu Pro Pro Arg Asn
305                 310                 315                 320

Pro Arg Glu Ile Pro Ile Trp Leu Gly Arg Asn Ala Pro Ala Ile Asp
                325                 330                 335

Gly Val Phe Pro Val Thr Thr Pro Asp Leu Arg Cys Arg Ile Ile Asn
             340                 345                 350

Ala Ile Leu Gly Gly Asn Ile Gly Leu Ser Leu Thr Pro Gly Asp Cys
             355                 360                 365

Leu Thr Trp Asp Ser Ala Val Ala Thr Leu Phe Ile Arg Thr His Gly
 370                 375                 380

Thr Phe Pro Met His Gln Leu Gly Asn Val Ile Lys Gly Ile Val Asp
385                 390                 395                 400

Gln Glu Gly Val Ala Thr Ala Tyr Thr Leu Gly Met Met Leu Ser Gly
                405                 410                 415

Gln Asn Tyr Gln Leu Val Ser Gly Ile Ile Arg Gly Tyr Leu Pro Gly
             420                 425                 430

Gln Ala Val Val Thr Ala Leu Gln Gln Arg Leu Asp Gln Glu Ile Asp
             435                 440                 445
```

Asp Gln Thr Arg Ala Glu Thr Phe Ile Gln His Leu Asn Ala Val Tyr
    450                 455                 460

Glu Ile Leu Gly Leu Asn Ala Arg Gly Gln Ser Ile Arg Ala Ser Val
465                 470                 475                 480

Thr Pro Gln Pro Arg Pro Ser Arg Gly Arg Gly Arg Gly Gln Asn Thr
                485                 490                 495

Ser Arg Pro Ser Gln Gly Pro Ala Asn Ser Gly Arg Gly Arg Gln Arg
            500                 505                 510

Pro Ala Ser Gly Gln Ser Asn Arg Gly Ser Ser Thr Gln Asn Gln Asn
                515                 520                 525

Gln Asp Asn Leu Asn Gln Gly Gly Tyr Asn Leu Arg Pro Arg Thr Tyr
530                 535                 540

Gln Pro Gln Arg Tyr Gly Gly Arg Gly Arg Arg Trp Asn Asp Asn
545                 550                 555                 560

Thr Asn Asn Gln Glu Ser Arg Pro Ser Asp Gln Gly Ser Gln Thr Pro
                565                 570                 575

Arg Pro Asn Gln Ala Gly Ser Gly Val Arg Gly Asn Gln Ser Gln Thr
                580                 585                 590

Pro Arg Pro Ala Ala Gly Arg Gly Gly Arg Gly Asn His Asn Arg Asn
                595                 600                 605

Gln Arg Ser Ser Gly Ala Gly Asp Ser Arg Ala Val Asn Thr Val Thr
610                 615                 620

Gln Ser Ala Thr Ser Ser Thr Asp Glu Ser Ser Ser Ala Val Thr Ala
625                 630                 635                 640

Ala Ser Gly Gly Asp Gln Arg Asp
                645

<210> SEQ ID NO 5
<211> LENGTH: 617
<212> TYPE: PRT
<213> ORGANISM: Macaque simian foamy virus
<220> FEATURE:
<223> OTHER INFORMATION: Gag (Accession number: YP_001961121.1)

<400> SEQUENCE: 5

Met Ala Ala Ile Glu Gly Asp Leu Asp Val Gln Ala Leu Ala Asn Leu
1               5                   10                  15

Phe Asn Asp Leu Gly Ile Asn Arg Asn Pro Arg His Arg Glu Val Ile
                20                  25                  30

Ala Leu Arg Met Thr Gly Gly Trp Trp Gly Pro Ala Thr Arg Tyr Asn
            35                  40                  45

Leu Val Ser Leu Leu Leu Gln Asp Gln Gly Gln Pro Leu Pro Gln
    50                  55                  60

Pro Arg Trp Arg Ala Glu Gly Arg Ala Ala Asn Pro Ala Val Met Phe
65                  70                  75                  80

Thr Leu Glu Ala Pro Trp Gln Asp Leu Arg Leu Ala Phe Asp Asn Ile
                85                  90                  95

Asp Val Gly Glu Gly Thr Leu Arg Phe Gly Pro Leu Ala Asn Gly Asn
            100                 105                 110

Tyr Ile Pro Gly Asp Glu Phe Ser Leu Glu Phe Leu Pro Pro Ala Met
        115                 120                 125

Gln Glu Ile Thr Gln Met Gln Arg Asp Glu Leu Glu Glu Val Leu Asp
    130                 135                 140

Val Val Gly Gln Ile Thr Met Gln Met Asn Asp Leu Ile Gly Met Gln
145                 150                 155                 160

-continued

Asp Ala Gln Ile Arg Gly Leu Glu Gly Gln Leu Arg Gly Leu Arg Gly
                165                 170                 175

Asn Leu Pro Val Ala Gly Thr Pro Pro Pro Pro Pro Ser Leu Asp
            180                 185                 190

Leu Gln Pro Ala Ala Ser Ser Pro Tyr Val Ala Pro Ala Pro Ser
        195                 200                 205

Ala Pro Asn Pro Phe Leu Pro Gly Pro Ser Asp Gly Ser Gly Ala Ala
    210                 215                 220

Pro Ala Gln Pro Ser Ala Pro Pro Val Ala Ser Pro Leu Pro Ser Leu
225                 230                 235                 240

Leu Pro Ala Gln Pro Met Gln Pro Val Ile Gln Tyr Val His Pro Pro
                245                 250                 255

Pro Ile Asn Pro Ala Gln Gln Val Ile Pro Ile Gln His Ile Arg Ala
                260                 265                 270

Val Thr Gly Asn Ala Pro Ser Asn Pro Arg Glu Ile Pro Met Trp Ile
        275                 280                 285

Gly Arg Asn Ala Ser Ala Ile Glu Gly Val Phe Pro Ile Pro Thr Ser
    290                 295                 300

Asp Ile Arg Ser Arg Val Ile Asn Ala Leu Leu Gly Arg Gln Leu Gly
305                 310                 315                 320

Leu Asn Leu Asp Pro Gln His Cys Ile Thr Trp Ala Ser Ala Ile Ala
                325                 330                 335

Thr Leu Tyr Val Arg Thr His Gly Ser Tyr Pro Leu His Gln Leu Ala
                340                 345                 350

Glu Val Leu Arg Arg Val Ser Asn Ser Glu Gly Ala Ala Ala Ala Trp
        355                 360                 365

Gln Leu Gly Met Met Leu Thr Asn Gln Asp Tyr Asn Leu Val Trp Gly
    370                 375                 380

Met Val Arg Pro Leu Leu Pro Gly Gln Ala Val Val Thr Ala Met Gln
385                 390                 395                 400

His Arg Leu Asp Gln Glu Val Ser Asp Ala Ala Arg Ile Val Ser Phe
                405                 410                 415

Val Asn His Leu Asn Ala Val Tyr Glu Leu Leu Gly Leu Asn Ala Arg
            420                 425                 430

Gly Gln Asn Leu Arg Val Ser Thr Gly Gly Gln Thr Thr Ala Arg Thr
        435                 440                 445

Ser Ala Gly Arg Gly Ala Arg Gly Arg Arg Ser Gln Gln Gly Thr Pro
450                 455                 460

Gly Arg Gln Ser Ser Gly Gln Ala Pro Pro Gln Gly Arg Arg Ser Ser
465                 470                 475                 480

Gln Gly Gln Gln Pro Arg Gln Ser Glu Ser Gly Asp Gln Asn Asn Gln
                485                 490                 495

Arg Gln Leu Gln Gly Gly Asn Asn Arg Gly Gly Tyr Asn Leu Arg Pro
            500                 505                 510

Arg Thr Tyr Gln Pro Gln Arg Tyr Gly Gly Gly Arg Gly Arg Arg Trp
        515                 520                 525

Asn Asp Gln Thr Ala Arg Ala Asp Asn Gln Arg Ser Gln Ser Gln
530                 535                 540

Gln Pro Gln Ser Glu Ala Arg Gly Glu Gln Ser Arg Thr Ser Gly Ala
545                 550                 555                 560

Gly Arg Glu Gln Gly Gly Arg Gly Asn Gln Asn Arg Asn Gln Arg Ser
                565                 570                 575

Ala Gly Glu Asn Thr Asp Arg Ser Val Asn Thr Val Thr Ala Thr Ser

```
                 580                 585                 590
Ala Ser Ile Ser Ala Ser Gly Gln Asn Gly Ser Ser Thr Thr Pro Pro
             595                 600                 605

Ala Ser Gly Ser Gly Asn Gln Gly Asn
         610                 615

<210> SEQ ID NO 6
<211> LENGTH: 643
<212> TYPE: PRT
<213> ORGANISM: African green monkey simian foamy virus
<220> FEATURE:
<223> OTHER INFORMATION: Gag (NCBI reference: YP_001956721.2)

<400> SEQUENCE: 6

Met Gly Asp His Asn Leu Asn Val Gln Glu Leu Leu Asn Leu Phe Gln
1               5                   10                  15

Asn Leu Gly Ile Pro Arg Gln Pro Asn His Arg Glu Val Ile Gly Leu
            20                  25                  30

Arg Met Leu Gly Gly Trp Trp Gly Pro Gly Thr Arg Tyr Ile Leu Val
        35                  40                  45

Ser Ile Phe Leu Gln Asp Asp Ser Gly Gln Pro Leu Gln Gln Pro Arg
    50                  55                  60

Trp Arg Pro Glu Gly Arg Pro Val Asn Pro Leu Val His Asn Thr Ile
65                  70                  75                  80

Glu Ala Pro Trp Gly Glu Leu Arg Gln Ala Phe Glu Asp Leu Asp Val
                85                  90                  95

Ala Glu Gly Thr Leu Arg Phe Gly Pro Leu Ala Asn Gly Asn Trp Ile
            100                 105                 110

Pro Gly Asp Glu Tyr Ser Met Glu Phe Gln Pro Pro Leu Ala Gln Glu
        115                 120                 125

Ile Ala Gln Met Gln Arg Asp Glu Leu Glu Glu Ile Leu Asp Ile Thr
    130                 135                 140

Gly Gln Ile Cys Ala Gln Val Ile Asp Leu Val Asp Met Gln Asp Ala
145                 150                 155                 160

Gln Ile Arg Gly Leu Glu Arg Arg Ile Gln Asp Arg Leu Gly Leu Arg
                165                 170                 175

Asp Asn Leu Pro Val Ala Gly Ile Gln Ala Pro Pro Ser Ser Pro Ile
            180                 185                 190

Gly Gln Pro Ile Ala Ser Ser Ser Leu Gln Pro Ile Pro Gly Ser Ser
        195                 200                 205

Ser Ser Pro Ala Asp Leu Asp Gly Ile Trp Thr Pro Arg Gln Ile Asp
    210                 215                 220

Pro Arg Leu Ser Arg Val Ala Tyr Asn Pro Phe Leu Pro Gly Ser Ser
225                 230                 235                 240

Asp Gly Ser Gly Gly Ser Ile Pro Val Gln Pro Ser Ala Pro Pro Ala
                245                 250                 255

Val Leu Pro Ser Leu Pro Ser Leu Pro Ala Pro Val Ser Gln Pro Ile
            260                 265                 270

Ile Gln Tyr Val Ala Gln Pro Val Pro Ala Pro Gln Ala Ile Pro
        275                 280                 285

Ile Gln His Ile Arg Ala Val Thr Gly Asn Thr Pro Thr Asn Pro Arg
    290                 295                 300

Asp Ile Pro Met Trp Leu Gly Arg His Ser Ala Ala Ile Glu Gly Val
305                 310                 315                 320

Phe Pro Met Thr Thr Pro Asp Leu Arg Cys Arg Val Val Asn Ala Leu
```

325                 330                 335
Ile Gly Gly Ser Leu Gly Leu Ser Leu Glu Pro Ile His Cys Val Asn
                340                 345                 350
Trp Ala Ala Val Val Ala Leu Tyr Val Arg Thr His Gly Ser Tyr
            355                 360                 365
Pro Ile His Glu Leu Ala Asn Val Leu Arg Ala Val Thr Gln Glu
370                 375                 380
Gly Val Ala Thr Gly Phe Gln Leu Gly Ile Met Leu Ser Asn Gln Asp
385                 390                 395                 400
Tyr Asn Leu Val Trp Gly Ile Leu Arg Pro Leu Leu Pro Gln Ala
                405                 410                 415
Val Val Thr Ala Met Gln Gln Arg Leu Asp Gln Glu Val Asn Asp Ala
                420                 425                 430
Ala Arg Ile Thr Ser Phe Asn Gly His Leu Asn Asp Ile Tyr Gln Leu
                435                 440                 445
Leu Gly Leu Asn Ala Arg Gly Gln Ser Ile Ala Arg Ala Gln Ser Ala
            450                 455                 460
Ser Thr Ser Gly Asn Ser Ala Ser Ala Gly Arg Gly Arg Arg Gly Gln
465                 470                 475                 480
Arg Thr Gln Gln Gln Ala Gly Arg Gln Gln Gln Gln Thr Arg Arg
                485                 490                 495
Thr Asn Gln Gly Asn Gly Gln Arg Asp Asn Asn Gln Arg Gln Ser
            500                 505                 510
Ser Gly Gly Asn Gln Gly Gln Arg Gly Gln Gly Gly Tyr Asp Leu Arg
            515                 520                 525
Pro Arg Thr Tyr Gln Pro Gln Arg Tyr Gly Gly Arg Gly Arg Arg
        530                 535                 540
Trp Asn Asp Asn Gln Gln Gln Gln Ala Gln Pro Gly Arg Ser Ser
545                 550                 555                 560
Asp Gln Pro Arg Ser Gln Ser Gln Gln Pro Gln Pro Glu Ala Arg Gly
                565                 570                 575
Asp Gln Ser Arg Thr Ser Gly Ala Gly Arg Gly Gln Gln Gly Arg Gly
                580                 585                 590
Asn Gln Asn Arg Asn Gln Arg Arg Ala Asp Ala Asn Asn Thr Arg Asn
            595                 600                 605
Val Asp Thr Val Thr Ala Thr Thr Thr Ser Ser Ser Thr Ala Ser Ser
                610                 615                 620
Gly Gln Asn Gly Ser Ser Thr Thr Pro Pro Ala Ser Gly Ser Arg Asn
625                 630                 635                 640
Gln Gly Asp

<210> SEQ ID NO 7
<211> LENGTH: 572
<212> TYPE: PRT
<213> ORGANISM: Squirrel monkey foamy virus
<220> FEATURE:
<223> OTHER INFORMATION: Gag (GenBank: ADE05994.1)

<400> SEQUENCE: 7

Met Ala Arg Gly Asn Leu Asp Ile Ala Arg Leu Thr Val Leu Leu Gln
1               5                   10                  15
Glu Asn Ser Leu Ser Gly Asn Pro Pro His Leu Thr His Tyr Val Leu
            20                  25                  30
Arg Met Thr Glu Gly Trp Trp Gly Pro Phe Pro Arg Tyr Thr Arg Val
        35                  40                  45

```
Arg Ile Ile Leu Gln Asp Glu Ser Gly Asn Pro Leu Ser Gln Pro Arg
     50                  55                  60

Trp Glu Leu Val Asp Arg Met Phe Asn Pro Leu Arg Asp Pro Ile Leu
 65                  70                  75                  80

Glu Thr Thr Leu Asp Glu Met Asp Arg Val Phe Asp Gly Ile Asn Leu
                 85                  90                  95

Ser Pro Gly Thr Glu Arg Tyr Gly Pro Leu Cys Asp Gly Asn Phe Leu
            100                 105                 110

Tyr Thr Asp Asp Ala Trp Asn Asp Phe Asn Pro Met Ser Ala Leu Glu
            115                 120                 125

Val Ala Asp Val Glu Leu Thr Pro Ala Leu Tyr Arg Glu His Leu Asn
            130                 135                 140

Phe Leu Ser Arg Val Ala Glu Gly Met Leu Gly Asp Ile Ile Met Leu
145                 150                 155                 160

Lys Gln Glu Asn Glu Asp Ala His Glu Thr Ile Thr Arg Leu Arg Glu
                165                 170                 175

Arg Ile Ile Asn Gln Pro Thr Ser Ala Pro Ile Ile Thr Ser Thr Pro
            180                 185                 190

Gly Gly Val Ser Gly Leu Pro Pro Ser Val Tyr Gln Pro Thr Gly Leu
            195                 200                 205

His Glu Thr Tyr Ile Gln Pro Ser Arg Pro Met Gln Pro Ser Ala Pro
210                 215                 220

Pro Leu Pro Leu Met Gly Asp Leu Gly Ser Gly Ile Leu Ser Val Leu
225                 230                 235                 240

Pro Ile Ser Gln Ile Arg Thr Val Ile Gly Asn Thr Pro Val Asp Pro
            245                 250                 255

Lys Lys Val Pro Leu Trp Ile Ala Lys Ser Ala Ser Ala Ile Glu Gly
            260                 265                 270

Val Met Pro Thr Asn Thr Pro Asp Ile Arg Cys Arg Leu Val Asn Ala
            275                 280                 285

Leu Leu Pro Gln His Gly Gly Leu Ile Leu Gln Pro His Glu Cys Asn
290                 295                 300

Ser Trp Thr Gln Ile Ala Ser Ala Leu Tyr Thr Arg Val Asn Gly Met
305                 310                 315                 320

Ile Pro Leu His Ala Leu Pro Gln Thr Leu Ser Gln Val Thr Lys Glu
            325                 330                 335

Glu Gly Ile Leu Val Ala Tyr Gln Ile Gly Met Thr Phe Thr Gly Gln
            340                 345                 350

Asn Phe Pro Leu Thr Trp Gly Ile Leu Arg Pro Leu Leu Pro Gly Gln
            355                 360                 365

Ala Val Val Ala Met Met Gln Gly Tyr Leu Asp Gln Tyr Pro Thr Asp
            370                 375                 380

Asp Leu Lys Ala Val Asn Phe Ala Ser Ile Leu Arg Arg Val Phe Asp
385                 390                 395                 400

Ile Leu Gly Leu Asn Tyr Met Gly Gln Asn Ile Arg Asn Gln Ser Ser
            405                 410                 415

Pro Ser Leu Thr Val Ser Ser Ala Arg Gly Ala Thr Gly Arg Gly Arg
            420                 425                 430

Gly Arg Ser Arg Asn Ile Gly Arg Gly Arg Gly Thr Thr Pro Asn Phe
            435                 440                 445

Gln Gly Arg Gly Gln Pro Ala Thr Thr Pro Thr Val Thr Thr Ser Gly
            450                 455                 460
```

Ser Thr Ser Ser Thr Thr Glu Ser Gln Gly Arg Asn Ser Asn Pro Asn
465                 470                 475                 480

Tyr Asn Phe Arg Pro Arg Val Asn Gln Pro Pro Arg Tyr Gly Gly Gly
            485                 490                 495

Pro Asn Pro Tyr Arg Asn Arg Glu Pro Leu Asn Asn Pro Pro Asn Arg
            500                 505                 510

Glu Asn Thr Thr Gln Asn Asn Thr Arg Arg Pro Gly Ser Gln Gly Gln
            515                 520                 525

Asn Arg Asn Arg Asn Gln Asn Arg Thr Val Asn Ala Val Gln Val Val
            530                 535                 540

Pro Asn Gln Asp Asn Thr Asn Gln Pro Asn Ile Asn Pro Asn Gln Asn
545                 550                 555                 560

Val Ser Thr Pro Ala Ser Ala Ser Gly Gly Asn Ser
            565                 570

<210> SEQ ID NO 8
<211> LENGTH: 559
<212> TYPE: PRT
<213> ORGANISM: Equine Foamy virus
<220> FEATURE:
<223> OTHER INFORMATION: Gag (NCBI Reference: NP_054715.1)

<400> SEQUENCE: 8

Met Ala Gln Asn Glu Thr Phe Asp Pro Val Ala Leu Gln Gly Tyr Tyr
1               5                   10                  15

Pro Ala Gly Gly Ile Leu Ala Asp Asn Asp Ile Ile Asn Ile Arg Phe
            20                  25                  30

Thr Ser Gly Gln Trp Gly Ile Gly Asp Arg Trp Leu Gln Val Arg Leu
        35                  40                  45

Arg Leu Val Asp Pro Asn Thr Gly Gln Pro Leu Ala Gln Pro Glu Tyr
50                  55                  60

Glu Asp Thr Gly Leu Pro Ala Glu Asn Arg Gly Ile Val Val Ala Val
65                  70                  75                  80

Ser His Asn Ala Ala Arg Asn Ile Phe Asn Asn Val Gln Pro Ala Gly
                85                  90                  95

Gly Pro Asn Arg His Gly Pro Leu His Asp Gly Gln Phe Gln Val Gly
            100                 105                 110

Asp Asp Pro Ser Glu His Phe Val Pro Ile Glu Glu Asn Leu Ile Pro
        115                 120                 125

Gln Glu Ile Val Asn Leu Gly Ala Ala Arg Arg Glu Val Arg Leu Leu
130                 135                 140

Arg Glu Met Cys Val Arg Leu Leu His Val Arg Arg Gln Met Met Gly
145                 150                 155                 160

Met Gly Met Pro Gly Ala Ile Gln Pro Gln Pro Pro Val Gly Pro Leu
                165                 170                 175

Pro Ala Pro Ala Gln Pro Pro Ile Pro Gly Pro Pro Val Pro Pro Pro
            180                 185                 190

Val Pro Pro Pro Ala Pro Pro Ala Pro Val Asn Pro Pro Val Pro Pro
        195                 200                 205

Val Gln Pro Ile His His Leu Pro Ile Thr His Ile Arg Ala Val Ile
    210                 215                 220

Gly Glu Thr Pro Ala Gln Ile Arg Asp Val Pro Leu Trp Leu Ala Gln
225                 230                 235                 240

Ser Ile Pro Ala Leu Thr Gly Val Tyr Pro Ala Met Asp Ala Gly Thr
                245                 250                 255

```
Leu Thr Arg Leu Val Asn Ala Ile Thr Ala Arg His Pro Gly Leu Ala
            260                 265                 270

Leu Gly Met Asn Glu Ala Gly Ser Trp His Glu Ala Val His Leu Ile
        275                 280                 285

Trp Gln Arg Thr Phe Gly Ala Thr Ala Leu His Ala Leu Ser Asp Val
    290                 295                 300

Leu Lys Gly Ile Ala Gln Arg Asn Gly Val Val Met Ala Leu Glu Met
305                 310                 315                 320

Gly Leu Met Phe Thr Asn Asp Asp Trp Asp Leu Thr Trp Ser Val Ile
            325                 330                 335

Arg Arg Cys Leu Pro Gly Gln Ala Ser Val Val Thr Ile Gln Ala Arg
            340                 345                 350

Leu Asp Ala Leu Pro Asn Asn Gln Ala Arg Ile Ile Gln Ala Gly Phe
            355                 360                 365

Ile Ile Arg Glu Val Tyr Glu Val Leu Gly Leu Asp Pro Leu Gly Arg
            370                 375                 380

Pro Leu Asn Phe Pro Gly Gly Leu Thr Gln Arg Asp Thr Ala Val Pro
385                 390                 395                 400

Val Thr Arg Gly Arg Gly Arg Gly Arg Thr Gly Pro Arg Arg Gly Pro
                    405                 410                 415

Val Leu Pro Val Ser Ser Asn Gln Arg Gln Glu Thr Ala Gly Gly
                420                 425                 430

Asn Gln Pro Gln Thr Gln Pro Gln Gln Asn Thr Phe Ser Asn Gln
                435                 440                 445

Thr Asn Gln Arg Gly Asn Gln Arg Gln Trp Gln Asn Arg Gly Thr Asp
    450                 455                 460

Ser Gln Arg Arg Tyr Phe Phe Arg Pro Arg Pro Ser Gln Pro Gln Arg
465                 470                 475                 480

Tyr Gly Ser Asn Gln Gly Pro Asp Asn Pro Asn Pro Tyr Arg Gly Arg
                485                 490                 495

Asp Ser Thr Asn Gln Ser Gly Gln Glu Arg Gln Leu Pro Gln Gln Gln
                500                 505                 510

Gln Gly Ser Arg Arg Gly Pro Gly Arg Asn Thr Asn Ser Gly Asn Asn
            515                 520                 525

Thr Val His Thr Val Arg Gln Val Glu Ser Ser Gln Leu Gln Gln Asn
    530                 535                 540

Ala Ser Pro Thr Ala Ser Pro Ser Thr Asn Gln Gly Gln Gln Pro
545                 550                 555

<210> SEQ ID NO 9
<211> LENGTH: 544
<212> TYPE: PRT
<213> ORGANISM: Bovine Foamy Virus
<220> FEATURE:
<223> OTHER INFORMATION: Gag (GenBank: AFR79238.1)

<400> SEQUENCE: 9

Met Ala Leu Asn Asp Phe Asp Pro Ile Ala Leu Gln Gly Tyr Leu Pro
1               5                   10                  15

Ala Pro Arg Val Leu Gln His Asn Asp Ile Ile Ile Cys Arg Ala Thr
            20                  25                  30

Ser Gly Pro Trp Gly Ile Gly Asp Arg Tyr Asn Leu Ile Arg Ile His
        35                  40                  45

Leu Gln Asp Pro Ala Gly Gln Pro Leu Pro Ile Pro Gln Trp Glu Pro
    50                  55                  60
```

-continued

```
Ile Pro Asn Arg Thr Ala Asn Pro Arg Thr Gln Pro Tyr Pro Val Val
 65                  70                  75                  80

Ser Ala Pro Met Ala Thr Leu Glu Asn Ile Leu Asn Asn Phe His Ile
                 85                  90                  95

Pro His Gly Val Ser Arg Tyr Gly Pro Leu Glu Gly Gly Asp Tyr Gln
            100                 105                 110

Pro Gly Glu Gln Tyr Ser Gln Gly Phe Cys Pro Val Thr Gln Ala Glu
        115                 120                 125

Ile Ala Leu Leu Asn Gly Gln His Leu Glu Glu Ile Thr Ile Leu
    130                 135                 140

Arg Glu Ile Thr His Arg Leu Met Gln Gly Val Arg Pro Pro Ala Ala
145                 150                 155                 160

Pro Gln Gly Pro Ala Pro Pro Pro Ala Gln Pro Pro Ala Pro
                165                 170                 175

Leu Pro Ala Pro Pro Ile Gly Pro Pro Pro Ala Val Pro Ala Pro
                180                 185                 190

Ala Pro Gly Pro Met Pro Val Pro Gln His Leu Pro Ile Thr His Ile
            195                 200                 205

Arg Ala Val Ile Gly Glu Thr Pro Ala Asn Ile Arg Glu Val Pro Leu
    210                 215                 220

Trp Leu Ala Arg Ala Val Pro Ala Leu Gln Gly Val Tyr Pro Val Gln
225                 230                 235                 240

Asp Ala Val Met Arg Ser Arg Thr Val Asn Ala Leu Thr Val Arg His
                245                 250                 255

Pro Gly Leu Ala Leu Glu Pro Leu Glu Cys Gly Ser Trp Gln Glu Cys
            260                 265                 270

Leu Ala Ala Leu Trp Gln Arg Thr Phe Gly Ala Thr Ala Leu His Ala
        275                 280                 285

Leu Gly Asp Thr Leu Gly Gln Ile Ala Asn Ser Asp Gly Ile Val Met
    290                 295                 300

Ala Ile Glu Leu Gly Leu Leu Phe Ser Asp Asp Asn Trp Asp Leu Val
305                 310                 315                 320

Trp Gly Ile Cys Arg Arg Phe Leu Pro Gly Gln Ala Val Cys Val Ala
                325                 330                 335

Val Gln Ala Arg Leu Asp Pro Leu Pro Asp Asn Ala Thr Arg Ile Val
            340                 345                 350

Met Ile Ser His Ile Ile Arg Asp Val Tyr Ala Ile Leu Gly Leu Asp
        355                 360                 365

Pro Leu Gly Arg Pro Met Gln Gln Pro Leu Pro Arg Arg Asn Asn Gln
    370                 375                 380

Pro Pro Arg Gln Gln Pro Gln Arg Arg Gln Pro Arg Arg Thr Gly
385                 390                 395                 400

Asn Gln Glu Glu Arg Gly Gln Arg Asn Arg Gly Arg Gln Asn Ala Gln
                405                 410                 415

Thr Pro Arg Gln Glu Gly Asn Arg Leu Gln Asn Ser Gln Leu Pro Gly
            420                 425                 430

Pro Arg Asp Tyr Pro Asn Asn Ser Asn Gln Pro Arg Tyr Pro Leu Arg
        435                 440                 445

Pro Asn Pro Gln Gln Pro Gln Arg Tyr Gly Gln Glu Asn Arg Gly
    450                 455                 460

Asn Asn Pro Asn Pro Tyr Arg Gln Pro Thr Pro Gly Asn Gly Asn Gln
465                 470                 475                 480

Asn Arg Asn Phe Ser Arg Gly Pro Ala Pro Val Asn Glu Gln Ser Arg
```

```
              485                 490                 495
Gly Arg Gly Arg Ser Ser Gln Gly Thr Asn Asn Thr Gly Ser Ser Ala
            500                 505                 510

Val His Ser Val Arg Leu Thr Ser Ala Ala Pro Pro Ile Pro Pro Gln
            515                 520                 525

Asp Ala Gly Thr Pro Pro Thr Pro Ser Gly Asn Gln Gly Gln Ser Ser
            530                 535                 540

<210> SEQ ID NO 10
<211> LENGTH: 514
<212> TYPE: PRT
<213> ORGANISM: Feline Foamy virus
<220> FEATURE:
<223> OTHER INFORMATION: Gag (GenBank: AGC11907.1)

<400> SEQUENCE: 10

Met Ala Arg Glu Leu Asn Pro Leu Gln Leu Gln Gln Leu Tyr Ile Asn
1               5                   10                  15

Asn Gly Leu Gln Pro Asn Pro Gly His Gly Asp Val Ile Ala Val Arg
            20                  25                  30

Phe Thr Gly Gly Pro Trp Gly Pro Gly Asp Arg Trp Ala Arg Val Ala
        35                  40                  45

Ile Arg Leu Gln Asp Asn Thr Gly Gln Pro Leu Gln Val Pro Gly Tyr
    50                  55                  60

Asp Leu Glu Pro Gly Ile Ile Asn Leu Arg Glu Asp Ile Leu Ile Ala
65                  70                  75                  80

Gly Pro Tyr Asn Leu Ile Arg Thr Ala Phe Leu Asp Leu Glu Pro Ala
                85                  90                  95

Arg Gly Pro Glu Arg His Gly Pro Phe Gly Asp Gly Arg Leu Gln Pro
            100                 105                 110

Gly Asp Gly Leu Ser Glu Gly Phe Gln Pro Ile Thr Asp Glu Glu Met
        115                 120                 125

Gln Thr Glu Val Gly Thr Ile Gly Ala Ala Arg Asn Glu Ile Arg Leu
    130                 135                 140

Leu Arg Glu Ala Leu Gln Arg Leu Gln Val Gly Gly Val Gly Arg Pro
145                 150                 155                 160

Ile Pro Gly Ala Ile Leu Gln Pro Gln Pro Val Ile Gly Ala Val Ile
                165                 170                 175

Pro Ile Asn His Leu Arg Ser Val Ile Gly Asn Thr Pro Pro Asn Pro
            180                 185                 190

Arg Asp Val Ala Leu Trp Leu Gly Arg Ser Thr Ala Ala Ile Glu Gly
        195                 200                 205

Val Phe Pro Ile Val Asp Gln Val Thr Arg Met Arg Val Val Asn Ala
    210                 215                 220

Leu Val Ala Ser His Pro Gly Leu Thr Leu Thr Glu Asn Glu Ala Gly
225                 230                 235                 240

Ser Trp Asn Ala Ala Ile Ser Ala Leu Trp Arg Lys Ala His Gly Ala
                245                 250                 255

Ala Ala Gln His Glu Leu Ala Gly Val Leu Ser Asp Ile Asn Lys Lys
            260                 265                 270

Glu Gly Ile Gln Thr Ala Phe Asn Leu Gly Met Gln Phe Thr Asp Gly
        275                 280                 285

Asn Trp Ser Leu Val Trp Gly Ile Ile Arg Thr Leu Leu Pro Gly Gln
    290                 295                 300

Ala Leu Val Thr Asn Ala Gln Ser Gln Phe Asp Leu Met Gly Asp Asp
```

```
                   305                 310                 315                 320
Ile Gln Arg Ala Glu Asn Phe Pro Arg Val Ile Asn Asn Leu Tyr Thr
                        325                 330                 335

Met Leu Gly Leu Asn Ile His Gly Gln Ser Ile Arg Pro Arg Val Gln
                    340                 345                 350

Thr Gln Pro Gln Gln Ala Arg Ser Arg Asn Gln Gly Arg Ser Gln Gln
                355                 360                 365

Gly Gln Leu Asn Gln Pro Arg Pro Gln Asn Arg Asn Asn Gln Ser Tyr
            370                 375                 380

Arg Pro Pro Arg Gln Gln Gln His Ser Asp Val Pro Glu Gln Arg
385                 390                 395                 400

Asp Gln Arg Gly Pro Ser Gln Pro Pro Arg Gly Ser Gly Gly Tyr
                405                 410                 415

Asn Phe Arg Arg Asn Pro Gln Gln Pro Gln Arg Tyr Gly Gln Gly Pro
                420                 425                 430

Pro Gly Pro Asn Pro Tyr Arg Arg Phe Gly Asp Gly Gly Asn Pro Gln
                435                 440                 445

Gln Gln Gly Pro Pro Pro Asn Arg Gly Pro Asp Gln Gly Pro Arg Pro
            450                 455                 460

Gly Gly Asn Pro Arg Gly Gly Gly Arg Gly Gln Gly Pro Arg Asn Gly
465                 470                 475                 480

Gly Gly Asn Ala Ala Ala Val His Thr Val Lys Ala Ser Glu Asn Glu
                485                 490                 495

Thr Lys Asn Gly Ser Ala Glu Ala Ala Asp Gly Gly Lys Lys Gly Gly
            500                 505                 510

Lys Asp
```

<210> SEQ ID NO 11
<211> LENGTH: 3450
<212> TYPE: DNA
<213> ORGANISM: artificial sequence
<220> FEATURE:
<223> OTHER INFORMATION: Description of artificial sequence: Synthetic polynucleotide
<220> FEATURE:
<223> OTHER INFORMATION: FV_Pol_HCO_Seq

<400> SEQUENCE: 11

```
ccatgggcca ccatgaaccc cctgcagctg ctgcagcccc tgcccgccga gatcaagggc    60
accaagctgc tggcccactg ggacagcggc gccaccatca cctgcatccc cgagagcttt   120
ctggaagatg agcagcccat caagaaaacc ctgatcaaga ccatccacgg cgagaagcag   180
cagaacgtgt actacgtgac cttcaaggtg aaaggccgga aggtggaggc cgaggtgatc   240
gccagcccct acgagtacat cctgctgtcc cccaccgacg tgcccggct gacccagcag   300
cctctgcagc tgaccatcct ggtgcccctg caggaatacc aggaaaagat cctgagcaag   360
accgccctgc cgaggacca gaaacagcag ctgaaaccc tgttcgtgaa gtacgacaac   420
ctgtggcagc actgggagaa ccaggtgggc accggaaga tccggcccca caacatcgcc   480
accggcgact accccccag gccccagaag cagtaccca tcaacccca ggccaagccc   540
agcatccaga tcgtgatcga cgacctgctg aagcagggcg tgctgacccc ccagaacagc   600
accatgaata cccccgtgta ccccgtgccc aagcccgacg gcggtggcg gatggtgctg   660
gactaccggg aggtgaacaa gacaatcccc ctgacagccg cccagaacca gcacagcgcc   720
ggcatcctgg ccaccatcgt gcggcagaag tacaagacca ccctggacct ggccaacggc   780
```

```
ttctgggccc acccctatcac ccccgagtcc tactggctga ccgccttcac atggcagggc    840
aagcagtact gctggacccg gctgccccag ggcttcctga acagccctgc cctgttcacc    900
gccgacgtgg tggatctgct gaaagaaatc cccaacgtgc aggtgtacgt ggacgacatc    960
tacctgagcc acgacgaccc caagaacac gtgcagcagc tggaaaaggt gttccagatc    1020
ctgctgcagg ccggctacgt ggtgtccctg aagaagagcg agatcggcca gaaaaccgtg    1080
gagttcctgg gcttcaacat caccaaagag ggcaggggcc tgaccgacac cttcaagaca    1140
aagctgctga acatcacccc ccccaaggac ctgaagcagc tgcagagcat cctgggcctg    1200
ctgaacttcg cccggaactt catccccaac ttcgccgagc tggtgcagcc tctgtacaac    1260
ctgatcgcct ccgccaaggg caagtacatc gagtggagcg aggaaaacac caagcagctg    1320
aacatggtga tcgaggccct gaacaccgcc agcaacctgg aagagcggct gcccgagcag    1380
cggctggtga tcaaggtgaa caccagcccc agcgccggct atgtgcggta ctacaacgag    1440
accggcaaga acccatcat gtacctgaac tacgtgttca gcaaggccga gctgaagttc    1500
tccatgctgg aaaaactgct gaccaccatg cacaaggccc tgatcaaagc tatggatctg    1560
gctatgggcc aggaaatcct ggtctacagc cccatcgtga gcatgaccaa gatccagaaa    1620
accccctgc tgagcggaa ggccctgccc atccggtgga tcacctggat gacctacctg    1680
gaagatcccc ggatccagtt ccactacgac aagaccctgc cagagctgaa gcacatcccc    1740
gacgtgtaca ccagcagcca gagccccgtg aagcacccca gccagtacga gggcgtgttc    1800
tacaccgacg gcagcgccat caagtccccc gaccccacca agagcaacaa cgccggcatg    1860
ggcatcgtgc acgccaccta caagcccgag taccaggtgc tgaaccagtg gagcatcccc    1920
ctgggcaacc acaccgccca gatggccgag atcgccgccg tggagtttgc ctgcaagaag    1980
gccctgaaga tccctggccc cgtgctggtg attaccgaca gcttctacgt ggccgagagc    2040
gccaacaaag agctgcccta ctggaagagc aacggcttcg tgaacaacaa gaagaagccc    2100
ctgaaacaca tcagcaagtg gaagagcatc gccgagtgcc tgagcatgaa gcccgacatc    2160
accatccagc acgagaaggg gcaccagccc accaacacca gcatccacac cgaaggcaac    2220
gccctggccg acaagctggc cacccagggc tcctacgtgg tgaactgcaa caccaagaag    2280
cccaacctgg acgccgaact ggaccagctg ctgcagggcc actacatcaa gggctacccc    2340
aagcagtaca cctatttct ggaagatggc aaggtgaaag tgtccaggcc cgagggcgtg    2400
aagatcatcc cccctcagag cgaccggcag aaaatcgtgc tgcaggccca aacctggcc    2460
cacaccggca gagaggccac cctgctgaag atcgccaacc tgtactggtg cccaacatg    2520
cggaaggacg tggtgaaaca gctgggccgg tgccagcagt gcctgatcac caacgccagc    2580
aacaaggcca gcggccccat cctgcggccc gacagacccc agaagccctt cgacaagttc    2640
ttcatcgact acatcggccc cctgcccccc agccagggct acctgtacgt gctggtggtg    2700
gtggacggca tgaccggctt cacctggctg taccctacca aggcccccag cacctccgcc    2760
accgtgaaga gcctgaacgt gctgaccagc atcgccatcc ccaaggtgat ccacagcgac    2820
cagggagccg ccttcaccag cagcaccttc gccgagtggg ccaaagagcg ggcatccac    2880
ctggaatttt ccaccccta ccaccccag agcagcggca aggtggagcg gaagaacagc    2940
gacatcaagc ggctgctgac caaactgctg gtgggcaggc ccaccaagtg gtacgatctg    3000
ctgccccgtgg tgcagctggc cctgaataac acctactccc ccgtgctgaa gtacacccct    3060
caccagctgc tgttcggcat cgacagcaac acccccttcg ccaatcagga cacccctggat    3120
ctgacccggg aggaagagct gtctctgctg caggaaatcc ggaccagcct gtaccacccc    3180
```

| | |
|---|---|
| agcacccccc ctgccagcag caggtcctgg tcccccgtgg tgggccagct ggtgcaggaa | 3240 |
| cgggtcgcca ggcccgccag cctgagaccc cggtggcaca agccctccac agtgctgaag | 3300 |
| gtgctgaatc cccggaccgt ggtgatcctg gaccacctgg gcaacaaccg gaccgtgagc | 3360 |
| atcgacaacc tgaagcccac ctcccaccag aacggcacca ccaacgacac cgccactatg | 3420 |
| gaccacctgg aaaagaacga gtgactcgag | 3450 |

<210> SEQ ID NO 12
<211> LENGTH: 3432
<212> TYPE: RNA
<213> ORGANISM: artificial sequence
<220> FEATURE:
<223> OTHER INFORMATION: Description of artificial sequence: Synthetic polynucleotide
<220> FEATURE:
<223> OTHER INFORMATION: FV_Pol_HCO_Seq

<400> SEQUENCE: 12

| | |
|---|---|
| augaaccccc ugcagcugcu gcagcccccug cccgccgaga ucaagggcac caagcugcug | 60 |
| gcccacuggg acagcggcgc caccaucacc ugcauccccg agagcuuucu ggaagaugag | 120 |
| cagcccauca agaaaacccu gaucaagacc auccacggcg agaagcagca gaacguguac | 180 |
| uacgugaccu ucaaggugaa aggccggaag guggaggccg aggugaucgc cagcccuac | 240 |
| gaguacaucc ugcuguccc caccgacgug cccuggcuga cccagcagcc ucugcagcug | 300 |
| accauccugg ugcccugca ggaauaccag gaaaagaucc ugagcaagac cgcccugccc | 360 |
| gaggaccaga acagcagcu gaaaacccug uucgugaagu acgacaaccu gguggcagcac | 420 |
| ugggagaacc agguggccca ccggaagauc cggccccaca acaucgccac cggcgacuac | 480 |
| cccccaggc cccagaagca guaccccauc aaccccaagg ccaagcccag cauccagauc | 540 |
| gugaucgacg accugcugaa gcagggcgug cugaccccc agaacagcac caugaauacc | 600 |
| cccguguacc ccgugcccaa gcccgacggc cggggcgga uggugcugga cuacggggag | 660 |
| gugaacaaga caauccccu gacagccgcc cagaaccagc acagcgccgg cauccuggcc | 720 |
| accaucgugc ggcagaagua caagaccacc cuggaccugg ccaacggcuu cuggccccac | 780 |
| ccuaucaccc ccgagucua cuggcugacc gccuucacau ggcagggcaa gcaguacugc | 840 |
| uggacccggc ugccccaggg cuuccugaac agcccugccc guucaccgc cgacguggug | 900 |
| gaucugcuga agaaauccc caacgugcag guguacgugg acgacaucua ccugagccac | 960 |
| gacgacccca agaacacgu gcagcagcug gaaaaggugu ccagauccu gcugcaggcc | 1020 |
| ggcuacgugg ugucccugaa gagagcgag aucggccaga aaaccguggga uuccugggc | 1080 |
| uucaacauca ccaaagaggg caggggccug accgacaccu ucaagacaaa gcugcugaac | 1140 |
| aucacccccc ccaaggaccu gaagcagcug cagagcaucc uggcugcu gaacuucgcc | 1200 |
| cggaacuuca uccccaacuu cgccgagcug gugcagccuc uguacaaccu gaucgccucc | 1260 |
| gccaagggca guacaucga guggagcgag gaaaacacca agcagcugaa cauggugauc | 1320 |
| gaggcccuga caccgccag caaccuggaa gagcggcugc ccgagcagcg gcuggugauc | 1380 |
| aagguugaaca ccagccccag cgccggcuau gugcgguacu acaacgagac cggcaagaaa | 1440 |
| cccaucaugu accugaacua cguguucagc aaggccgagc ugaaguucuc caugcuggaa | 1500 |
| aaacugcuga ccaccaugca caaggcccug aucaaagcua uggaucggc uaugggccag | 1560 |
| gaaauccugg ucuacagccc caucgugagc augaccaaga uccagaaaac cccccugccu | 1620 |
| gagcggaagg cccugcccau ccgguggauc accuggauga ccuaccugga agaucccgg | 1680 |

```
auccaguucc acuacgacaa gacccugcca gagcugaagc acaucccga cguguacacc      1740 agcagccaga gccccgugaa gcaccccagc caguacgagg gcguguucua caccgacggc      1800
agcgccauca aguccccga ccccaccaag agcaacaacg ccggcauggg caucgugcac      1860
gccaccuaca agcccgagua ccaggugcug aaccagugga gcaucccccu gggcaaccac      1920
accgcccaga uggccgagau cgccgccgug gaguuugccu gcaagaaggc ccugaagauc      1980
ccuggccccg ugcuggugau uaccgacagc uucuacgugg ccgagagcgc caacaaagag      2040
cugcccuacu ggaagagcaa cggcuucgug aacaacaaga gaagcccu gaaacacauc       2100 agcaagugga gagcaucgc cgagugccug agcaugaagc ccgacaucac cauccagcac      2160
gagaaggggc accagcccac caacaccagc auccacaccg aaggcaacgc ccuggccgac      2220
aagcuggcca cccagggcuc cuacguggug aacugcaaca ccaagaagcc caaccuggac      2280
gccgaacugg accagcugcu gcagggccac uacaucaagg cuaccccaa gcaguacacc       2340 uauuuucugg aagauggcaa ggugaaagug uccaggcccg agggcgugaa gaucauccc       2400 ccucagagcg accggcagaa aaucgugcug caggcccaca ccuggccca caccggcaga       2460 gaggccaccc ugcugaagau cgccaaccug uacuggugc caacaugcg gaaggacgug       2520 gugaaacagc ugggccggug ccagcagugc cugaucacca cgccagcaa caaggccagc       2580 ggccccaucc ugcggcccga cagacccag aagcccuucg acaaguucuu caucgacuac       2640
aucggccccc ugcccccag ccagggcuac cuguacgugc uggugguggu ggacggcaug       2700
accggcuuca ccuggcugua cccuaccaag gcccccagca ccuccgccac cgugaagagc      2760
cugaacgugc ugaccagcau cgccaucccc aaggugaucc acagcgacca gggagccgcc      2820
uucaccagca gcaccuucgc cgagugggcc aaagagcggg gcauccaccu ggaauuuucc      2880
acccccuacc accccagag cagcggcaag guggagcgga agaacagcga caucaagcgg      2940
cugcugacca aacugcuggu gggcaggccc accaaguggu acgaucgcu gcccguggug      3000 cagcuggccc ugaauaacac cuacuccccc gugcugaagu acacccccuca ccagcugcug      3060 uucggcaucg acagcaacac ccccuucgcc aaucaggaca cccuggaucu gacccgggag      3120
gaagagcugu cucugcugca ggaaauccgg accagccugu accaccccag cacccccccu      3180
gccagcagca gguccuuguc ccccguggug ggccagcugg ucaggaacg ggucgccagg       3240 cccgccagcc ugagaccccg guggcacaag cccuccacag ugcugaaggu gcugaauccc      3300
cggaccgugg ugauccugga ccaccugggc aacaaccgga ccgugagcau cgacaaccug      3360
aagcccaccu cccaccagaa cggcaccacc acgacaccg ccacuaugga ccaccuggaa      3420
aagaacgagu ga                                                          3432
```

<210> SEQ ID NO 13
<211> LENGTH: 1143
<212> TYPE: PRT
<213> ORGANISM: artificial sequence
<220> FEATURE:
<223> OTHER INFORMATION: Description of artificial sequence: Synthetic polypeptides
<220> FEATURE:
<223> OTHER INFORMATION: FV_Pol_HCO_Seq

<400> SEQUENCE: 13

Met Asn Pro Leu Gln Leu Leu Gln Pro Leu Pro Ala Glu Ile Lys Gly
1               5                   10                  15

Thr Lys Leu Leu Ala His Trp Asp Ser Gly Ala Thr Ile Thr Cys Ile
            20                  25                  30

```
Pro Glu Ser Phe Leu Glu Asp Glu Gln Pro Ile Lys Lys Thr Leu Ile
            35                  40                  45

Lys Thr Ile His Gly Glu Lys Gln Gln Asn Val Tyr Tyr Val Thr Phe
 50                  55                  60

Lys Val Lys Gly Arg Lys Val Glu Ala Glu Val Ile Ala Ser Pro Tyr
 65                  70                  75                  80

Glu Tyr Ile Leu Leu Ser Pro Thr Asp Val Pro Trp Leu Thr Gln Gln
                    85                  90                  95

Pro Leu Gln Leu Thr Ile Leu Val Pro Leu Gln Glu Tyr Gln Glu Lys
                100                 105                 110

Ile Leu Ser Lys Thr Ala Leu Pro Glu Asp Gln Lys Gln Gln Leu Lys
                115                 120                 125

Thr Leu Phe Val Lys Tyr Asp Asn Leu Trp Gln His Trp Glu Asn Gln
130                 135                 140

Val Gly His Arg Lys Ile Arg Pro His Asn Ile Ala Thr Gly Asp Tyr
145                 150                 155                 160

Pro Pro Arg Pro Gln Lys Gln Tyr Pro Ile Asn Pro Lys Ala Lys Pro
                165                 170                 175

Ser Ile Gln Ile Val Ile Asp Asp Leu Leu Lys Gln Gly Val Leu Thr
                180                 185                 190

Pro Gln Asn Ser Thr Met Asn Thr Pro Val Tyr Pro Val Pro Lys Pro
                195                 200                 205

Asp Gly Arg Trp Arg Met Val Leu Asp Tyr Arg Glu Val Asn Lys Thr
210                 215                 220

Ile Pro Leu Thr Ala Ala Gln Asn Gln His Ser Ala Gly Ile Leu Ala
225                 230                 235                 240

Thr Ile Val Arg Gln Lys Tyr Lys Thr Thr Leu Asp Leu Ala Asn Gly
                245                 250                 255

Phe Trp Ala His Pro Ile Thr Pro Glu Ser Tyr Trp Leu Thr Ala Phe
                260                 265                 270

Thr Trp Gln Gly Lys Gln Tyr Cys Trp Thr Arg Leu Pro Gln Gly Phe
                275                 280                 285

Leu Asn Ser Pro Ala Leu Phe Thr Ala Asp Val Val Asp Leu Leu Lys
290                 295                 300

Glu Ile Pro Asn Val Gln Val Tyr Val Asp Asp Ile Tyr Leu Ser His
305                 310                 315                 320

Asp Asp Pro Lys Glu His Val Gln Gln Leu Glu Lys Val Phe Gln Ile
                325                 330                 335

Leu Leu Gln Ala Gly Tyr Val Val Ser Leu Lys Lys Ser Glu Ile Gly
                340                 345                 350

Gln Lys Thr Val Glu Phe Leu Gly Phe Asn Ile Thr Lys Glu Gly Arg
                355                 360                 365

Gly Leu Thr Asp Thr Phe Lys Thr Lys Leu Leu Asn Ile Thr Pro Pro
370                 375                 380

Lys Asp Leu Lys Gln Leu Gln Ser Ile Leu Gly Leu Leu Asn Phe Ala
385                 390                 395                 400

Arg Asn Phe Ile Pro Asn Phe Ala Glu Leu Val Gln Pro Leu Tyr Asn
                405                 410                 415

Leu Ile Ala Ser Ala Lys Gly Lys Tyr Ile Glu Trp Ser Glu Glu Asn
                420                 425                 430

Thr Lys Gln Leu Asn Met Val Ile Glu Ala Leu Asn Thr Ala Ser Asn
                435                 440                 445
```

-continued

Leu Glu Glu Arg Leu Pro Glu Gln Arg Leu Val Ile Lys Val Asn Thr
          450                 455                 460

Ser Pro Ser Ala Gly Tyr Val Arg Tyr Asn Glu Thr Gly Lys Lys
465                 470                 475                 480

Pro Ile Met Tyr Leu Asn Tyr Val Phe Ser Lys Ala Glu Leu Lys Phe
                485                 490                 495

Ser Met Leu Glu Lys Leu Leu Thr Thr Met His Lys Ala Leu Ile Lys
                500                 505                 510

Ala Met Asp Leu Ala Met Gly Gln Glu Ile Leu Val Tyr Ser Pro Ile
            515                 520                 525

Val Ser Met Thr Lys Ile Gln Lys Thr Pro Leu Pro Glu Arg Lys Ala
530                 535                 540

Leu Pro Ile Arg Trp Ile Thr Trp Met Thr Tyr Leu Glu Asp Pro Arg
545                 550                 555                 560

Ile Gln Phe His Tyr Asp Lys Thr Leu Pro Glu Leu Lys His Ile Pro
                565                 570                 575

Asp Val Tyr Thr Ser Ser Gln Ser Pro Val Lys His Pro Ser Gln Tyr
            580                 585                 590

Glu Gly Val Phe Tyr Thr Asp Gly Ser Ala Ile Lys Ser Pro Asp Pro
            595                 600                 605

Thr Lys Ser Asn Asn Ala Gly Met Gly Ile Val His Ala Thr Tyr Lys
610                 615                 620

Pro Glu Tyr Gln Val Leu Asn Gln Trp Ser Ile Pro Leu Gly Asn His
625                 630                 635                 640

Thr Ala Gln Met Ala Glu Ile Ala Ala Val Glu Phe Ala Cys Lys Lys
                645                 650                 655

Ala Leu Lys Ile Pro Gly Pro Val Leu Val Ile Thr Asp Ser Phe Tyr
            660                 665                 670

Val Ala Glu Ser Ala Asn Lys Glu Leu Pro Tyr Trp Lys Ser Asn Gly
            675                 680                 685

Phe Val Asn Asn Lys Lys Lys Pro Leu Lys His Ile Ser Lys Trp Lys
            690                 695                 700

Ser Ile Ala Glu Cys Leu Ser Met Lys Pro Asp Ile Thr Ile Gln His
705                 710                 715                 720

Glu Lys Gly His Gln Pro Thr Asn Thr Ser Ile His Thr Glu Gly Asn
                725                 730                 735

Ala Leu Ala Asp Lys Leu Ala Thr Gln Gly Ser Tyr Val Val Asn Cys
                740                 745                 750

Asn Thr Lys Lys Pro Asn Leu Asp Ala Glu Leu Asp Gln Leu Leu Gln
            755                 760                 765

Gly His Tyr Ile Lys Gly Tyr Pro Lys Gln Tyr Thr Tyr Phe Leu Glu
            770                 775                 780

Asp Gly Lys Val Lys Val Ser Arg Pro Glu Gly Val Lys Ile Ile Pro
785                 790                 795                 800

Pro Gln Ser Asp Arg Gln Lys Ile Val Leu Gln Ala His Asn Leu Ala
                805                 810                 815

His Thr Gly Arg Glu Ala Thr Leu Leu Lys Ile Ala Asn Leu Tyr Trp
                820                 825                 830

Trp Pro Asn Met Arg Lys Asp Val Lys Gln Leu Gly Arg Cys Gln
                835                 840                 845

Gln Cys Leu Ile Thr Asn Ala Ser Asn Lys Ala Ser Gly Pro Ile Leu
850                 855                 860

Arg Pro Asp Arg Pro Gln Lys Pro Phe Asp Lys Phe Phe Ile Asp Tyr

```
                865                 870                 875                 880
Ile Gly Pro Leu Pro Ser Gln Gly Tyr Leu Tyr Val Leu Val Val
                    885                 890                 895

Val Asp Gly Met Thr Gly Phe Thr Trp Leu Tyr Pro Thr Lys Ala Pro
            900                 905                 910

Ser Thr Ser Ala Thr Val Lys Ser Leu Asn Val Leu Thr Ser Ile Ala
        915                 920                 925

Ile Pro Lys Val Ile His Ser Asp Gln Gly Ala Ala Phe Thr Ser Ser
    930                 935                 940

Thr Phe Ala Glu Trp Ala Lys Glu Arg Gly Ile His Leu Glu Phe Ser
945                 950                 955                 960

Thr Pro Tyr His Pro Gln Ser Ser Gly Lys Val Glu Arg Lys Asn Ser
                965                 970                 975

Asp Ile Lys Arg Leu Leu Thr Lys Leu Leu Val Gly Arg Pro Thr Lys
            980                 985                 990

Trp Tyr Asp Leu Leu Pro Val Val Gln Leu Ala Leu Asn Asn Thr Tyr
        995                 1000                1005

Ser Pro Val Leu Lys Tyr Thr Pro His Gln Leu Leu Phe Gly Ile Asp
    1010                1015                1020

Ser Asn Thr Pro Phe Ala Asn Gln Asp Thr Leu Asp Leu Thr Arg Glu
1025                1030                1035                1040

Glu Glu Leu Ser Leu Leu Gln Glu Ile Arg Thr Ser Leu Tyr His Pro
                1045                1050                1055

Ser Thr Pro Pro Ala Ser Ser Arg Ser Trp Ser Pro Val Val Gly Gln
            1060                1065                1070

Leu Val Gln Glu Arg Val Ala Arg Pro Ala Ser Leu Arg Pro Arg Trp
        1075                1080                1085

His Lys Pro Ser Thr Val Leu Lys Val Leu Asn Pro Arg Thr Val Val
    1090                1095                1100

Ile Leu Asp His Leu Gly Asn Asn Arg Thr Val Ser Ile Asp Asn Leu
1105                1110                1115                1120

Lys Pro Thr Ser His Gln Asn Gly Thr Thr Asn Asp Thr Ala Thr Met
                1125                1130                1135

Asp His Leu Glu Lys Asn Glu
            1140

<210> SEQ ID NO 14
<211> LENGTH: 1143
<212> TYPE: PRT
<213> ORGANISM: Human foamy virus
<220> FEATURE:
<223> OTHER INFORMATION: Pol (GenBank: CAA68999.1)

<400> SEQUENCE: 14

Met Asn Pro Leu Gln Leu Leu Gln Pro Leu Pro Ala Glu Ile Lys Gly
1               5                   10                  15

Thr Lys Leu Leu Ala His Trp Asp Ser Gly Ala Thr Ile Thr Cys Ile
            20                  25                  30

Pro Glu Ser Phe Leu Glu Asp Glu Gln Pro Ile Lys Lys Thr Leu Ile
        35                  40                  45

Lys Thr Ile His Gly Glu Lys Gln Gln Asn Val Tyr Tyr Val Thr Phe
    50                  55                  60

Lys Val Lys Gly Arg Lys Val Glu Ala Glu Val Ile Ala Ser Pro Tyr
65                  70                  75                  80

Glu Tyr Ile Leu Leu Ser Pro Thr Asp Val Pro Trp Leu Thr Gln Gln
```

-continued

```
                    85                  90                  95
Pro Leu Gln Leu Thr Ile Leu Val Pro Leu Gln Glu Tyr Gln Glu Lys
                100                 105                 110

Ile Leu Ser Lys Thr Ala Leu Pro Glu Asp Gln Lys Gln Gln Leu Lys
                115                 120                 125

Thr Leu Phe Val Lys Tyr Asp Asn Leu Trp Gln His Trp Glu Asn Gln
                130                 135                 140

Val Gly His Arg Lys Ile Arg Pro His Asn Ile Ala Thr Gly Asp Tyr
145                 150                 155                 160

Pro Pro Arg Pro Gln Lys Gln Tyr Pro Ile Asn Pro Lys Ala Lys Pro
                165                 170                 175

Ser Ile Gln Ile Val Ile Asp Asp Leu Leu Lys Gln Gly Val Leu Thr
                180                 185                 190

Pro Gln Asn Ser Thr Met Asn Thr Pro Val Tyr Pro Val Pro Lys Pro
                195                 200                 205

Asp Gly Arg Trp Arg Met Val Leu Asp Tyr Arg Glu Val Asn Lys Thr
                210                 215                 220

Ile Pro Leu Thr Ala Ala Gln Asn Gln His Ser Ala Gly Ile Leu Ala
225                 230                 235                 240

Thr Ile Val Arg Gln Lys Tyr Lys Thr Thr Leu Asp Leu Ala Asn Gly
                245                 250                 255

Phe Trp Ala His Pro Ile Thr Pro Glu Ser Tyr Trp Leu Thr Ala Phe
                260                 265                 270

Thr Trp Gln Gly Lys Gln Tyr Cys Trp Thr Arg Leu Pro Gln Gly Phe
                275                 280                 285

Leu Asn Ser Pro Ala Leu Phe Thr Ala Asp Val Val Asp Leu Leu Lys
                290                 295                 300

Glu Ile Pro Asn Val Gln Val Tyr Val Asp Asp Ile Tyr Leu Ser His
305                 310                 315                 320

Asp Asp Pro Lys Glu His Val Gln Gln Leu Glu Lys Val Phe Gln Ile
                325                 330                 335

Leu Leu Gln Ala Gly Tyr Val Val Ser Leu Lys Lys Ser Glu Ile Gly
                340                 345                 350

Gln Lys Thr Val Glu Phe Leu Gly Phe Asn Ile Thr Lys Glu Gly Arg
                355                 360                 365

Gly Leu Thr Asp Thr Phe Lys Thr Lys Leu Leu Asn Ile Thr Pro Pro
                370                 375                 380

Lys Asp Leu Lys Gln Leu Gln Ser Ile Leu Gly Leu Leu Asn Phe Ala
385                 390                 395                 400

Arg Asn Phe Ile Pro Asn Phe Ala Glu Leu Val Gln Pro Leu Tyr Asn
                405                 410                 415

Leu Ile Ala Ser Ala Lys Gly Lys Tyr Ile Glu Trp Ser Glu Glu Asn
                420                 425                 430

Thr Lys Gln Leu Asn Met Val Ile Glu Ala Leu Asn Thr Ala Ser Asn
                435                 440                 445

Leu Glu Glu Arg Leu Pro Glu Gln Arg Leu Val Ile Lys Val Asn Thr
                450                 455                 460

Ser Pro Ser Ala Gly Tyr Val Arg Tyr Tyr Asn Glu Thr Gly Lys Lys
465                 470                 475                 480

Pro Ile Met Tyr Leu Asn Tyr Val Phe Ser Lys Ala Glu Leu Lys Phe
                485                 490                 495

Ser Met Leu Glu Lys Leu Leu Thr Thr Met His Lys Ala Leu Ile Lys
                500                 505                 510
```

```
Ala Met Asp Leu Ala Met Gly Gln Glu Ile Leu Val Tyr Ser Pro Ile
        515                 520                 525

Val Ser Met Thr Lys Ile Gln Lys Thr Pro Leu Pro Glu Arg Lys Ala
530                 535                 540

Leu Pro Ile Arg Trp Ile Thr Trp Met Thr Tyr Leu Glu Asp Pro Arg
545                 550                 555                 560

Ile Gln Phe His Tyr Asp Lys Thr Leu Pro Glu Leu Lys His Ile Pro
                565                 570                 575

Asp Val Tyr Thr Ser Ser Gln Ser Pro Val Lys His Pro Ser Gln Tyr
            580                 585                 590

Glu Gly Val Phe Tyr Thr Asp Gly Ser Ala Ile Lys Ser Pro Asp Pro
        595                 600                 605

Thr Lys Ser Asn Asn Ala Gly Met Gly Ile Val His Ala Thr Tyr Lys
    610                 615                 620

Pro Glu Tyr Gln Val Leu Asn Gln Trp Ser Ile Pro Leu Gly Asn His
625                 630                 635                 640

Thr Ala Gln Met Ala Glu Ile Ala Ala Val Glu Phe Ala Cys Lys Lys
                645                 650                 655

Ala Leu Lys Ile Pro Gly Pro Val Leu Val Ile Thr Asp Ser Phe Tyr
            660                 665                 670

Val Ala Glu Ser Ala Asn Lys Glu Leu Pro Tyr Trp Lys Ser Asn Gly
        675                 680                 685

Phe Val Asn Asn Lys Lys Pro Leu Lys His Ile Ser Lys Trp Lys
    690                 695                 700

Ser Ile Ala Glu Cys Leu Ser Met Lys Pro Asp Ile Thr Ile Gln His
705                 710                 715                 720

Glu Lys Gly Ile Ser Leu Gln Ile Pro Val Phe Ile Leu Lys Gly Asn
                725                 730                 735

Ala Leu Ala Asp Lys Leu Ala Thr Gln Gly Ser Tyr Val Val Asn Cys
            740                 745                 750

Asn Thr Lys Lys Pro Asn Leu Asp Ala Glu Leu Asp Gln Leu Leu Gln
        755                 760                 765

Gly His Tyr Ile Lys Gly Tyr Pro Lys Gln Tyr Thr Tyr Phe Leu Glu
    770                 775                 780

Asp Gly Lys Val Lys Val Ser Arg Pro Glu Gly Val Lys Ile Ile Pro
785                 790                 795                 800

Pro Gln Ser Asp Arg Gln Lys Ile Val Leu Gln Ala His Asn Leu Ala
                805                 810                 815

His Thr Gly Arg Glu Ala Thr Leu Leu Lys Ile Ala Asn Leu Tyr Trp
            820                 825                 830

Trp Pro Asn Met Arg Lys Asp Val Val Lys Gln Leu Gly Arg Cys Gln
        835                 840                 845

Gln Cys Leu Ile Thr Asn Ala Ser Asn Lys Ala Ser Gly Pro Ile Leu
    850                 855                 860

Arg Pro Asp Arg Pro Gln Lys Pro Phe Asp Lys Phe Phe Ile Asp Tyr
865                 870                 875                 880

Ile Gly Pro Leu Pro Pro Ser Gln Gly Tyr Leu Tyr Val Leu Val Val
                885                 890                 895

Val Asp Gly Met Thr Gly Phe Thr Trp Leu Tyr Pro Thr Lys Ala Pro
            900                 905                 910

Ser Thr Ser Ala Thr Val Lys Ser Leu Asn Val Leu Thr Ser Ile Ala
        915                 920                 925
```

```
Ile Pro Lys Val Ile His Ser Asp Gln Gly Ala Ala Phe Thr Ser Ser
    930                 935                 940

Thr Phe Ala Glu Trp Ala Lys Glu Arg Gly Ile His Leu Glu Phe Ser
945                 950                 955                 960

Thr Pro Tyr His Pro Gln Ser Gly Ser Lys Val Glu Arg Lys Asn Ser
                965                 970                 975

Asp Ile Lys Arg Leu Leu Thr Lys Leu Leu Val Gly Arg Pro Thr Lys
            980                 985                 990

Trp Tyr Asp Leu Leu Pro Val Val Gln Leu Ala Leu Asn Asn Thr Tyr
        995                 1000                1005

Ser Pro Val Leu Lys Tyr Thr Pro His Gln Leu Leu Phe Gly Ile Asp
    1010                1015                1020

Ser Asn Thr Pro Phe Ala Asn Gln Asp Thr Leu Asp Leu Thr Arg Glu
1025                1030                1035                1040

Glu Glu Leu Ser Leu Leu Gln Glu Ile Arg Thr Ser Leu Tyr His Pro
                1045                1050                1055

Ser Thr Pro Pro Ala Ser Ser Arg Ser Trp Ser Pro Val Val Gly Gln
            1060                1065                1070

Leu Val Gln Glu Arg Val Ala Arg Pro Ala Ser Leu Arg Pro Arg Trp
        1075                1080                1085

His Lys Pro Ser Thr Val Leu Lys Val Leu Asn Pro Arg Thr Val Val
    1090                1095                1100

Ile Leu Asp His Leu Gly Asn Asn Arg Thr Val Ser Ile Asp Asn Leu
1105                1110                1115                1120

Lys Pro Thr Ser His Gln Asn Gly Thr Thr Asn Asp Thr Ala Thr Met
                1125                1130                1135

Asp His Leu Glu Lys Asn Glu
            1140

<210> SEQ ID NO 15
<211> LENGTH: 1156
<212> TYPE: PRT
<213> ORGANISM: Macaque simian foamy virus
<220> FEATURE:
<223> OTHER INFORMATION: Pol (NCBI Reference: YP_001961122.1)

<400> SEQUENCE: 15

Met Asp Leu Leu Lys Pro Leu Thr Val Glu Arg Lys Gly Val Lys Ile
1               5                   10                  15

Lys Gly Tyr Trp Asp Ser Gln Ala Asp Ile Thr Cys Val Pro Lys Asp
            20                  25                  30

Leu Leu Gln Gly Glu Glu Pro Val Arg Gln Gln Asn Val Thr Thr Ile
        35                  40                  45

His Gly Thr Gln Glu Gly Asp Val Tyr Tyr Val Asn Leu Lys Ile Asp
    50                  55                  60

Gly Arg Arg Ile Asn Thr Glu Val Ile Gly Thr Thr Leu Asp Tyr Ala
65                  70                  75                  80

Ile Ile Thr Pro Gly Asp Val Pro Trp Ile Leu Lys Lys Pro Leu Glu
                85                  90                  95

Leu Thr Ile Lys Leu Asp Leu Glu Glu Gln Gln Gly Thr Leu Leu Asn
            100                 105                 110

Asn Ser Ile Leu Ser Lys Lys Gly Lys Glu Glu Leu Lys Gln Leu Phe
        115                 120                 125

Glu Lys Tyr Ser Ala Leu Trp Gln Ser Trp Glu Asn Gln Val Gly His
    130                 135                 140
```

-continued

```
Arg Arg Ile Arg Pro His Lys Ile Ala Thr Gly Thr Val Lys Pro Thr
145                 150                 155                 160

Pro Gln Lys Gln Tyr His Ile Asn Pro Lys Ala Lys Pro Asp Ile Gln
                165                 170                 175

Ile Val Ile Asn Asp Leu Leu Lys Gln Gly Val Leu Ile Gln Lys Glu
            180                 185                 190

Ser Thr Met Asn Thr Pro Val Tyr Pro Val Pro Lys Pro Asn Gly Arg
        195                 200                 205

Trp Arg Met Val Leu Asp Tyr Arg Ala Val Asn Lys Val Thr Pro Leu
    210                 215                 220

Ile Ala Val Gln Asn Gln His Ser Tyr Gly Ile Leu Gly Ser Leu Phe
225                 230                 235                 240

Lys Gly Arg Tyr Lys Thr Thr Ile Asp Leu Ser Asn Gly Phe Trp Ala
                245                 250                 255

His Pro Ile Val Pro Glu Asp Tyr Trp Ile Thr Ala Phe Thr Trp Gln
            260                 265                 270

Gly Lys Gln Tyr Cys Trp Thr Val Leu Pro Gln Gly Phe Leu Asn Ser
        275                 280                 285

Pro Gly Leu Phe Thr Gly Asp Val Val Asp Leu Leu Gln Gly Ile Pro
    290                 295                 300

Asn Val Glu Val Tyr Val Asp Asp Val Tyr Ile Ser His Asp Ser Glu
305                 310                 315                 320

Lys Glu His Leu Glu Tyr Leu Asp Ile Leu Phe Asn Arg Leu Lys Glu
                325                 330                 335

Ala Gly Tyr Ile Ile Ser Leu Lys Lys Ser Asn Ile Ala Asn Ser Ile
            340                 345                 350

Val Asp Phe Leu Gly Phe Gln Ile Thr Asn Glu Gly Arg Gly Leu Thr
        355                 360                 365

Asp Thr Phe Lys Glu Lys Leu Glu Asn Ile Thr Ala Pro Thr Thr Leu
    370                 375                 380

Lys Gln Leu Gln Ser Ile Leu Gly Leu Leu Asn Phe Ala Arg Asn Phe
385                 390                 395                 400

Ile Pro Asp Phe Thr Glu Leu Ile Ala Pro Leu Tyr Ala Leu Ile Pro
                405                 410                 415

Lys Ser Thr Lys Asn Tyr Val Pro Trp Gln Ile Glu His Ser Thr Thr
            420                 425                 430

Leu Glu Thr Leu Ile Thr Lys Leu Asn Gly Ala Glu Tyr Leu Gln Gly
        435                 440                 445

Arg Lys Gly Asp Lys Thr Leu Ile Met Lys Val Asn Ala Ser Tyr Thr
    450                 455                 460

Thr Gly Tyr Ile Arg Tyr Tyr Asn Glu Gly Glu Lys Lys Pro Ile Ser
465                 470                 475                 480

Tyr Val Ser Ile Val Phe Ser Lys Thr Glu Leu Lys Phe Thr Glu Leu
                485                 490                 495

Glu Lys Leu Leu Thr Thr Val His Lys Gly Leu Leu Lys Ala Leu Asp
            500                 505                 510

Leu Ser Met Gly Gln Asn Ile His Val Tyr Ser Pro Ile Val Ser Met
        515                 520                 525

Gln Asn Ile Gln Lys Thr Pro Gln Thr Ala Lys Lys Ala Leu Ala Ser
    530                 535                 540

Arg Trp Leu Ser Trp Leu Ser Tyr Leu Glu Asp Pro Arg Ile Arg Phe
545                 550                 555                 560

Phe Tyr Asp Pro Gln Met Pro Ala Leu Lys Asp Leu Pro Ala Val Asp
```

```
              565                 570                 575
Thr Gly Lys Asp Asn Lys His Pro Ser Asn Phe Gln His Ile Phe
            580                 585                 590

Tyr Thr Asp Gly Ser Ala Ile Thr Ser Pro Thr Lys Glu Gly His Leu
            595                 600                 605

Asn Ala Gly Met Gly Ile Val Tyr Phe Ile Asn Lys Asp Gly Asn Leu
            610                 615                 620

Gln Lys Gln Gln Glu Trp Ser Ile Ser Leu Gly Asn His Thr Ala Gln
625                 630                 635                 640

Phe Ala Glu Ile Ala Ala Phe Glu Phe Ala Leu Lys Lys Cys Leu Pro
                645                 650                 655

Leu Gly Gly Asn Ile Leu Val Val Thr Asp Ser Asn Tyr Val Ala Lys
                660                 665                 670

Ala Tyr Asn Glu Glu Leu Asp Val Trp Ala Ser Asn Gly Phe Val Asn
                675                 680                 685

Asn Arg Lys Lys Pro Leu Lys His Ile Ser Lys Trp Lys Ser Val Ala
            690                 695                 700

Asp Leu Lys Arg Leu Arg Pro Asp Val Val Thr His Glu Pro Gly
705                 710                 715                 720

His Gln Lys Leu Asp Ser Ser Pro His Ala Tyr Gly Asn Asn Leu Ala
                725                 730                 735

Asp Gln Leu Ala Thr Gln Ala Ser Phe Lys Val His Met Thr Lys Asn
            740                 745                 750

Pro Lys Leu Asp Ile Glu Gln Ile Lys Ala Ile Gln Ala Cys Gln Asn
            755                 760                 765

Asn Glu Arg Leu Pro Val Gly Tyr Pro Lys Gln Tyr Thr Tyr Glu Leu
            770                 775                 780

Gln Asn Asn Lys Cys Met Val Leu Arg Lys Asp Gly Trp Arg Glu Ile
785                 790                 795                 800

Pro Pro Ser Arg Glu Arg Tyr Lys Leu Ile Lys Glu Ala His Asn Ile
                805                 810                 815

Ser His Ala Gly Arg Glu Ala Val Leu Leu Lys Ile Gln Glu Asn Tyr
            820                 825                 830

Trp Trp Pro Lys Met Lys Lys Asp Ile Ser Ser Phe Leu Ser Thr Cys
            835                 840                 845

Asn Val Cys Lys Met Val Asn Pro Leu Asn Leu Lys Pro Ile Ser Pro
            850                 855                 860

Gln Ala Ile Val His Pro Thr Lys Pro Phe Asp Lys Phe Tyr Met Asp
865                 870                 875                 880

Tyr Ile Gly Pro Leu Pro Pro Ser Glu Gly Tyr Val His Val Leu Val
                885                 890                 895

Val Val Asp Ala Ala Thr Gly Phe Thr Trp Leu Tyr Pro Thr Lys Ala
                900                 905                 910

Gln Thr Ser Lys Ala Thr Ile Lys Val Leu Asn His Leu Thr Gly Leu
            915                 920                 925

Ala Ile Pro Lys Val Leu His Ser Asp Gln Gly Ser Ala Phe Thr Ser
            930                 935                 940

Glu Glu Phe Ala Gln Trp Ala Lys Glu Arg Asn Ile Gln Leu Glu Phe
945                 950                 955                 960

Ser Thr Pro Tyr His Pro Gln Ser Ser Gly Lys Val Glu Arg Lys Asn
                965                 970                 975

Ser Glu Ile Lys Lys Leu Leu Thr Lys Leu Leu Val Gly Arg Pro Leu
            980                 985                 990
```

Lys Trp Tyr Asn Leu Ile Ser Ser Val Gln Leu Ala Leu Asn Asn Thr
            995                1000                1005

His Val Val Ser Thr Lys Tyr Thr Pro His Gln Leu Met Phe Gly Ile
    1010                1015                1020

Asp Cys Asn Leu Pro Phe Ala Asn Lys Asp Thr Leu Asp Trp Thr Arg
1025                1030                1035                1040

Glu Glu Glu Leu Ala Leu Leu Gln Gly Ile Arg Glu Ser Leu Gln His
                1045                1050                1055

Pro Val Gln Pro Pro Thr Cys Ser Gly Trp Ser Pro Tyr Val Gly Gln
            1060                1065                1070

Leu Val Gln Glu Arg Val Tyr Arg Pro Ser Gln Leu Arg Pro Lys Trp
            1075                1080                1085

Arg Lys Pro Thr Lys Val Leu Glu Ile Leu Asn Pro Arg Thr Val Ile
    1090                1095                1100

Ile Val Asp His Leu Gly Gln Arg Lys Ser Val Ser Ile Asp Asn Leu
1105                1110                1115                1120

Lys Pro Thr Ala His Gln His Asn Gly Thr Arg Thr Cys Asp Asp Pro
                1125                1130                1135

Glu Gly Met Asp Gly Met Glu Cys Ser Gln Thr Thr Glu Thr Ser
            1140                1145                1150

Val Asp Ser Ser
        1155

<210> SEQ ID NO 16
<211> LENGTH: 1143
<212> TYPE: PRT
<213> ORGANISM: African green monkey simian foamy virus
<220> FEATURE:
<223> OTHER INFORMATION: Pol (NCBI Reference: YP_001956722.2)

<400> SEQUENCE: 16

Met Asp Pro Leu Gln Leu Leu Gln Pro Leu Glu Ala Glu Ile Lys Gly
1               5                   10                  15

Thr Lys Leu Lys Ala His Trp Asp Ser Gly Ala Thr Ile Thr Cys Val
            20                  25                  30

Pro Gln Ala Phe Leu Glu Glu Glu Val Pro Ile Lys Asn Ile Trp Ile
        35                  40                  45

Lys Thr Ile His Gly Glu Lys Glu Gln Pro Val Tyr Tyr Leu Thr Phe
    50                  55                  60

Lys Ile Gln Gly Arg Lys Val Glu Ala Glu Val Ile Ser Ser Pro Tyr
65                  70                  75                  80

Asp Tyr Ile Leu Val Ser Pro Ser Asp Ile Pro Trp Leu Met Lys Lys
                85                  90                  95

Pro Leu Gln Leu Thr Thr Leu Val Pro Leu Gln Glu Tyr Glu Glu Arg
            100                 105                 110

Leu Leu Lys Gln Thr Met Leu Thr Gly Ser Tyr Lys Glu Lys Leu Gln
        115                 120                 125

Ser Leu Phe Leu Lys Tyr Asp Ala Leu Trp Gln His Trp Glu Asn Gln
    130                 135                 140

Val Gly His Arg Arg Ile Lys Pro His His Ile Ala Thr Gly Thr Val
145                 150                 155                 160

Asn Pro Arg Pro Gln Lys Gln Tyr Pro Ile Asn Pro Lys Ala Lys Ala
                165                 170                 175

Ser Ile Gln Thr Val Ile Asn Asp Leu Leu Lys Gln Gly Val Leu Ile
            180                 185                 190

-continued

```
Gln Gln Asn Ser Ile Met Asn Thr Pro Val Tyr Pro Val Pro Lys Pro
        195                 200                 205

Asp Gly Lys Trp Arg Met Val Leu Asp Tyr Arg Glu Val Asn Lys Thr
210                 215                 220

Ile Pro Leu Ile Ala Ala Gln Asn Gln His Ser Ala Gly Ile Leu Ser
225                 230                 235                 240

Ser Ile Phe Arg Gly Lys Tyr Lys Thr Thr Leu Asp Leu Ser Asn Gly
                245                 250                 255

Phe Trp Ala His Ser Ile Thr Pro Glu Ser Tyr Trp Leu Thr Ala Phe
                260                 265                 270

Thr Trp Leu Gly Gln Gln Tyr Cys Trp Thr Arg Leu Pro Gln Gly Phe
            275                 280                 285

Leu Asn Ser Pro Ala Leu Phe Thr Ala Asp Val Val Asp Leu Leu Lys
            290                 295                 300

Glu Val Pro Asn Val Gln Val Tyr Val Asp Asp Ile Tyr Ile Ser His
305                 310                 315                 320

Asp Asp Pro Arg Glu His Leu Glu Gln Leu Glu Lys Val Phe Ser Leu
                325                 330                 335

Leu Leu Asn Ala Gly Tyr Val Val Ser Leu Lys Lys Ser Glu Ile Ala
            340                 345                 350

Gln His Glu Val Glu Phe Leu Gly Phe Asn Ile Thr Lys Glu Gly Arg
        355                 360                 365

Gly Leu Thr Glu Thr Phe Lys Gln Lys Leu Leu Asn Ile Thr Pro Pro
370                 375                 380

Arg Asp Leu Lys Gln Leu Gln Ser Ile Leu Gly Leu Leu Asn Phe Ala
385                 390                 395                 400

Arg Asn Phe Ile Pro Asn Phe Ser Glu Leu Val Lys Pro Leu Tyr Asn
                405                 410                 415

Ile Ile Ala Thr Ala Asn Gly Lys Tyr Ile Thr Trp Thr Thr Asp Asn
            420                 425                 430

Ser Gln Gln Leu Gln Asn Ile Ile Ser Met Leu Asn Ser Ala Glu Asn
        435                 440                 445

Leu Glu Glu Arg Asn Pro Glu Val Arg Leu Ile Met Lys Val Asn Thr
    450                 455                 460

Ser Pro Ser Ala Gly Tyr Ile Arg Phe Tyr Asn Glu Phe Ala Lys Arg
465                 470                 475                 480

Pro Ile Met Tyr Leu Asn Tyr Val Tyr Thr Lys Ala Glu Val Lys Phe
                485                 490                 495

Thr Asn Thr Glu Lys Leu Leu Thr Thr Ile His Lys Gly Leu Ile Lys
            500                 505                 510

Ala Leu Asp Leu Gly Met Gly Gln Glu Ile Leu Val Tyr Ser Pro Ile
        515                 520                 525

Val Ser Met Thr Lys Ile Gln Lys Thr Pro Leu Pro Glu Arg Lys Ala
530                 535                 540

Leu Pro Ile Arg Trp Ile Thr Trp Met Ser Tyr Leu Glu Asp Pro Arg
545                 550                 555                 560

Ile Gln Phe His Tyr Asp Lys Thr Leu Pro Glu Leu Gln Gln Val Pro
                565                 570                 575

Thr Val Thr Asp Asp Ile Ile Ala Lys Ile Lys His Pro Ser Glu Phe
            580                 585                 590

Ser Met Val Phe Tyr Thr Asp Gly Ser Ala Ile Lys His Pro Asn Val
        595                 600                 605
```

-continued

```
Asn Lys Ser His Asn Ala Gly Met Gly Ile Ala Gln Val Gln Phe Lys
    610                 615                 620
Pro Glu Phe Thr Val Ile Asn Thr Trp Ser Ile Pro Leu Gly Asp His
625                 630                 635                 640
Thr Ala Gln Leu Ala Glu Val Ala Ala Val Glu Phe Ala Cys Lys Lys
                645                 650                 655
Ala Leu Lys Ile Asp Gly Pro Val Leu Ile Val Thr Asp Ser Phe Tyr
                660                 665                 670
Val Ala Glu Ser Val Asn Lys Glu Leu Pro Tyr Trp Gln Ser Asn Gly
                675                 680                 685
Phe Phe Asn Asn Lys Lys Pro Leu Lys His Val Ser Lys Trp Lys
690                 695                 700
Ser Ile Ala Asp Cys Ile Gln Leu Lys Pro Asp Ile Ile Ile His
705                 710                 715                 720
Glu Lys Gly His Gln Pro Thr Ala Ser Thr Phe His Thr Glu Gly Asn
                    725                 730                 735
Asn Leu Ala Asp Lys Leu Ala Thr Gln Gly Ser Tyr Val Val Asn Ile
                740                 745                 750
Asn Thr Thr Pro Ser Leu Asp Ala Glu Leu Asp Gln Leu Leu Gln Gly
        755                 760                 765
Gln Tyr Pro Lys Gly Phe Pro Lys His Tyr Gln Tyr Gln Leu Glu Asn
770                 775                 780
Gly Gln Val Met Val Thr Arg Pro Asn Gly Lys Arg Ile Ile Pro Pro
785                 790                 795                 800
Lys Ser Asp Arg Pro Gln Ile Ile Leu Gln Ala His Asn Ile Ala His
                    805                 810                 815
Thr Gly Arg Asp Ser Thr Phe Leu Lys Val Ser Ser Lys Tyr Trp Trp
                820                 825                 830
Pro Asn Leu Arg Lys Asp Val Val Lys Val Ile Arg Gln Cys Lys Gln
            835                 840                 845
Cys Leu Val Thr Asn Ala Ala Thr Leu Ala Ala Pro Pro Ile Leu Arg
850                 855                 860
Pro Glu Arg Pro Val Lys Pro Phe Asp Lys Phe Phe Ile Asp Tyr Ile
865                 870                 875                 880
Gly Pro Leu Pro Pro Ser Asn Gly Tyr Leu His Val Leu Val Val Val
                    885                 890                 895
Asp Ser Met Thr Gly Phe Val Trp Leu Tyr Pro Thr Lys Ala Pro Ser
                900                 905                 910
Thr Ser Ala Thr Val Lys Ala Leu Asn Met Leu Thr Ser Ile Ala Val
            915                 920                 925
Pro Lys Val Ile His Ser Asp Gln Gly Ala Ala Phe Thr Ser Ala Thr
930                 935                 940
Phe Ala Asp Trp Ala Lys Asn Lys Gly Ile Gln Leu Glu Phe Ser Thr
945                 950                 955                 960
Pro Tyr His Pro Gln Ser Ser Gly Lys Val Glu Arg Lys Asn Ser Asp
                    965                 970                 975
Ile Lys Arg Leu Leu Thr Lys Leu Leu Val Gly Arg Pro Ala Lys Trp
            980                 985                 990
Tyr Asp Leu Leu Pro Val Gln Leu Ala Leu Asn Asn Ser Tyr Ser
                995                 1000                1005
Pro Ser Ser Lys Tyr Thr Pro His Gln Leu Leu Phe Gly Ile Asp Ser
        1010                1015                1020
Asn Thr Pro Phe Ala Asn Ser Asp Thr Leu Asp Leu Ser Arg Glu Glu
```

```
1025                1030                1035                1040
Glu Leu Ser Leu Leu Gln Glu Ile Arg Ser Ser Leu Tyr Leu Pro Ser
                1045                1050                1055

Thr Pro Pro Ala Ser Ile Arg Ala Trp Ser Pro Ser Val Gly Gln Leu
                1060                1065                1070

Val Gln Glu Arg Val Ala Arg Pro Ala Ser Leu Arg Pro Arg Trp His
                1075                1080                1085

Lys Pro Thr Pro Val Leu Glu Val Ile Asn Pro Arg Ala Val Val Ile
        1090                1095                1100

Leu Asp His Leu Gly Asn Arg Arg Thr Val Ser Val Asp Asn Leu Lys
1105                1110                1115                1120

Leu Thr Ala Tyr Gln Lys Asp Gly Thr Pro Asn Glu Ser Ala Ala Val
                1125                1130                1135

Val Ala Met Glu Lys Asp Glu
                1140

<210> SEQ ID NO 17
<211> LENGTH: 1134
<212> TYPE: PRT
<213> ORGANISM: Squirrel monkey foamy virus
<220> FEATURE:
<223> OTHER INFORMATION: Pol (GenBank: ADE05995.1)

<400> SEQUENCE: 17

Met Tyr Gln Pro Gln His Gln Leu Gln Val Glu Ile His Asp Gln Lys
1               5                   10                  15

Leu Ile Gly Tyr Trp Asp Thr Gly Ala Gln Ile Thr Cys Ile Pro Gln
            20                  25                  30

Val Tyr Leu Glu Gln Glu Lys Pro Ile Gly Lys His Val Ile Glu Thr
        35                  40                  45

Val Asn Gly Lys Thr Gln Arg Asp Ala Tyr Tyr Ile Lys Leu Lys Ile
    50                  55                  60

Asn Gly Lys Lys Ile Glu Thr Glu Val Ile Pro Ser Pro Phe Ser Tyr
65                  70                  75                  80

Ala Leu Ile Thr Pro Asn Asp Ile Pro Trp Phe Lys Pro Gly Gly Ile
            85                  90                  95

Glu Leu Thr Glu Lys Leu Pro Ile Gln Asp Tyr Lys Asp Asn Ile Val
        100                 105                 110

Lys Arg Ala Asp Ile Thr Lys Glu Glu Lys Gly Met Leu Tyr Lys Leu
    115                 120                 125

Leu Asp Lys Tyr Asp Pro Leu Trp Gln Gln Trp Glu Asn Gln Val Gly
    130                 135                 140

Asn Arg Gln Ile Thr Pro His Ile Ile Ala Thr Gly Thr Ile Asn Pro
145                 150                 155                 160

Lys Pro Gln Lys Gln Tyr His Ile Asn Pro Lys Ala Lys Pro Ser Ile
            165                 170                 175

Gln Ile Val Ile Asn Asp Leu Leu Lys Gln Gly Val Leu Lys Gln Gln
        180                 185                 190

Asn Ser Ile Met Asn Thr Pro Ile Tyr Pro Val Pro Lys Thr Glu Gly
    195                 200                 205

Lys Trp Arg Met Val Leu Asp Tyr Arg Ala Val Asn Lys Thr Ile Pro
    210                 215                 220

Leu Ile Ala Ala Gln Asn Gln His Ser Ala Gly Ile Leu Thr Asn Leu
225                 230                 235                 240

Val Arg Gln Lys Tyr Lys Ser Thr Ile Asp Leu Ser Asn Gly Phe Trp
```

```
                245                 250                 255
Ala His Pro Ile Asp Gln Asp Ser Gln Trp Ile Thr Ala Phe Thr Trp
            260                 265                 270

Glu Gly Lys Gln Tyr Val Trp Thr Arg Leu Pro Gln Gly Phe Leu Asn
        275                 280                 285

Ser Pro Ala Leu Phe Thr Ala Asp Val Val Asp Leu Leu Lys Glu Ile
    290                 295                 300

Pro Asn Val Asn Val Tyr Val Asp Asp Ile Tyr Val Ser Thr Glu Thr
305                 310                 315                 320

Ile Asn Gln His Phe Gln Val Leu Asp Lys Ile Phe Gln Lys Leu Leu
                325                 330                 335

Gln Ala Gly Tyr Val Val Ser Leu Lys Lys Ser Asn Leu Cys Arg Tyr
            340                 345                 350

Glu Val Thr Phe Leu Gly Phe Thr Ile Ser Lys Tyr Gly Arg Gly Leu
        355                 360                 365

Thr Glu Glu Phe Gln Glu Lys Leu Arg Asn Ile Ser Pro Pro Asn Ser
    370                 375                 380

Leu Lys Gln Leu Gln Ser Ile Leu Gly Leu Leu Asn Phe Ala Arg Asn
385                 390                 395                 400

Phe Ile Pro Asn Phe Ser Glu Leu Ile Lys Pro Leu Tyr Glu Leu Ile
                405                 410                 415

Ser Thr Ala Gln Gly Gln Ser Ile Ser Trp Glu Pro Lys His Ser Gln
            420                 425                 430

Ala Leu Asn Asn Leu Ile Ile Ala Leu Asn His Ala Asp Asn Leu Glu
        435                 440                 445

Gln Arg Asn Gly Glu Val Pro Leu Val Ile Lys Ile Asn Ala Ser Asn
    450                 455                 460

Thr Thr Gly Tyr Ile Arg Phe Tyr Asn Lys Asn Gly Lys Arg Pro Ile
465                 470                 475                 480

Ala Tyr Ala Ser His Val Phe Asn His Thr Glu Gln Lys Phe Thr Pro
                485                 490                 495

Val Glu Lys Leu Leu Thr Thr Met His Lys Ala Ile Ile Lys Gly Ile
            500                 505                 510

Asp Leu Ala Ile Gly Gln Pro Ile Glu Ile Tyr Ser Pro Ile Val Ser
        515                 520                 525

Met Gln Lys Leu Gln Lys Ile Thr Leu Pro Glu Arg Lys Ala Leu Ser
    530                 535                 540

Thr Arg Trp Leu Ser Trp Leu Ser Tyr Ile Glu Asp Pro Arg Phe Leu
545                 550                 555                 560

Phe Ile Tyr Asp Lys Thr Leu Pro Asp Leu Lys Glu Met Pro Pro Thr
                565                 570                 575

Gln Thr Asp Asp Tyr Asn Pro Met Leu Pro Leu His Gln Tyr Leu Ala
            580                 585                 590

Val Phe Tyr Thr Asp Gly Ser Ser Ile Lys Ser Pro Asp Pro Thr Lys
        595                 600                 605

Thr His Ser Ser Gly Met Gly Ile Val Gln Ala Ile Tyr Glu Pro Asn
    610                 615                 620

Phe Gln Ile Lys His Gln Trp Ser Ile Pro Leu Gly Asp His Thr Ala
625                 630                 635                 640

Gln Tyr Ala Glu Ile Ala Ala Val Glu Phe Ala Cys Lys Lys Ala Leu
                645                 650                 655

Gln Val Thr Gly Pro Val Leu Ile Val Thr Asp Ser Asp Tyr Val Ala
            660                 665                 670
```

```
Arg Ser Val Asn Asn Glu Leu Asn Phe Trp Arg Ser Asn Gly Phe Val
    675                 680                 685

Asn Asn Lys Lys Pro Leu Lys His Ile Ser Lys Trp Lys Ser Ile
690                 695                 700

Ser Glu Ser Leu Leu His Lys Asn Ile Thr Ile Val His Glu Pro
705                 710                 715                 720

Gly His Gln Pro Ser Ser Thr Ser Val His Thr Gln Gly Asn Ala Leu
                725                 730                 735

Ala Asp Lys Leu Ala Val Gln Gly Ser Tyr Thr Ile Asn Asn Ile Thr
                740                 745                 750

Ile Lys Pro Ser Leu Asp Thr Glu Leu Arg Ala Val Leu Glu Gly Lys
                755                 760                 765

Leu Pro Lys Gly Tyr Pro Lys Asn Leu Lys Tyr Glu Tyr Asn Ser Pro
770                 775                 780

Asn Leu Ile Val Ile Arg Lys Glu Gly Gln Arg Ile Ile Pro Pro Leu
785                 790                 795                 800

Ser Asp Arg Pro Lys Leu Val Lys Gln Ala His Glu Leu Ala His Thr
                805                 810                 815

Gly Arg Glu Ala Thr Leu Leu Arg Leu Gln Asn Gln Tyr Trp Trp Pro
                820                 825                 830

Lys Met Arg Lys Asp Val Ser His Cys Leu Arg Thr Cys Met Pro Cys
                835                 840                 845

Leu Gln Thr Asn Ser Thr Asn Leu Thr Thr Thr Arg Pro Phe Gln Gln
850                 855                 860

Ile Arg Pro Ser Lys Pro Phe Asp Lys Tyr Tyr Ile Asp Tyr Ile Gly
865                 870                 875                 880

Pro Leu Pro Pro Ser Glu Gly Tyr Ser Tyr Val Leu Val Val Val Asp
                885                 890                 895

Ser Ala Thr Gly Phe Cys Trp Leu Tyr Pro Thr Lys Ala Pro Ser Thr
                900                 905                 910

Arg Ala Thr Val Lys Ser Leu Asn Phe Leu Leu Gly Ile Ala Val Pro
                915                 920                 925

Lys Ile Leu His Ser Asp Gln Gly Ser Ala Phe Thr Ser Ser Asp Phe
930                 935                 940

Ala Asn Trp Ala Lys Glu Lys Glu Ile Thr Leu Glu Phe Ser Thr Pro
945                 950                 955                 960

Tyr His Pro Gln Ser Ser Gly Lys Val Glu Arg Lys Asn Gln Glu Ile
                965                 970                 975

Lys Lys Leu Leu Thr Lys Leu Leu Val Gly Arg Pro Ala Lys Trp Tyr
                980                 985                 990

Pro Leu Ile Pro Ser Val Gln Leu Ala Leu Asn Asn Thr Tyr Ser Pro
                995                 1000                1005

Lys Ile Lys Leu Thr Pro His Gln Leu Leu Phe Gly Val Asp Gly Asn
        1010                1015                1020

Ile Pro Phe Ala Asn Ser Asp Thr Leu Asp Leu Lys Arg Glu Glu Glu
1025                1030                1035                1040

Leu Ala Leu Leu Ser Glu Ile Arg Thr Thr Leu Ser Thr Val Ser Pro
                1045                1050                1055

Glu Pro Phe Pro Ser Thr Ala Lys Thr Trp Thr Pro Ser Val Gly Leu
                1060                1065                1070

Leu Val Gln Glu Arg Val Tyr Arg Pro Ser Gln Leu Arg Pro Lys Trp
                1075                1080                1085
```

-continued

```
Lys Lys Pro Thr Pro Ile Leu Glu Val Leu Asn Glu Arg Thr Val Val
    1090                1095                1100
Ile Asp Asn Asn Gly Gln Arg Arg Thr Val Ser Val Asp Asn Leu Lys
1105                1110                1115                1120
Tyr Thr Pro His Gln Lys Asp Gly Glu Thr Tyr Asp Ser Ser
                1125                1130
```

<210> SEQ ID NO 18
<211> LENGTH: 1153
<212> TYPE: PRT
<213> ORGANISM: equine foamy virus
<220> FEATURE:
<223> OTHER INFORMATION: Pol (NCBI Reference: NP_054716.1)

<400> SEQUENCE: 18

```
Met Gln Ala Leu Gln Pro Leu Gln Val Gln Ile Lys Gly Asn Ser Leu
1               5                   10                  15
Lys Gly Phe Tyr Asp Thr Gly Ala Glu Ile Thr Cys Val Pro Ala Ile
            20                  25                  30
Phe Leu Ile Glu Glu Glu Pro Ile Gly Glu Arg Thr Ile Gln Thr Ile
        35                  40                  45
His Gly Ile Thr Lys Glu Lys Val Tyr Tyr Leu Thr Phe Lys Ile Gln
    50                  55                  60
Gly Arg Lys Leu Ala Ala Glu Val Ile Gly Thr Gln Leu Asp Tyr Val
65                  70                  75                  80
Ile Ile Ala Pro Ser Asp Ile Pro Trp Tyr Lys Lys Tyr Glu Leu Glu
                85                  90                  95
Leu Thr Ile Lys Ile Asp Ile Gln Lys Gln Glu Gln Leu Leu His
            100                 105                 110
Thr Thr Asn Leu Ser Ser Glu Gly Lys Lys Tyr Leu Lys Asp Leu Phe
        115                 120                 125
Ile Lys Tyr Asp Asn Leu Trp Gln Lys Trp Glu Asn Gln Val Gly His
    130                 135                 140
Arg Arg Ile Thr Pro His Lys Ile Ala Thr Gly Thr Leu Asn Pro Lys
145                 150                 155                 160
Pro Gln Lys Gln Tyr Arg Ile Asn Pro Lys Ala Lys Ala Asp Ile Gln
                165                 170                 175
Ile Val Ile Asp Asp Leu Leu Lys Gln Gly Val Leu Lys Gln Gln Thr
            180                 185                 190
Ser Pro Met Asn Thr Pro Val Tyr Pro Val Pro Lys Pro Asp Gly Arg
        195                 200                 205
Trp Arg Met Val Leu Asp Tyr Arg Ala Val Asn Lys Val Thr Pro Ala
    210                 215                 220
Ile Ala Thr Gln Asn Cys His Ser Ala Ser Leu Leu Asn Thr Leu Tyr
225                 230                 235                 240
Arg Gly Gln Tyr Lys Thr Thr Leu Asp Leu Ala Asn Gly Phe Trp Ala
                245                 250                 255
His Pro Ile Gln Glu Ser Asp Gln Trp Ile Thr Ser Phe Thr Trp Asn
            260                 265                 270
Gly Lys Ser Tyr Val Trp Thr Thr Leu Pro Gln Gly Phe Leu Asn Ser
        275                 280                 285
Pro Ala Leu Phe Thr Ala Asp Val Val Asp Leu Leu Lys Asp Ile Pro
    290                 295                 300
Asn Val Glu Val Tyr Val Asp Asp Val Tyr Phe Ser Asn Asp Thr Glu
305                 310                 315                 320
```

```
Glu Glu His Leu Lys Thr Met Asp Leu Leu Phe Gln Lys Leu Gln Thr
            325                 330                 335
Ala Gly Tyr Ile Val Ser Leu Lys Lys Ser Lys Leu Gly Gln His Thr
            340                 345                 350
Val Asp Phe Leu Gly Phe Gln Ile Thr Gln Thr Gly Arg Gly Leu Thr
            355                 360                 365
Asp Ser Tyr Lys Ser Lys Leu Leu Asp Ile Thr Pro Pro Asn Thr Leu
    370                 375                 380
Lys Gln Leu Gln Ser Ile Leu Gly Leu Leu Asn Phe Ala Arg Asn Phe
385                 390                 395                 400
Ile Pro Asn Tyr Ser Glu Leu Ile Thr Pro Leu Tyr Gln Leu Ile Pro
                405                 410                 415
Leu Ala Lys Gly Ile Tyr Ile Pro Trp Glu Thr Lys His Thr Ala Ile
            420                 425                 430
Leu Gln Lys Ile Ile Lys Glu Leu Asn Ala Ser Glu Asn Leu Glu Gln
            435                 440                 445
Arg Lys Pro Asp Val Glu Leu Ile Val Lys Val His Val Ser Pro Thr
    450                 455                 460
Ala Gly Tyr Ile Lys Phe Ala Asn Lys Gly Ser Ile Lys Pro Ile Ala
465                 470                 475                 480
Tyr His Asn Val Val Phe Ser Lys Thr Glu Leu Lys Phe Thr Ile Thr
                485                 490                 495
Glu Lys Val Met Thr Thr Ile His Lys Ala Leu Leu Lys Ala Phe Asp
            500                 505                 510
Leu Ala Met Gly Gln Pro Ile Trp Val Tyr Ser Pro Ile His Ser Met
            515                 520                 525
Thr Arg Ile Gln Lys Thr Pro Leu Thr Glu Arg Lys Ala Leu Ser Ile
    530                 535                 540
Arg Trp Leu Lys Trp Gln Thr Tyr Phe Glu Asp Pro Arg Leu Ile Phe
545                 550                 555                 560
His Tyr Asp Asp Thr Leu Pro Asp Leu Gln Asn Leu Pro Gln Thr Thr
                565                 570                 575
Leu Gly Asn Glu Val Asp Ile Leu Pro Leu Ser Glu Tyr Glu Val Val
            580                 585                 590
Phe Tyr Thr Asp Gly Ser Ser Ile Lys Ser Pro Lys Lys Asp Lys Gln
            595                 600                 605
His Ser Ala Gly Met Gly Ile Ile Ala Val Arg Tyr Gln Pro Gln Met
    610                 615                 620
Asn Ile Ile Gln Glu Trp Ser Pro Leu Gly Asp His Thr Ala Gln
625                 630                 635                 640
Phe Ala Glu Ile Ala Ala Phe Glu Phe Ala Leu Lys Gln Ala Ile Arg
                645                 650                 655
Lys Met Gly Pro Val Leu Ile Val Thr Asp Ser Asp Tyr Val Ala Lys
            660                 665                 670
Ser Tyr Asn Gln Glu Leu Asp Phe Trp Val Ser Asn Gly Phe Val Asn
    675                 680                 685
Asn Lys Lys Lys Pro Leu Lys His Val Ser Lys Trp Lys Ser Ile Ala
690                 695                 700
Asp Cys Lys Lys His Lys Ala Asp Ile His Val Ile His Glu Pro Gly
705                 710                 715                 720
His Gln Asn Asp Leu Gln Ser Pro Tyr Ala Met Gly Asn Asn Ala Ala
                725                 730                 735
Asp Lys Leu Ala Val Lys Ala Ser Tyr Thr Val Phe Ser Val Gln Thr
```

Leu Pro Ser Leu Asp Ala Glu Leu His Gln Leu Leu Asp Lys Gln Thr
            740                 745                 750
Pro Asn Pro Lys Gly Tyr Pro Ser Lys Tyr Glu Tyr Thr Leu Arg Asp
        755                 760                 765
Gly Gln Val Tyr Val Lys Arg Thr Asp Gly Glu Lys Ile Ile Pro Ser
    770                 775                 780
Lys Asp Asp Arg Val Lys Ile Leu Glu Leu Ala His Lys Gly Pro Gly
785                 790                 795                 800
Ser Gly His Leu Gly Lys Asn Thr Met Tyr Ile Lys Ile Leu Asn Lys
            805                 810                 815
Tyr Trp Trp Pro Asn Leu Ile Lys Asp Ile Ser Lys Tyr Ile Arg Thr
        820                 825                 830
Cys Thr Asn Cys Ile Ile Thr Asn Thr Asp Asn Val Pro Asn Lys Ser
    835                 840                 845
Tyr Ile Val Gln Glu Lys Thr Gly Leu Pro Phe Gln Lys Tyr Tyr Met
850                 855                 860
Asp Tyr Ile Gly Pro Leu Pro Pro Ser Asp Gly Tyr Tyr His Val Leu
            865                 870                 875                 880
Val Ile Val Asp Glu Gly Thr Gly Tyr Thr Trp Leu Tyr Pro Thr Lys
        885                 890                 895
Ala Gln Thr Ala Asn Ala Thr Val Lys Ala Leu Asn His Leu Thr Gly
    900                 905                 910
Thr Ala Ile Pro Lys Val Leu His Ser Asp Gln Gly Ser Ala Phe Thr
            915                 920                 925
Ser Ala Thr Leu Val Ala Trp Ala Lys Asp Lys Gly Ile Gln Met Glu
945             930                 935                 940
Tyr Ser Ser Pro Tyr His Pro Gln Ser Ser Gly Lys Val Glu Arg Lys
        950                 955                 960
Asn Ser Glu Ile Lys Arg Leu Leu Thr Lys Leu Leu Val Gly Arg Pro
    965                 970                 975
Thr Lys Trp Tyr Pro Leu Ile Pro Thr Val Gln Leu Ala Leu Asn Asn
            980                 985                 990
Thr Pro Asn Ala Lys Ile Gly Lys Thr Pro His Gln Leu Met Tyr Gly
        995                 1000                1005
Val Asp Cys Asn Leu Pro Phe Gln Asp Leu Ser Thr Leu Asp Leu Thr
1025            1010                1015                1020
Arg Glu Glu Gln Leu Ala Val Leu Gln Glu Ile Arg Thr Ala Leu Glu
        1030                1035                1040
Gln Pro Ala Gln His Pro Thr Leu Pro Lys Trp Thr Pro Cys Pro Gly
    1045                1050                1055
Leu Leu Val Gln Glu Arg Val Asn Arg Pro Ala Gln Leu Arg Pro Lys
            1060                1065                1070
Trp Lys Lys Pro Thr Pro Ile Leu Lys Val Leu Asn Pro Lys Thr Val
        1075                1080                1085
Val Ile Ala Gly Pro Gly Gly Gln Glu Arg Ile Val Ser Ile Asp Asn
1105            1090                1095                1100
Leu Lys Lys Thr Pro His His Asp Thr Ser Asn Asp Ser Thr Arg Met
        1110                1115                1120
Asp Ala Val Glu Val Pro Thr Glu Cys Gln Gln Asp Gln Arg Gly His
    1125                1130                1135
Thr
            1140                1145                1150

<210> SEQ ID NO 19
<211> LENGTH: 1220
<212> TYPE: PRT
<213> ORGANISM: Bovine foamy virus
<220> FEATURE:
<223> OTHER INFORMATION: Pol (GenBank: AFR79239.1)

<400> SEQUENCE: 19

```
Met Pro Ala Leu Arg Pro Leu Gln Val Glu Ile Lys Gly Asn His Leu
1               5                   10                  15

Lys Gly Tyr Trp Asp Ser Gly Ala Glu Ile Thr Cys Val Pro Ala Ile
            20                  25                  30

Tyr Val Ile Glu Glu Gln Pro Val Gly Lys Lys Leu Ile Thr Thr Ile
        35                  40                  45

His Asp Glu Lys Glu His Asp Val Tyr Tyr Val Glu Met Lys Val Glu
    50                  55                  60

Lys Arg Lys Val Gln Cys Glu Val Ile Thr Thr Ala Leu Asp Tyr Val
65                  70                  75                  80

Leu Val Ala Pro Ile Asp Ile Pro Trp Tyr Lys Pro Gly Pro Leu Glu
                85                  90                  95

Leu Thr Ile Lys Ile Asp Val Glu Ser Gln Lys His Ala Leu Ile Thr
            100                 105                 110

Gly Ser Thr Leu Ser Pro Gln Gly Arg Met Arg Leu Lys Lys Leu Leu
        115                 120                 125

Asp Gln Tyr Gln Ala Leu Trp Gln Cys Trp Glu Asn Gln Val Gly His
    130                 135                 140

Arg Arg Ile Glu Pro His Lys Ile Ala Thr Gly Thr Leu Lys Pro Arg
145                 150                 155                 160

Pro Gln Lys Gln Tyr His Val Asn Pro Arg Ala Lys Ala Asp Ile Gln
                165                 170                 175

Val Val Ile Asp Asp Leu Leu Arg Gln Gly Val Leu Arg Gln Gln Asn
            180                 185                 190

Ser Glu Met Asn Thr Pro Val Tyr Pro Val Pro Lys Ala Asp Gly Arg
        195                 200                 205

Trp Arg Met Val Leu Asp Tyr Arg Glu Val Asn Lys Val Thr Pro Leu
    210                 215                 220

Val Ala Thr Gln Asn Cys His Ser Ala Ser Ile Leu Asn Thr Leu Tyr
225                 230                 235                 240

Arg Gly Pro Tyr Lys Ser Thr Leu Asp Leu Ala Asn Gly Phe Trp Ala
                245                 250                 255

His Pro Ile Lys Pro Glu Asp Tyr Trp Ile Thr Ala Phe Thr Trp Gly
            260                 265                 270

Gly Lys Thr Tyr Cys Trp Thr Val Leu Pro Gln Gly Phe Leu Asn Ser
        275                 280                 285

Pro Ala Leu Phe Thr Ala Asp Val Val Asp Ile Leu Lys Asp Ile Pro
    290                 295                 300

Asn Val Gln Val Tyr Val Asp Asp Val Tyr Val Ser Ser Ala Thr Glu
305                 310                 315                 320

Gln Glu His Leu Asp Thr Leu Glu Ile Ile Phe Asn Arg Leu Ser Thr
                325                 330                 335

Ala Gly Tyr Ile Val Ser Leu Lys Lys Ser Lys Leu Ala Lys Glu Thr
            340                 345                 350

Val Glu Phe Leu Gly Phe Ser Ile Ser Gln Asn Gly Arg Gly Leu Thr
        355                 360                 365
```

-continued

```
Asp Ser Tyr Lys Gln Lys Leu Met Asp Leu Gln Pro Thr Thr Leu
    370                 375                 380

Arg Gln Leu Gln Ser Ile Leu Gly Leu Ile Asn Phe Ala Arg Asn Phe
385                 390                 395                 400

Leu Pro Asn Phe Ala Glu Leu Val Ala Pro Leu Tyr Gln Leu Ile Pro
                405                 410                 415

Lys Ala Lys Gly Gln Cys Ile Pro Trp Thr Met Asp His Thr Thr Gln
            420                 425                 430

Leu Lys Thr Ile Ile Gln Ala Leu Asn Ser Thr Glu Asn Leu Glu Glu
        435                 440                 445

Arg Arg Pro Asp Val Asp Leu Ile Met Lys Val His Ile Ser Asn Thr
450                 455                 460

Ala Gly Tyr Ile Arg Phe Tyr Asn His Gly Gly Gln Lys Pro Ile Ala
465                 470                 475                 480

Tyr Asn Asn Ala Leu Phe Thr Ser Thr Glu Leu Lys Phe Thr Pro Thr
                485                 490                 495

Glu Lys Ile Met Ala Thr Ile His Lys Gly Leu Leu Lys Ala Leu Asp
            500                 505                 510

Leu Ser Leu Gly Lys Glu Ile His Val Tyr Ser Ala Ile Ala Ser Met
        515                 520                 525

Thr Lys Leu Gln Lys Thr Pro Leu Thr Glu Arg Lys Ala Leu Ser Ile
530                 535                 540

Arg Trp Leu Lys Trp Gln Thr Tyr Phe Glu Asp Pro Arg Ile Lys Phe
545                 550                 555                 560

His His Asp Ala Thr Leu Pro Asp Leu Gln Asn Leu Pro Ile Pro Gln
                565                 570                 575

Gln Asp Thr Gly Lys Glu Val Thr Ile Leu Pro Leu Leu His Tyr Glu
            580                 585                 590

Ala Ile Phe Tyr Thr Asp Gly Ser Ala Ile Arg Ser Pro Lys Pro Asn
        595                 600                 605

Lys Thr His Ser Ala Gly Met Gly Ile Ile Gln Ala Lys Phe Glu Pro
610                 615                 620

Asp Phe Lys Ile Val His Leu Trp Ser Phe Pro Leu Gly Asp His Thr
625                 630                 635                 640

Ala Gln Tyr Ala Glu Ile Ala Ala Phe Glu Phe Ala Met Arg Arg Ala
                645                 650                 655

Thr Gly Ile Arg Gly Pro Val Leu Ile Val Thr Asp Ser Asn Tyr Val
            660                 665                 670

Ala Lys Ser Tyr Asn Glu Glu Leu Pro Tyr Trp Glu Ser Asn Gly Phe
        675                 680                 685

Val Asn Asn Lys Lys Lys Thr Leu Lys His Ile Ser Lys Trp Lys Thr
690                 695                 700

Ile Ala Glu Cys Lys Asn Leu Lys Ala Asp Ile His Val Ile His Glu
705                 710                 715                 720

Pro Gly His Gln Pro Ala Glu Ala Ser Pro His Ala Gln Gly Asn Ala
                725                 730                 735

Leu Ala Asp Lys Gln Ala Val Ser Gly Ser Tyr Lys Val Phe Ser Asn
            740                 745                 750

Glu Leu Lys Pro Ser Leu Asp Ala Glu Leu Glu Gln Val Leu Ser Ala
        755                 760                 765

Gly Arg Pro Asn Pro Gln Gly Tyr Pro Asn Lys Tyr Glu Tyr Lys Leu
770                 775                 780

Val Asn Gly Leu Cys Tyr Val Asp Arg Arg Gly Glu Glu Gly Leu Lys
```

-continued

```
           785                 790                 795                 800
    Ile Ile Pro Pro Lys Ala Asp Arg Ala Lys Leu Cys Gln Leu Ala His
                        805                 810                 815

Asp Gly Pro Gly Ser Ala His Leu Gly Arg Thr Ala Leu Leu Leu Lys
                        820                 825                 830

Leu Gln Gln Lys Tyr Trp Trp Pro Lys Met His Ile Asp Ala Ser Arg
                835                 840                 845

Thr Val Leu Asn Cys Thr Val Cys Ala Gln Thr Asn Pro Thr Asn Gln
            850                 855                 860

Lys Pro Arg Pro Pro Leu Val Ile Pro His Asp Thr Lys Pro Phe Gln
865                 870                 875                 880

Val Trp Tyr Met Asp Tyr Ile Gly Pro Leu Pro Pro Ser Asn Gly Tyr
                        885                 890                 895

His His Ala Leu Val Ile Val Asp Ala Gly Thr Gly Phe Thr Trp Ile
                        900                 905                 910

Tyr Pro Thr Lys Ala Gln Thr Ala Asn Ala Thr Val Lys Ala Leu Thr
                915                 920                 925

His Leu Thr Gly Thr Ala Val Pro Lys Val Leu His Ser Asp Gln Gly
            930                 935                 940

Pro Ala Phe Thr Ser Ser Ile Leu Ala Asp Trp Ala Lys Asp Arg Gly
945                 950                 955                 960

Ile Gln Leu Glu His Ser Ala Pro Tyr His Pro Gln Ser Ser Gly Lys
                        965                 970                 975

Val Glu Arg Lys Asn Ser Glu Ile Lys Arg Leu Leu Thr Lys Leu Leu
                        980                 985                 990

Ala Gly Arg Pro Thr Lys Trp Tyr Pro Leu Ile Pro Ile Val Gln Leu
                995                 1000                1005

Ala Leu Asn Asn Thr Pro Asn Thr Arg Gln Lys Tyr Thr Pro His Gln
            1010                1015                1020

Leu Met Tyr Gly Val Asp Cys Asn Leu Pro Phe Glu Asn Leu Asp Thr
1025                1030                1035                1040

Leu Asp Leu Thr Arg Glu Glu Gln Leu Ala Val Leu Lys Glu Val Arg
                        1045                1050                1055

Asp Gly Leu Leu Asp Ser Tyr Pro Ser Pro Ser Gln Thr Thr Ala Arg
                        1060                1065                1070

Ser Trp Thr Pro Ser Pro Gly Leu Leu Val Gln Glu Arg Val Ala Arg
                1075                1080                1085

Pro Ala Gln Leu Arg Pro Lys Trp Arg Lys Pro Ala Pro Ile Lys Lys
            1090                1095                1100

Val Leu Asn Glu Arg Thr Val Ile Ile Asp His Leu Gly Gln Asp Lys
1105                1110                1115                1120

Val Val Ser Ile Asp Asn Leu Lys Pro Ala Ala His Gln Lys Leu Ala
                        1125                1130                1135

Gln Thr Pro Asp Ser Ala Glu Ile Cys Pro Ser Ala Thr Pro Cys Pro
                        1140                1145                1150

Pro Asn Thr Ser Leu Trp Tyr Asp Leu Asp Thr Asp Thr Trp Thr Cys
                1155                1160                1165

Gln Arg Cys Gly Tyr Gln Cys Pro Asp Lys Tyr His Gln Pro Gln Cys
            1170                1175                1180

Thr Trp Ser Cys Glu Asp Arg Cys Gly His Arg Trp Lys Glu Cys Gly
1185                1190                1195                1200

Asn Cys Ile Pro Arg Asp Gly Ser Ser Asp Asp Ala Ser Ala Met Ala
                        1205                1210                1215
```

```
Thr Val Glu Val
        1220

<210> SEQ ID NO 20
<211> LENGTH: 1149
<212> TYPE: PRT
<213> ORGANISM: Feline Foamy virus
<220> FEATURE:
<223> OTHER INFORMATION: Pol (GenBank: CAA11581.1)

<400> SEQUENCE: 20

Met Asp Pro Leu Gln Leu Leu Gln Pro Leu Glu Ala Glu Ile Lys Gly
1               5                   10                  15

Thr Lys Leu Lys Ala His Trp Asp Ser Gly Ala Thr Ile Thr Cys Val
            20                  25                  30

Pro Glu Ala Phe Leu Glu Asp Glu Arg Pro Ile Gln Thr Met Leu Ile
        35                  40                  45

Lys Thr Ile His Gly Glu Lys Gln Gln Asp Val Tyr Tyr Leu Thr Phe
    50                  55                  60

Lys Val Gln Gly Arg Lys Val Glu Ala Glu Val Leu Ala Ser Pro Tyr
65                  70                  75                  80

Asp Tyr Ile Leu Leu Asn Pro Ser Asp Val Pro Trp Leu Met Lys Lys
                85                  90                  95

Pro Leu Gln Leu Thr Val Leu Val Pro Leu His Glu Tyr Gln Glu Arg
            100                 105                 110

Leu Leu Gln Gln Thr Ala Leu Pro Lys Glu Gln Lys Glu Leu Leu Gln
        115                 120                 125

Lys Leu Phe Leu Lys Tyr Asp Ala Leu Trp Gln His Trp Glu Asn Gln
    130                 135                 140

Val Gly His Arg Arg Ile Lys Pro His Asn Ile Ala Thr Gly Thr Leu
145                 150                 155                 160

Ala Pro Arg Pro Gln Lys Gln Tyr Pro Ile Asn Pro Lys Ala Lys Pro
                165                 170                 175

Ser Ile Gln Ile Val Ile Asp Asp Leu Leu Lys Gln Gly Val Leu Ile
            180                 185                 190

Gln Gln Asn Ser Thr Met Asn Thr Pro Val Tyr Pro Val Pro Lys Pro
        195                 200                 205

Asp Gly Lys Trp Arg Met Val Leu Asp Tyr Arg Glu Val Asn Lys Thr
    210                 215                 220

Ile Pro Leu Ile Ala Ala Gln Asn Gln His Ser Ala Gly Ile Leu Ser
225                 230                 235                 240

Ser Ile Tyr Arg Gly Lys Tyr Lys Thr Thr Leu Asp Leu Thr Asn Gly
                245                 250                 255

Phe Trp Ala His Pro Ile Thr Pro Glu Ser Tyr Trp Leu Thr Ala Phe
            260                 265                 270

Thr Trp Gln Gly Lys Gln Tyr Cys Trp Thr Arg Leu Pro Gln Gly Phe
        275                 280                 285

Leu Asn Ser Pro Ala Leu Phe Thr Ala Asp Val Val Asp Leu Leu Lys
    290                 295                 300

Glu Ile Pro Asn Val Gln Ala Tyr Val Asp Asp Ile Tyr Ile Ser His
305                 310                 315                 320

Asp Asp Pro Gln Glu His Leu Glu Gln Leu Glu Lys Ile Phe Ser Ile
                325                 330                 335

Leu Leu Asn Ala Gly Tyr Val Val Ser Leu Lys Lys Ser Glu Ile Ala
            340                 345                 350
```

```
Gln Arg Glu Val Glu Phe Leu Gly Phe Asn Ile Thr Lys Glu Gly Arg
        355                 360                 365

Gly Leu Thr Asp Thr Phe Lys Gln Lys Leu Leu Asn Ile Thr Pro Pro
        370                 375                 380

Lys Asp Leu Lys Gln Leu Gln Ser Ile Leu Gly Leu Leu Asn Phe Ala
385                 390                 395                 400

Arg Asn Phe Ile Pro Asn Tyr Ser Glu Leu Val Lys Pro Leu Tyr Thr
                405                 410                 415

Ile Val Ala Asn Ala Asn Gly Lys Phe Ile Ser Trp Thr Glu Asp Asn
                420                 425                 430

Ser Asn Gln Leu Gln His Ile Ile Ser Val Leu Asn Gln Ala Asp Asn
        435                 440                 445

Leu Glu Glu Arg Asn Pro Glu Thr Arg Leu Ile Ile Lys Val Asn Ser
        450                 455                 460

Ser Pro Ser Ala Gly Tyr Ile Arg Tyr Tyr Asn Glu Gly Ser Lys Arg
465                 470                 475                 480

Pro Ile Met Tyr Val Asn Tyr Ile Phe Ser Lys Ala Glu Ala Lys Phe
                485                 490                 495

Thr Gln Thr Glu Lys Leu Leu Thr Thr Met His Lys Gly Leu Ile Lys
        500                 505                 510

Ala Met Asp Leu Ala Met Gly Gln Glu Ile Leu Val Tyr Ser Pro Ile
        515                 520                 525

Val Ser Met Thr Lys Ile Gln Arg Thr Pro Leu Pro Glu Arg Lys Ala
530                 535                 540

Leu Pro Val Arg Trp Ile Thr Trp Met Thr Tyr Leu Glu Asp Pro Arg
545                 550                 555                 560

Ile Gln Phe His Tyr Asp Lys Ser Leu Pro Glu Leu Gln Gln Ile Pro
                565                 570                 575

Asn Val Thr Glu Asp Val Ile Ala Lys Thr Lys His Pro Ser Glu Phe
                580                 585                 590

Ala Met Val Phe Tyr Thr Asp Gly Ser Ala Ile Lys His Pro Asp Val
        595                 600                 605

Asn Lys Ser His Ser Ala Gly Met Gly Ile Ala Gln Val Gln Phe Ile
        610                 615                 620

Pro Glu Tyr Lys Ile Val His Gln Trp Ser Ile Pro Leu Gly Asp His
625                 630                 635                 640

Thr Ala Gln Leu Ala Glu Ile Ala Ala Val Glu Phe Ala Cys Lys Lys
                645                 650                 655

Ala Leu Lys Ile Ser Gly Pro Val Leu Ile Val Thr Asp Ser Phe Tyr
                660                 665                 670

Val Ala Glu Ser Ala Asn Lys Glu Leu Pro Tyr Trp Lys Ser Asn Gly
        675                 680                 685

Phe Leu Asn Asn Lys Lys Lys Pro Leu Arg His Val Ser Lys Trp Lys
        690                 695                 700

Ser Ile Ala Glu Cys Leu Gln Leu Lys Pro Asp Ile Ile Ile Met His
705                 710                 715                 720

Glu Lys Gly His Gln Gln Pro Met Thr Thr Leu His Thr Glu Gly Asn
                725                 730                 735

Asn Leu Ala Asp Lys Leu Ala Thr Gln Gly Ser Tyr Val Val His Cys
                740                 745                 750

Asn Thr Thr Pro Ser Leu Asp Ala Glu Leu Asp Gln Leu Leu Gln Gly
                755                 760                 765
```

-continued

```
His Tyr Pro Pro Gly Tyr Pro Lys Gln Tyr Lys Tyr Thr Leu Glu Glu
    770             775                 780

Asn Lys Leu Ile Val Glu Arg Pro Asn Gly Ile Arg Ile Val Pro Pro
785             790                 795                 800

Lys Ala Asp Arg Glu Lys Ile Ile Ser Thr Ala His Asn Ile Ala His
                805                 810                 815

Thr Gly Arg Asp Ala Thr Phe Leu Lys Val Ser Ser Lys Tyr Trp Trp
            820                 825                 830

Pro Asn Leu Arg Lys Asp Val Val Lys Ser Ile Arg Gln Cys Lys Gln
                835                 840                 845

Cys Leu Val Thr Asn Ala Thr Asn Leu Thr Ser Pro Pro Ile Leu Arg
850                 855                 860

Pro Val Lys Pro Leu Lys Pro Phe Asp Lys Phe Tyr Ile Asp Tyr Ile
865                 870                 875                 880

Gly Pro Leu Pro Pro Ser Asn Gly Tyr Leu His Val Leu Val Val Val
                    885                 890                 895

Asp Ser Met Thr Gly Phe Val Trp Leu Tyr Pro Thr Lys Ala Pro Ser
            900                 905                 910

Thr Ser Ala Thr Val Lys Ala Leu Asn Met Leu Thr Ser Ile Ala Ile
            915                 920                 925

Pro Lys Val Leu His Ser Asp Gln Gly Ala Ala Phe Thr Ser Ser Thr
930                 935                 940

Phe Ala Asp Trp Ala Lys Glu Lys Gly Ile Gln Leu Glu Phe Ser Thr
945                 950                 955                 960

Pro Tyr His Pro Gln Ser Ser Gly Lys Val Glu Arg Lys Asn Ser Asp
                965                 970                 975

Ile Lys Arg Leu Leu Thr Lys Leu Leu Ile Gly Arg Pro Ala Lys Trp
            980                 985                 990

Tyr Asp Leu Leu Pro Val Val Gln Leu Ala Leu Asn Asn Ser Tyr Ser
            995                 1000                1005

Pro Ser Ser Lys Tyr Thr Pro His Gln Leu Leu Phe Gly Val Asp Ser
    1010                1015                1020

Asn Thr Pro Phe Ala Asn Ser Asp Thr Leu Asp Leu Ser Arg Glu Glu
1025                1030                1035                1040

Glu Leu Ser Leu Leu Gln Glu Ile Arg Ser Ser Leu His Gln Pro Thr
            1045                1050                1055

Ser Pro Pro Ala Ser Ser Arg Ser Trp Ser Pro Ser Val Gly Gln Leu
            1060                1065                1070

Val Gln Glu Arg Val Ala Arg Pro Ala Ser Leu Arg Pro Arg Trp His
    1075                1080                1085

Lys Pro Thr Ala Ile Leu Glu Val Val Asn Pro Arg Thr Val Ile Ile
    1090                1095                1100

Leu Asp His Leu Gly Asn Arg Arg Thr Val Ser Val Asp Asn Leu Lys
1105                1110                1115                1120

Leu Thr Ala Tyr Gln Asp Asn Gly Thr Ser Asn Asp Ser Gly Thr Met
            1125                1130                1135

Ala Leu Met Glu Glu Asp Glu Ser Ser Thr Ser Ser Thr
            1140                1145
```

<210> SEQ ID NO 21
<211> LENGTH: 193
<212> TYPE: RNA
<213> ORGANISM: Human foamy virus
<220> FEATURE:
<223> OTHER INFORMATION: proviral DNA, R region

<400> SEQUENCE: 21

| gagcucuuca cuacucgcug cgucgagagu guacgagacu cuccagguuu gguaagaaau | 60 |
| auuuuauauu guuauaaugu uacuaugauc cauuaacacu cugcuuauag auuguaaggg | 120 |
| ugauugcaau gcuuucugca uaaaacuuug guuuucuugu uaaucaauaa accgacuuga | 180 |
| uucgagaacc uac | 193 |

<210> SEQ ID NO 22
<211> LENGTH: 153
<212> TYPE: RNA
<213> ORGANISM: Human foamy virus
<220> FEATURE:
<223> OTHER INFORMATION: proviral DNA, T5 region

<400> SEQUENCE: 22

| ucauauauua uugucucuuu uauacuuuau uaaguaaaag gauuuguaua uuagccuugc | 60 |
| uaagggagac aucuagugau auaaguguga acuacacuua ucuuaaauga guaacuccu | 120 |
| uaggauaauc aauauacaaa auccaugac aau | 153 |

<210> SEQ ID NO 23
<211> LENGTH: 294
<212> TYPE: RNA
<213> ORGANISM: Human foamy virus
<220> FEATURE:
<223> OTHER INFORMATION: Cas I

<400> SEQUENCE: 23

| uggcgcccaa cgugggcuc gaauauaagu cggguuuauu uguaaauuau cccuagggac | 60 |
| cuccgagcau agcgggaggc auauaaaagc caauagacac uggcuuaagg aaguaauguu | 120 |
| gaagaauaug aacuugaugu ugaagcucug guuguaauuu uaagagauag aaauauacca | 180 |
| agaaauccuu uacauggaga aguuauaggu cuucgcccuua cugaaggaug guggggacaa | 240 |
| auugagagau uucagauggu acgucuaaua uuacaagaug augauaauga accu | 294 |

<210> SEQ ID NO 24
<211> LENGTH: 807
<212> TYPE: RNA
<213> ORGANISM: Human foamy virus
<220> FEATURE:
<223> OTHER INFORMATION: 5' CAS II

<400> SEQUENCE: 24

| uuacagagac cuuaauuaag gcauggauu uggccuuggg acaagaaaua uuaguuuaua | 60 |
| gucccauugu aucuaugacu aaaauacaaa aaacuccacu accagaaaga aaagcuuuac | 120 |
| ccauuagaug gauaacaugg augacuuauu uagaagaucc aagaaccaa uuucauuag | 180 |
| auaaaaccuu accagaacuu aagcauauuc cagauguaua uacaucuagu cagucuccug | 240 |
| uuaaacaucc uucucaauau gaaggagugu uuuauacuga uggcucggcc aucaaaaguc | 300 |
| cugauccuac aaaaagcaau aaugcuggca ugggaauagu acaugccaca uacaaaaccug | 360 |
| aauaucaagu uuugaaucaa uggucaauac cacuaggauaa ucauacugcu cagauggcug | 420 |
| aaauagcugc aguugaauuu gccguaaaaa agcuuuaaa aauaccuggu ccuguauuag | 480 |
| uuauaacuga uaguuucuau guagcagaaa gugcuaauaa agaauuacca uacuggaaau | 540 |
| cuaauggguu uguuaauaau aagaaaaagc cucuuaaaca uacuccaaa uggaaaucua | 600 |
| uugcugagug uuuuaucuaug aaaccagaca uuacuauuca acaugaaaaa ggcaucagcc | 660 |

```
uacaaauacc aguauucaua cugaaaggca augcccuagc agauaagcuu gccacccaag    720
gaaguuaugu gguuaauugu aauaccaaaa aaccaaaccu ggaugcagag uuggaucaau    780
uauuacaggg ucauuauaua aaaggau                                        807
```

<210> SEQ ID NO 25
<211> LENGTH: 649
<212> TYPE: RNA
<213> ORGANISM: Human foamy virus
<220> FEATURE:
<223> OTHER INFORMATION: 3' CAS II

<400> SEQUENCE: 25

```
uauuggaccu uugccaccuu cacagggaua ccuauaugua uuaguaguug uugauggaau     60
gacaggauuc acuugguuau accccacuaa ggcuccuucu acuagcgcaa cuguuaaauc    120
ucucaaugua cucacuagua uugcaauucc aaaggugauu cacucugauc aaggugcagc    180
auucacuucu ucaaccuuug cugaaugggc aaaggaaaga gguauacauu uggaauucag    240
uacuccuuau caccccaaa gugguaguaa gguggaaagg aaaaauagug auauaaaacg     300
acuuuuaacu aaacugcuag uaggaagacc cacaaagugg uaugaccuau ugccuguugu    360
acaacuugcu uuaaacaaca ccuauagccc uguauuaaaa uauacuccac aucaaucuuu    420
auuugguaua gauucaaaua cuccauuugc aaaucaagau acacuugacu ugaccagaga    480
agaagaacuu ucucuuuuac aggaaauucg uacuucuuua uaccauccau ccaccccucc    540
agccuccucu cguuccuggu cucugguugu uggccaauug guccaggaga ggguggcuag    600 gccugccuucu uugagaccuc guuggcauaa accgucuacu guacuuaag                649
```

<210> SEQ ID NO 26
<211> LENGTH: 9
<212> TYPE: RNA
<213> ORGANISM: Human foamy virus
<220> FEATURE:
<223> OTHER INFORMATION: cppt

<400> SEQUENCE: 26

```
caggagagg                                                              9
```

<210> SEQ ID NO 27
<211> LENGTH: 410
<212> TYPE: RNA
<213> ORGANISM: Artificial sequence
<220> FEATURE:
<223> OTHER INFORMATION: Description of artificial sequence: Synthetic
      polynucleotide
<220> FEATURE:
<223> OTHER INFORMATION: SFFV promoter

<400> SEQUENCE: 27

```
cuagcugcag uaacgccauu uugcaaggca uggaaaaaua ccaaaccaag aauagagaag     60
uucagaucaa gggcggguac augaaaauag cuaacguugg gccaaacagg auaucugcgg    120
ugagcaguuu cggccccggc cggggccaa gaacagaugg ucaccgcagu ucggccccg      180 gcccgaggcc aagaacagau gguccccaga uauggcccaa cccucagcag uuucuuaaga    240
cccaucagau guuccaggc uccccaagg accugaaaug acccgcgcc uuauugaau        300 uaaccaauca gccugcuucu cgcuucuguu cgcgcgcuuc ugcuucccga gcucuauaaa    360
agagcucaca accccucacu cggcgcgcca guccuccgac agacugaguc                410
```

<210> SEQ ID NO 28

```
<211> LENGTH: 219
<212> TYPE: RNA
<213> ORGANISM: Artificial sequence
<220> FEATURE:
<223> OTHER INFORMATION: Description of artificial sequence: Synthetic
      polynucleotide
<220> FEATURE:
<223> OTHER INFORMATION: proviral DNA, deleted T3 sequence

<400> SEQUENCE: 28
ugugguggaa ugccacuaga aacuaggaa aacuaggagg agaguauuac agggaaggaa        60
gugaagaacc ucgugaccca aauacuccug cuccucauag acguaccugg gaugagagac      120
acaagguucu uaaauugucc ucauucgcua cucccucuga cauccaacgc ugggcuacua      180
aagcauugcc uuauggcugg aaaguggguca cuuguacgg                            219

<210> SEQ ID NO 29
<211> LENGTH: 24
<212> TYPE: RNA
<213> ORGANISM: Human foamy virus
<220> FEATURE:
<223> OTHER INFORMATION: 3'PPT

<400> SEQUENCE: 29
agagaggaag uaacgaggag aggg                                              24

<210> SEQ ID NO 30
<211> LENGTH: 2975
<212> TYPE: DNA
<213> ORGANISM: artificial sequence
<220> FEATURE:
<223> OTHER INFORMATION: Description of artificial sequence: Synthetic
      polynucleotide
<220> FEATURE:
<223> OTHER INFORMATION: FV_Env_HCO_Seq

<400> SEQUENCE: 30
ccatggcccc tcccatgacc ctgcagcagt ggatcatctg gaagaagatg aacaaggccc        60
acgaggccct gcagaacacc accaccgtga ccgagcagca gaaagagcag atcatcctgg      120
acatccagaa cgaggaagtg cagcccacca ggcgggacaa gttcagatac ctgctgtaca      180
cctgctgcgc cacctccagc cgggtgctgg cctggatgtt cctggtgtgc atcctgctga      240
tcatcgtgct ggtgtcctgc ttcgtgacca tcagccggat ccagtggaac aaggacatcc      300
aggtgctggg ccccgtgatc gactggaacg tgacccagcg ggccgtgtac cagcccctgc      360
agacccggcg gatcgcccgg tccctgcgga tgcagcaccc cgtgcccaag tacgtggagg      420
tgaacatgac cagcatcccc cagggcgtgt actacgagcc ccaccccgag ccatcgtgg      480 tgaaagaaag agtgctgggc ctgagccaga tcctgatgat caacagcgag aacatcgcca      540
acaacgccaa cctgacccag gaagtgaaga aactgctgac cgagatggtg aacgaagaga      600
tgcagagcct gagcgacgtg atgatcgact tcgagatccc cctgggcgac ccagggacc      660 aggaacagta catccaccgg aagtgctacc aggaatttgc caactgctac ctggtgaagt      720
acaaagagcc caagccctgg cccaaagagg gcctgatcgc cgaccagtgc ccctgcccg      780 gctatcacgc cggcctgacc tacaaccggc agagcatctg ggactactac atcaaggtgg      840
agagcatcag gcccgccaac tggaccacca gagcaagta cggccaggcc cggctgggca      900
gcttctacat cccagcagc ctgcggcaga tcaacgtgag ccacgtgctg ttctgcagcg      960
accagctgta cagcaagtgg tacaacatcg agaacaccat cgagcagaac gagcggttcc     1020
tgctgaacaa gctgaataac ctgaccagcg gcaccagcgt gctgaagaag agagccctgc     1080
```

-continued

```
ccaaggactg gtccagccag ggcaagaacg ccctgttccg ggagatcaat gtgctggaca      1140
tctgcagcaa gcccgagagc gtgatcctgc tgaataccag ctactacagc ttcagcctgt      1200
gggagggcga ctgcaacttc accaaggaca tgatcagcca gctggtgccc gagtgcgacg      1260
gcttctacaa caactccaag tggatgcaca tgcaccccta cgcctgccgg ttctggcgga      1320
gcaagaacga gaaagaggaa accaagtgcc gggacggcga gaccaagcgg tgcctgtact      1380
accccctgtg ggacagccct gagagcacct acgacttcgg ctacctggcc taccagaaga      1440
acttccccag ccccatctgc atcgaacagc agaagatccg ggaccaggac tacgaggtgt      1500
acagcctgta ccaggaatgc aagatcgcca gcaaggccta cggcatcgac accgtgctgt      1560
tcagcctgaa gaatttcctg aactacaccg gcaccccgt gaacgagatg cccaacgcca      1620
gggccttcgt gggcctgatt gaccccaagt tccccccag ctaccccaac gtgacccggg      1680
agcactacac cagctgcaac aaccggaagc ggcggagcgt ggacaacaac tacgccaagc      1740
tgcggagcat gggctacgct ctgacaggcg ccgtgcagac cctgtcccag atcagcgaca      1800
tcaacgacga gaacctgcag cagggcatct acctgctgcg ggaccacgtg atcaccctga      1860
tggaagccac cctgcacgac atcagcgtga tggaaggcat gttcgccgtg cagcacctgc      1920
acacccacct gaatcacctg aaaaccatgc tgctggaacg gcgcatcgac tggacctaca      1980
tgagcagcac ctggctgcag cagcagctgc agaaaagcga cgacgagatg aaggtgatca      2040
agcggatcgc cagatctctg gtgtactacg tgaagcagac ccacagcagc cccaccgcca      2100
ccgcctggga gatcggcctg tactatgagc tggtgatccc caagcacatc tacctgaaca      2160
actggaatgt ggtgaacatc ggccacctgg tgaaaagcgc cggacagctg acccacgtga      2220
ccatcgccca cccctacgag atcatcaaca agaatgcgt ggagaccatc tatctgcacc      2280
tggaagattg cacccggcag gactacgtga tctgcgacgt ggtgaagatc gtgcagccct      2340
gcggcaacag cagcgacacc agcgactgcc ccgtgtgggc cgaggccgtg aaagaaccct      2400
tcgtgcaggt gaacccctg aagaacggct cctacctggt gctggccagc agcaccgact      2460
gccagatccc ccctacgtg cccagcatcg tgaccgtgaa tgagaccacc tcctgcttcg      2520
gcctggactt caagcggccc ctggtggccg aggaaagact gagcttcgag ccccggctgc      2580
ccaacctgca gctgaggctg ccccaccctgg tgggcatcat cgccaagatc aagggcatca      2640
agatcgaggt gaccagcagc ggcgagagca tcaaagaaca gatcgagcgg gccaaggccg      2700
agctgctgcg gctggatatc cacgagggcg acacacccgc ctggatccag cagctggccg      2760
ccgccaccaa ggacgtgtgg cccgctgcag ccagcgccct gcagggcatc ggcaactttc      2820
tgagcggcac cgcccagggc atcttcggca ccgccttctc cctgctgggc tacctgaagc      2880
ccatcctgat cggcgtgggc gtgattctgc tggtgattct gatcttcaag atcgtgagct      2940
ggatccccac caagaaaaag aaccagtgac tcgag                                 2975
```

<210> SEQ ID NO 31
<211> LENGTH: 2967
<212> TYPE: RNA
<213> ORGANISM: artificial sequence
<220> FEATURE:
<223> OTHER INFORMATION: Description of artificial sequence: Synthetic
    polynucleotide
<220> FEATURE:
<223> OTHER INFORMATION: FV_Env_HCO_Seq

<400> SEQUENCE: 31

```
auggccccuc ccaugacccu gcagcagugg aucaucugga agaagaugaa caaggcccac      60
```

```
gaggcccugc agaacaccac caccgugacc gagcagcaga aagagcagau cauccuggac    120
auccagaacg aggaagugca gcccaccagg cgggacaagu ucagauaccu gcuuacacc     180 ugcugcgcca ccuccagccg ggugcuggcc uggauguucc gguguugcau ccugcugauc    240
aucgugcugg uguccugcuu cgugaccauc agccggaucc aguggaacaa ggacauccag    300
gugcugggcc ccgugaucga cuggaacgug acccagcggg ccguguacca gccccugcag    360
acccggcgga ucgccgguc ccugcggaug cagcaccccg ugcccaagua cguggaggug     420
aacaugacca gcauccccca gggcguguac uacgagcccc accccgagcc caucguggug    480
aaagaaagag ugcugggccu gagccagauc cugaugauca cagcgagaa caucgccaac     540 aacgccaacc ugacccagga agugaagaaa cugcugaccg agauggugaa cgaagagaug    600
cagagccuga cgacgugau gaucgacuuc gagaucccc ugggcgaccc cagggaccag      660
gaacaguaca uccaccggaa gugcuaccag gaauuugcca cugcuaccu ggugaaguac     720 aaagagccca agcccuggcc caaagagggc cugaucgccg accagugccc ccugcccggc    780
uaucacgccg ccugaccua caaccggcag agcaucuggg acuacacau caagguggag      840 agcaucaggc cgccaacug gaccaccaag agcaaguacg ccaggcccg cugggcagc       900 uucuacaucc ccagcagccu gcggcagauc aacgugagcc acgugcuguu cugcagcgac    960
cagcuguaca gcaagggua caacaucgag aacaccaucg agcagaacga gcgguuccug     1020
cugaacaagc ugaauaaccu gaccagcggc accagcgugc ugaagaagag agcccugccc    1080
aaggacuggu ccagccaggg caagaacgcc cuguuccggg agaucaaugu gcuggacauc    1140
ugcagcaagc ccgagagcgu gauccugcug aauaccagcu acuacagcuu cagccugugg    1200
gagggcgacu gcaacuucac caaggacaug aucagccagc uggugcccga gucgacggc     1260 uucuacaaca acuccaagug gaugcacaug caccccuacg ccugccgguu cuggcggagc    1320
aagaacgaga aagaggaaac caagugccgg gacggcgaga ccaagcggug ccuguacuac    1380 ccccugugg acagcccuga gagcaccuac gacuucggcu accuggccua ccagaagaac    1440
uuccccagcc ccaucugcau cgaacagcag aagauccggg accaggacua cgagguguac     1500
agccuguacc aggaaugcaa gaucgccagc aaggccuacg gcaucgacac cgugcuguuc    1560
agccugaaga uuuccugaa cuacaccggc accccgugga acgagaugcc caacgccagg    1620
gccuucgugg ccugauuga ccccaaguuc ccccccagcu accccaacgu gacccgggag     1680
cacuacacca gcugcaacaa ccggaagcgg cggagcgugg acaacaacua cgccaagcug    1740
cggagcaugg cuacgcucu gacaggcgcc gugcagaccc uguccagau cagcgacauc      1800 aacgacgaga accugcagca gggcaucuac cugcugcggg accacgugau cacccugaug    1860
gaagccaccc ugcacgacau cagcgugaug gaaggcaugu cgccgugca gcaccugcac     1920 acccaccuga ucaccugaa aaccaugcug cuggaacggc gcaucgacug gacuacaug     1980 agcagcaccu ggcugcagca gcagcugcag aaaagcgacg acgagaugaa ggugaucaag    2040
cggaucgcca gaucucuggu guacuacgug aagcagaccc acagcagccc caccgccacc    2100
gccugggaga ucggccugua cauagaucug gaucccca agcacaucua ccugaacaac      2160
uggaaugugg ugaacaucgg ccaccuggug aaaagcgccg acagcugac ccacgugacc    2220 aucgccoacc ccuacgagau caucaacaaa gaaugcgugg agaccaucua ucugcaccug    2280
gaagauugca cccggcagga cuacgugauc ugcgacgugg ugaagaucgu gcagcccugc    2340
ggcaacagca gcgacaccag cgacugcccc guguggggccg aggccgugaa agaacccuuc    2400
```

```
gugcaggtga accccctgaa gaacggctcc taccuggugc uggccagcag caccgacugc    2460
cagauccccc ccuacgugcc cagcaucgug accgugaaug agaccaccuc cugcuucggc    2520
cuggacuuca gcggccccu gguggccgag gaaagacuga gcuucgagcc ccggcugccc    2580
aaccugcagc ugaggcugcc ccaccuggug ggcaucaucg ccaagaucaa gggcaucaag    2640
aucgaggtga ccagcagcgg cgagagcauc aaagaacaga ucgagcgggc caaggccgag    2700
cugcugcggc uggauaucca cgagggcgac acacccgccu ggauccagca gcuggccgcc    2760
gccaccaagg acgugugggcc cgcugcagcc agcgcccugc agggcaucgg caacuuucug    2820
agcggcaccg cccagggcau cuucggcacc gccuucuccc ugcugggcua ccugaagccc    2880
auccugaucg gcgugggcgu gauucugcug gugauucuga ucuucaagau cgugagcugg    2940 aucccccacca agaaaaagaa ccaguga                                       2967
```

<210> SEQ ID NO 32
<211> LENGTH: 988
<212> TYPE: PRT
<213> ORGANISM: artificial sequence
<220> FEATURE:
<223> OTHER INFORMATION: Description of artificial sequence: Synthetic
      polypeptide
<220> FEATURE:
<223> OTHER INFORMATION: FV_Env_HCO_Seq

<400> SEQUENCE: 32

```
Met Ala Pro Pro Met Thr Leu Gln Gln Trp Ile Ile Trp Lys Lys Met
1               5                   10                  15

Asn Lys Ala His Glu Ala Leu Gln Asn Thr Thr Thr Val Thr Glu Gln
            20                  25                  30

Gln Lys Glu Gln Ile Ile Leu Asp Ile Gln Asn Glu Glu Val Gln Pro
        35                  40                  45

Thr Arg Arg Asp Lys Phe Arg Tyr Leu Leu Tyr Thr Cys Cys Ala Thr
    50                  55                  60

Ser Ser Arg Val Leu Ala Trp Met Phe Leu Val Cys Ile Leu Leu Ile
65                  70                  75                  80

Ile Val Leu Val Ser Cys Phe Val Thr Ile Ser Arg Ile Gln Trp Asn
                85                  90                  95

Lys Asp Ile Gln Val Leu Gly Pro Val Ile Asp Trp Asn Val Thr Gln
            100                 105                 110

Arg Ala Val Tyr Gln Pro Leu Gln Thr Arg Arg Ile Ala Arg Ser Leu
        115                 120                 125

Arg Met Gln His Pro Val Pro Lys Tyr Val Glu Val Asn Met Thr Ser
    130                 135                 140

Ile Pro Gln Gly Val Tyr Tyr Glu Pro His Pro Glu Pro Ile Val Val
145                 150                 155                 160

Lys Glu Arg Val Leu Gly Leu Ser Gln Ile Leu Met Ile Asn Ser Glu
                165                 170                 175

Asn Ile Ala Asn Asn Ala Asn Leu Thr Gln Glu Val Lys Lys Leu Leu
            180                 185                 190

Thr Glu Met Val Asn Glu Glu Met Gln Ser Leu Ser Asp Val Met Ile
        195                 200                 205

Asp Phe Glu Ile Pro Leu Gly Asp Pro Arg Asp Gln Glu Gln Tyr Ile
    210                 215                 220

His Arg Lys Cys Tyr Gln Glu Phe Ala Asn Cys Tyr Leu Val Lys Tyr
225                 230                 235                 240

Lys Glu Pro Lys Pro Trp Pro Lys Glu Gly Leu Ile Ala Asp Gln Cys
```

```
                    245                 250                 255
Pro Leu Pro Gly Tyr His Ala Gly Leu Thr Tyr Asn Arg Gln Ser Ile
                260                 265                 270
Trp Asp Tyr Tyr Ile Lys Val Glu Ser Ile Arg Pro Ala Asn Trp Thr
            275                 280                 285
Thr Lys Ser Lys Tyr Gly Gln Ala Arg Leu Gly Ser Phe Tyr Ile Pro
        290                 295                 300
Ser Ser Leu Arg Gln Ile Asn Val Ser His Val Leu Phe Cys Ser Asp
305                 310                 315                 320
Gln Leu Tyr Ser Lys Trp Tyr Asn Ile Glu Asn Thr Ile Glu Gln Asn
                325                 330                 335
Glu Arg Phe Leu Leu Asn Lys Leu Asn Asn Leu Thr Ser Gly Thr Ser
                340                 345                 350
Val Leu Lys Lys Arg Ala Leu Pro Lys Asp Trp Ser Ser Gln Gly Lys
                355                 360                 365
Asn Ala Leu Phe Arg Glu Ile Asn Val Leu Asp Ile Cys Ser Lys Pro
            370                 375                 380
Glu Ser Val Ile Leu Leu Asn Thr Ser Tyr Tyr Ser Phe Ser Leu Trp
385                 390                 395                 400
Glu Gly Asp Cys Asn Phe Thr Lys Asp Met Ile Ser Gln Leu Val Pro
                    405                 410                 415
Glu Cys Asp Gly Phe Tyr Asn Asn Ser Lys Trp Met His Met His Pro
                420                 425                 430
Tyr Ala Cys Arg Phe Trp Arg Ser Lys Asn Glu Lys Glu Glu Thr Lys
            435                 440                 445
Cys Arg Asp Gly Glu Thr Lys Arg Cys Leu Tyr Tyr Pro Leu Trp Asp
450                 455                 460
Ser Pro Glu Ser Thr Tyr Asp Phe Gly Tyr Leu Ala Tyr Gln Lys Asn
465                 470                 475                 480
Phe Pro Ser Pro Ile Cys Ile Glu Gln Gln Lys Ile Arg Asp Gln Asp
                485                 490                 495
Tyr Glu Val Tyr Ser Leu Tyr Gln Glu Cys Lys Ile Ala Ser Lys Ala
                500                 505                 510
Tyr Gly Ile Asp Thr Val Leu Phe Ser Leu Lys Asn Phe Leu Asn Tyr
            515                 520                 525
Thr Gly Thr Pro Val Asn Glu Met Pro Asn Ala Arg Ala Phe Val Gly
        530                 535                 540
Leu Ile Asp Pro Lys Phe Pro Pro Ser Tyr Pro Asn Val Thr Arg Glu
545                 550                 555                 560
His Tyr Thr Ser Cys Asn Asn Arg Lys Arg Arg Ser Val Asp Asn Asn
                565                 570                 575
Tyr Ala Lys Leu Arg Ser Met Gly Tyr Ala Leu Thr Gly Ala Val Gln
                580                 585                 590
Thr Leu Ser Gln Ile Ser Asp Ile Asn Asp Glu Asn Leu Gln Gln Gly
                595                 600                 605
Ile Tyr Leu Leu Arg Asp His Val Ile Thr Leu Met Glu Ala Thr Leu
        610                 615                 620
His Asp Ile Ser Val Met Glu Gly Met Phe Ala Val Gln His Leu His
625                 630                 635                 640
Thr His Leu Asn His Leu Lys Thr Met Leu Leu Glu Arg Arg Ile Asp
                645                 650                 655
Trp Thr Tyr Met Ser Ser Thr Trp Leu Gln Gln Gln Leu Gln Lys Ser
                660                 665                 670
```

```
Asp Asp Glu Met Lys Val Ile Lys Arg Ile Ala Arg Ser Leu Val Tyr
            675                 680                 685

Tyr Val Lys Gln Thr His Ser Ser Pro Thr Ala Thr Ala Trp Glu Ile
        690                 695                 700

Gly Leu Tyr Tyr Glu Leu Val Ile Pro Lys His Ile Tyr Leu Asn Asn
705                 710                 715                 720

Trp Asn Val Val Asn Ile Gly His Leu Val Lys Ser Ala Gly Gln Leu
                725                 730                 735

Thr His Val Thr Ile Ala His Pro Tyr Glu Ile Ile Asn Lys Glu Cys
            740                 745                 750

Val Glu Thr Ile Tyr Leu His Leu Glu Asp Cys Thr Arg Gln Asp Tyr
        755                 760                 765

Val Ile Cys Asp Val Val Lys Ile Val Gln Pro Cys Gly Asn Ser Ser
770                 775                 780

Asp Thr Ser Asp Cys Pro Val Trp Ala Glu Ala Val Lys Glu Pro Phe
785                 790                 795                 800

Val Gln Val Asn Pro Leu Lys Asn Gly Ser Tyr Leu Val Leu Ala Ser
                805                 810                 815

Ser Thr Asp Cys Gln Ile Pro Pro Tyr Val Pro Ser Ile Val Thr Val
            820                 825                 830

Asn Glu Thr Thr Ser Cys Phe Gly Leu Asp Phe Lys Arg Pro Leu Val
        835                 840                 845

Ala Glu Glu Arg Leu Ser Phe Glu Pro Arg Leu Pro Asn Leu Gln Leu
850                 855                 860

Arg Leu Pro His Leu Val Gly Ile Ile Ala Lys Ile Lys Gly Ile Lys
865                 870                 875                 880

Ile Glu Val Thr Ser Ser Gly Glu Ser Ile Lys Glu Gln Ile Glu Arg
                885                 890                 895

Ala Lys Ala Glu Leu Leu Arg Leu Asp Ile His Glu Gly Asp Thr Pro
            900                 905                 910

Ala Trp Ile Gln Gln Leu Ala Ala Ala Thr Lys Asp Val Trp Pro Ala
        915                 920                 925

Ala Ala Ser Ala Leu Gln Gly Ile Gly Asn Phe Leu Ser Gly Thr Ala
930                 935                 940

Gln Gly Ile Phe Gly Thr Ala Phe Ser Leu Leu Gly Tyr Leu Lys Pro
945                 950                 955                 960

Ile Leu Ile Gly Val Gly Val Ile Leu Leu Val Ile Leu Ile Phe Lys
                965                 970                 975

Ile Val Ser Trp Ile Pro Thr Lys Lys Lys Asn Gln
            980                 985

<210> SEQ ID NO 33
<211> LENGTH: 988
<212> TYPE: PRT
<213> ORGANISM: Human foamy virus
<220> FEATURE:
<223> OTHER INFORMATION: Env (GenBank: CAA69000.1)

<400> SEQUENCE: 33

Met Ala Pro Pro Met Thr Leu Gln Gln Trp Ile Ile Trp Lys Lys Met
1               5                   10                  15

Asn Lys Ala His Glu Ala Leu Gln Asn Thr Thr Thr Val Thr Glu Gln
            20                  25                  30

Gln Lys Glu Gln Ile Ile Leu Asp Ile Gln Asn Glu Glu Val Gln Pro
        35                  40                  45
```

```
Thr Arg Arg Asp Lys Phe Arg Tyr Leu Leu Tyr Thr Cys Cys Ala Thr
    50              55              60
Ser Ser Arg Val Leu Ala Trp Met Phe Leu Val Cys Ile Leu Leu Ile
65              70              75              80
Ile Val Leu Val Ser Cys Phe Val Thr Ile Ser Arg Ile Gln Trp Asn
                85              90              95
Lys Asp Ile Gln Val Leu Gly Pro Val Ile Asp Trp Asn Val Thr Gln
            100             105             110
Arg Ala Val Tyr Gln Pro Leu Gln Thr Arg Arg Ile Ala Arg Ser Leu
        115             120             125
Arg Met Gln His Pro Val Pro Lys Tyr Val Glu Val Asn Met Thr Ser
    130             135             140
Ile Pro Gln Gly Val Tyr Tyr Glu Pro His Pro Glu Pro Ile Val Val
145             150             155             160
Lys Glu Arg Val Leu Gly Leu Ser Gln Ile Leu Met Ile Asn Ser Glu
                165             170             175
Asn Ile Ala Asn Asn Ala Asn Leu Thr Gln Glu Val Lys Lys Leu Leu
            180             185             190
Thr Glu Met Val Asn Glu Met Gln Ser Leu Ser Asp Val Met Ile
    195             200             205
Asp Phe Glu Ile Pro Leu Gly Asp Pro Arg Asp Gln Glu Gln Tyr Ile
    210             215             220
His Arg Lys Cys Tyr Gln Glu Phe Ala Asn Cys Tyr Leu Val Lys Tyr
225             230             235             240
Lys Glu Pro Lys Pro Trp Pro Lys Glu Gly Leu Ile Ala Asp Gln Cys
                245             250             255
Pro Leu Pro Gly Tyr His Ala Gly Leu Thr Tyr Asn Arg Gln Ser Ile
            260             265             270
Trp Asp Tyr Tyr Ile Lys Val Glu Ser Ile Arg Pro Ala Asn Trp Thr
    275             280             285
Thr Lys Ser Lys Tyr Gly Gln Ala Arg Leu Gly Ser Phe Tyr Ile Pro
    290             295             300
Ser Ser Leu Arg Gln Ile Asn Val Ser His Val Leu Phe Cys Ser Asp
305             310             315             320
Gln Leu Tyr Ser Lys Trp Tyr Asn Ile Glu Asn Thr Ile Glu Gln Asn
                325             330             335
Glu Arg Phe Leu Leu Asn Lys Leu Asn Asn Leu Thr Ser Gly Thr Ser
            340             345             350
Val Leu Lys Lys Arg Ala Leu Pro Lys Asp Trp Ser Ser Gln Gly Lys
        355             360             365
Asn Ala Leu Phe Arg Glu Ile Asn Val Leu Asp Ile Cys Ser Lys Pro
    370             375             380
Glu Ser Val Ile Leu Leu Asn Thr Ser Tyr Tyr Ser Phe Ser Leu Trp
385             390             395             400
Glu Gly Asp Cys Asn Phe Thr Lys Asp Met Ile Ser Gln Leu Val Pro
                405             410             415
Glu Cys Asp Gly Phe Tyr Asn Asn Ser Lys Trp Met His Met His Pro
            420             425             430
Tyr Ala Cys Arg Phe Trp Arg Ser Lys Asn Glu Lys Glu Thr Lys
        435             440             445
Cys Arg Asp Gly Glu Thr Lys Arg Cys Leu Tyr Tyr Pro Leu Trp Asp
    450             455             460
```

```
Ser Pro Glu Ser Thr Tyr Asp Phe Gly Tyr Leu Ala Tyr Gln Lys Asn
465                 470                 475                 480

Phe Pro Ser Pro Ile Cys Ile Glu Gln Gln Lys Ile Arg Asp Gln Asp
            485                 490                 495

Tyr Glu Val Tyr Ser Leu Tyr Gln Glu Arg Lys Ile Ala Ser Lys Ala
        500                 505                 510

Tyr Gly Ile Asp Thr Val Leu Phe Ser Leu Lys Asn Phe Leu Asn Tyr
    515                 520                 525

Thr Gly Thr Pro Val Asn Glu Met Pro Asn Ala Arg Ala Phe Val Gly
530                 535                 540

Leu Ile Asp Pro Lys Phe Pro Pro Ser Tyr Pro Asn Val Thr Arg Glu
545                 550                 555                 560

His Tyr Thr Ser Cys Asn Asn Arg Lys Arg Arg Ser Val Asp Asn Asn
                565                 570                 575

Tyr Ala Lys Leu Arg Ser Met Gly Tyr Ala Leu Thr Gly Ala Val Gln
            580                 585                 590

Thr Leu Ser Gln Ile Ser Asp Ile Asn Asp Glu Asn Leu Gln Gln Gly
        595                 600                 605

Ile Tyr Leu Leu Arg Asp His Val Ile Thr Leu Met Glu Ala Thr Leu
    610                 615                 620

His Asp Ile Ser Val Met Glu Gly Met Phe Ala Val Gln His Leu His
625                 630                 635                 640

Thr His Leu Asn His Leu Lys Thr Met Leu Leu Glu Arg Arg Ile Asp
                645                 650                 655

Trp Thr Tyr Met Ser Ser Thr Trp Leu Gln Gln Leu Gln Lys Ser
            660                 665                 670

Asp Asp Glu Met Lys Val Ile Lys Arg Ile Ala Arg Ser Leu Val Tyr
            675                 680                 685

Tyr Val Lys Gln Thr His Ser Ser Pro Thr Ala Thr Ala Trp Glu Ile
    690                 695                 700

Gly Leu Tyr Tyr Glu Leu Val Ile Pro Lys His Ile Tyr Leu Asn Asn
705                 710                 715                 720

Trp Asn Val Val Asn Ile Gly His Leu Val Lys Ser Ala Gly Gln Leu
                725                 730                 735

Thr His Val Thr Ile Ala His Pro Tyr Glu Ile Ile Asn Lys Glu Cys
            740                 745                 750

Val Glu Thr Ile Tyr Leu His Leu Glu Asp Cys Thr Arg Gln Asp Tyr
        755                 760                 765

Val Ile Cys Asp Val Val Lys Ile Val Gln Pro Cys Gly Asn Ser Ser
    770                 775                 780

Asp Thr Ser Asp Cys Pro Val Trp Ala Glu Ala Val Lys Glu Pro Phe
785                 790                 795                 800

Val Gln Val Asn Pro Leu Lys Asn Gly Ser Tyr Leu Val Leu Ala Ser
                805                 810                 815

Ser Thr Asp Cys Gln Ile Pro Pro Tyr Val Pro Ser Ile Val Thr Val
            820                 825                 830

Asn Glu Thr Thr Ser Cys Phe Gly Leu Asp Phe Lys Arg Pro Leu Val
        835                 840                 845

Ala Glu Glu Arg Leu Ser Phe Glu Pro Arg Leu Pro Asn Leu Gln Leu
    850                 855                 860

Arg Leu Pro His Leu Val Gly Ile Ile Ala Lys Ile Lys Gly Ile Lys
865                 870                 875                 880

Ile Glu Val Thr Ser Ser Gly Glu Ser Ile Lys Glu Gln Ile Glu Arg
```

-continued

```
                885                 890                 895
Ala Lys Ala Glu Leu Leu Arg Leu Asp Ile His Glu Gly Asp Thr Pro
            900                 905                 910
Ala Trp Ile Gln Gln Leu Ala Ala Thr Lys Asp Val Trp Pro Ala
            915                 920                 925
Ala Ala Ser Ala Leu Gln Gly Ile Gly Asn Phe Leu Ser Gly Thr Ala
            930                 935                 940
Gln Gly Ile Phe Gly Thr Ala Phe Ser Leu Leu Gly Tyr Leu Lys Pro
945                 950                 955                 960
Ile Leu Ile Gly Val Gly Val Ile Leu Leu Val Ile Leu Ile Phe Lys
                965                 970                 975
Ile Val Ser Trp Ile Pro Thr Lys Lys Lys Asn Gln
                980                 985
```

<210> SEQ ID NO 34
<211> LENGTH: 989
<212> TYPE: PRT
<213> ORGANISM: Macaque simian foamy virus
<220> FEATURE:
<223> OTHER INFORMATION: Env(NCBI Reference: YP_001961123.1)

<400> SEQUENCE: 34

```
Met Ala Pro Pro Met Thr Leu Glu Gln Trp Leu Leu Trp Lys Lys Met
1               5                   10                  15
Ser Gln Ala His Gln Ala Leu Glu Asn Val Thr Thr Leu Thr Glu Glu
                20                  25                  30
Gln Lys Gln Gln Val Ile Asp Ile Gln His Glu Asp Val Val Pro
            35                  40                  45
Thr Arg Met Asp Lys Leu Lys Tyr Leu Ala Tyr Ser Cys Cys Ala Thr
    50                  55                  60
Ser Thr Arg Val Leu Cys Trp Ile Val Leu Val Cys Val Leu Leu Leu
65                  70                  75                  80
Val Val Phe Ile Ser Cys Phe Val Thr Met Ser Arg Ile Gln Trp Asn
                85                  90                  95
Lys Asp Ile Ala Val Phe Gly Pro Val Ile Asp Trp Asn Val Ser Gln
            100                 105                 110
Gln Ala Val Ile Gln Gln Ile Arg Ala Lys Arg Leu Ala Arg Ser Ile
        115                 120                 125
Arg Val Glu His Ala Thr Glu Thr Tyr Val Glu Val Asn Met Thr Ser
    130                 135                 140
Ile Pro Gln Gly Val Leu Tyr Val Pro His Pro Glu Pro Ile Ile Leu
145                 150                 155                 160
Lys Glu Arg Ile Leu Gly Leu Ser Gln Val Met Met Ile Asn Ser Glu
                165                 170                 175
Asn Ile Ala Asn Thr Ala Asn Leu Thr Gln Glu Thr Lys Val Leu Leu
            180                 185                 190
Ala Asp Met Ile Asn Glu Glu Met Asn Asp Leu Ala Asn Gln Met Ile
        195                 200                 205
Asp Phe Glu Ile Pro Leu Gly Asp Pro Arg Asp Gln Lys Gln Tyr Gln
    210                 215                 220
His Gln Lys Cys Phe Gln Glu Phe Ala His Cys Tyr Leu Val Lys Tyr
225                 230                 235                 240
Lys Thr Thr Lys Gly Trp Pro Ser Ser Thr Val Ile Ala Asp Gln Cys
                245                 250                 255
Pro Leu Pro Gly Asn His Pro Thr Val Gln Tyr Ala His Gln Asn Ile
```

```
            260                 265                 270
Trp Asp Tyr Tyr Val Pro Phe Glu Gln Ile Arg Pro Glu Gly Trp Asn
        275                 280                 285

Ser Lys Ser Tyr Tyr Glu Asp Ala Arg Ile Gly Gly Phe Tyr Ile Pro
        290                 295                 300

Lys Trp Leu Arg Asn Asn Ser Tyr Thr His Val Leu Phe Cys Ser Asp
305                 310                 315                 320

Gln Ile Tyr Gly Lys Trp Tyr Asn Ile Asp Leu Thr Ala Gln Glu Arg
                325                 330                 335

Glu Asn Leu Leu Val Arg Lys Leu Ile Asn Leu Ala Lys Gly Asn Ser
            340                 345                 350

Ser Gln Leu Lys Asp Arg Ala Met Pro Ala Glu Trp Asp Lys Gln Gly
        355                 360                 365

Lys Ala Asp Leu Phe Arg Gln Ile Asn Thr Leu Asp Val Cys Asn Arg
        370                 375                 380

Pro Glu Met Val Phe Leu Leu Asn Ser Ser Tyr Tyr Glu Phe Ser Leu
385                 390                 395                 400

Trp Glu Gly Asp Cys Gly Phe Thr Arg Gln Asn Val Thr Gln Ala Asn
                405                 410                 415

Ser Leu Cys Lys Asp Phe Tyr Asn Asn Ser Lys Trp Gln Lys Leu His
                420                 425                 430

Pro Tyr Ser Cys Arg Phe Trp Arg Tyr Lys Gln Glu Lys Glu Glu Thr
        435                 440                 445

Lys Cys Ser Asn Gly Glu Lys Lys Cys Leu Tyr Tyr Pro Gln Trp
        450                 455                 460

Asp Thr Pro Glu Ala Leu Tyr Asp Phe Gly Phe Leu Ala Tyr Leu Asn
465                 470                 475                 480

Ser Phe Pro Ser Pro Ile Cys Ile Lys Asn Gln Thr Ile Arg Glu Pro
                485                 490                 495

Glu Tyr Lys Ile Ser Ser Leu Tyr Leu Glu Cys Met Asn Ala Ser Asp
                500                 505                 510

Arg His Gly Ile Asp Ser Ala Leu Leu Ala Leu Lys Thr Phe Leu Asn
        515                 520                 525

Phe Thr Gly Gln Ser Val Asn Glu Met Pro Leu Ala Arg Ala Phe Val
        530                 535                 540

Gly Leu Thr Asp Pro Lys Phe Pro Pro Thr Tyr Pro Asn Ile Thr Arg
545                 550                 555                 560

Glu Ser Ser Gly Cys Asn Asn Asn Lys Arg Lys Arg Arg Ser Val Asn
                565                 570                 575

Asn Tyr Glu Arg Leu Arg Ser Met Gly Tyr Ala Leu Thr Gly Ala Val
            580                 585                 590

Gln Thr Leu Ser Gln Ile Ser Asp Ile Asn Asp Glu Arg Leu Gln His
        595                 600                 605

Gly Val Tyr Leu Leu Arg Asp His Val Val Thr Leu Met Glu Ala Ala
        610                 615                 620

Leu His Asp Val Ser Ile Met Glu Gly Met Leu Ala Ile Gln His Val
625                 630                 635                 640

His Thr His Leu Asn His Leu Lys Thr Met Leu Leu Met Arg Lys Ile
                645                 650                 655

Asp Trp Thr Phe Ile Arg Ser Asp Trp Ile Gln Gln Gln Leu Gln Lys
                660                 665                 670

Thr Asp Asp Glu Met Lys Leu Ile Arg Arg Thr Ala Arg Ser Leu Val
        675                 680                 685
```

Tyr Tyr Val Thr Gln Thr Ser Ser Ser Pro Thr Ala Thr Ser Trp Glu
            690                 695                 700

Ile Gly Ile Tyr Tyr Glu Ile Val Ile Pro Lys His Ile Tyr Leu Asn
705                 710                 715                 720

Asn Trp Gln Val Ile Asn Val Gly His Leu Leu Glu Ser Ala Gly His
                725                 730                 735

Leu Thr His Val Lys Val Lys His Pro Tyr Glu Ile Ile Asn Lys Glu
            740                 745                 750

Cys Ser Asp Thr Gln Tyr Leu His Leu Glu Glu Cys Ile Arg Glu Asp
        755                 760                 765

Tyr Val Ile Cys Asp Ile Val Gln Ile Val Gln Pro Cys Gly Asn Ala
770                 775                 780

Thr Glu Leu Ser Asp Cys Pro Val Thr Ala Leu Lys Val Lys Thr Pro
785                 790                 795                 800

Tyr Ile Gln Val Ser Pro Leu Lys Asn Gly Ser Tyr Leu Val Leu Ser
                805                 810                 815

Ser Thr Lys Asp Cys Ser Ile Pro Ala Tyr Val Pro Ser Val Val Thr
            820                 825                 830

Val Asn Glu Thr Val Lys Cys Phe Gly Val Glu Phe His Lys Pro Leu
        835                 840                 845

Tyr Ala Glu Thr Lys Thr Ser Tyr Glu Pro Gln Val Pro His Leu Lys
850                 855                 860

Leu Arg Leu Pro His Leu Thr Gly Ile Ile Ala Ser Leu Gln Ser Leu
865                 870                 875                 880

Glu Ile Glu Val Thr Ser Thr Gln Glu Asn Ile Lys Asp Gln Ile Glu
                885                 890                 895

Arg Ala Lys Ala Gln Leu Leu Arg Leu Asp Ile His Glu Gly Asp Phe
            900                 905                 910

Pro Asp Trp Leu Lys Gln Val Ala Ser Ala Thr Arg Asp Val Trp Pro
        915                 920                 925

Ala Ala Ala Ser Phe Ile Gln Gly Val Gly Asn Phe Leu Ser Asn Thr
930                 935                 940

Ala Gln Gly Ile Phe Gly Ser Ala Val Ser Leu Leu Phe Tyr Ala Lys
945                 950                 955                 960

Pro Ile Leu Ile Gly Ile Gly Val Ile Leu Leu Ile Ala Leu Leu Phe
                965                 970                 975

Lys Ile Ile Ser Trp Leu Pro Gly Lys Pro Lys Lys Asn
            980                 985

<210> SEQ ID NO 35
<211> LENGTH: 982
<212> TYPE: PRT
<213> ORGANISM: African green monkey simian foamy virus
<220> FEATURE:
<223> OTHER INFORMATION: Env (NCBI Reference: YP_001956723.2)

<400> SEQUENCE: 35

Met Ala Pro Pro Met Asn Leu Gln Gln Trp Leu Leu Trp Lys Lys Met
1               5                   10                  15

Asn Glu Thr His Leu Ala Leu Glu Asn Ile Ser Ser Leu Thr Glu Glu
            20                  25                  30

Gln Lys Gln Gln Val Ile Ile Glu Ile Gln Gln Glu Glu Val Ile Pro
        35                  40                  45

Thr Arg Met Asp Arg Val Lys Tyr Leu Ala Tyr Ala Cys Cys Ala Thr
    50                  55                  60

```
Ser Thr Arg Val Met Cys Trp Leu Phe Leu Ile Cys Val Leu Leu Ile
 65                  70                  75                  80

Ile Val Phe Val Ser Cys Phe Val Thr Val Ala Arg Ile Gln Trp Asn
                 85                  90                  95

Arg Asp Ile Asn Val Phe Gly Pro Val Ile Asp Trp Asn Val Thr His
                100                 105                 110

Gln Ala Thr Tyr Gln Gln Leu Lys Ala Ala Arg Leu Thr Arg Ser Leu
            115                 120                 125

Lys Val Glu His Pro His Ile Ser Tyr Ile Ser Ile Asn Met Ser Ser
        130                 135                 140

Ile Pro Gln Gly Val Met Tyr Thr Pro His Pro Glu Pro Ile Ile Leu
145                 150                 155                 160

Lys Glu Arg Val Leu Gly Ile Ser Gln Val Leu Met Ile Asn Ser Glu
                165                 170                 175

Asn Ile Ala Asn Val Ala Asn Leu Ser Gln Glu Thr Lys Val Leu Leu
                180                 185                 190

Thr Asp Met Ile Asn Glu Glu Leu Gln Asp Leu Ser Asn Gln Met Ile
            195                 200                 205

Asp Phe Glu Leu Pro Leu Gly Asp Pro Arg Asp Gln Asp Gln Tyr Ile
210                 215                 220

His His Lys Cys Tyr Gln Glu Phe Ala His Cys Tyr Leu Val Lys Tyr
225                 230                 235                 240

Lys Lys Pro Ser Pro Trp Ile Ser Glu Gly Ile Ile Val Asp Gln Cys
                245                 250                 255

Pro Leu Pro Arg Ile His Asp Pro Asn Tyr Tyr Lys Tyr Gln Pro Ile
                260                 265                 270

Trp Asp Tyr Tyr Leu Lys Ile Gln Asn Ile Arg Pro Gln Gly Trp Thr
            275                 280                 285

Ser Lys Ser Tyr Tyr Gly Thr Ala Arg Met Gly Ser Phe Tyr Ile Pro
        290                 295                 300

Thr Phe Leu Arg Asn Asn Thr Val Ser His Val Leu Phe Cys Ser Asp
305                 310                 315                 320

Gln Leu Tyr Gly Lys Trp Tyr Asn Ile Glu Asn Asn Ile Gln Glu Asn
                325                 330                 335

Glu Gln Leu Leu Lys Thr Lys Leu Tyr Asn Leu Thr Thr Tyr Ser Lys
            340                 345                 350

Leu Lys Ala Arg Ala Leu Pro Lys Glu Trp Asn Asn Gln Gly Asn Ala
        355                 360                 365

Arg Leu Phe Arg Ser Phe Asn Pro Leu Asp Val Cys Asn Arg Pro Glu
        370                 375                 380

Ala Val Leu Leu Leu Asn Thr Thr Tyr Phe Thr Tyr Ser Leu Trp Glu
385                 390                 395                 400

Gly Asp Cys Asn Tyr Thr Thr Ala Leu Ile Gln Asn Leu Thr Glu Cys
                405                 410                 415

Arg Gln Pro Asp Arg Leu Lys Leu Lys His Pro Tyr Ala Cys Arg Phe
            420                 425                 430

Trp Arg Tyr Lys Glu Gly Gln Glu Val Lys Cys Leu Gly Asn Glu
        435                 440                 445

Lys Lys Lys Cys Leu Tyr Tyr Ser Glu Tyr Ser Pro Glu Ala Gln
        450                 455                 460

Phe Asp Phe Gly Phe Leu Ser Tyr Leu Asn Ala Phe Pro Gly Leu Lys
465                 470                 475                 480
```

```
Tyr Ile Glu Asn Gln Thr Val Arg Glu Pro Glu Tyr Glu Val Tyr Ser
                485                 490                 495

Leu Tyr Met Glu Cys Met Asn Ser Ala Glu Lys Tyr Gly Ile Asp Ser
            500                 505                 510

Val Leu Phe Ala Leu Lys Thr Phe Leu Asn Phe Thr Gly Thr Pro Val
        515                 520                 525

Asn Glu Met Ser Thr Ala Arg Ala Phe Val Gly Leu Thr Asp Pro Lys
    530                 535                 540

Phe Pro Pro Thr Tyr Pro Asn Ile Thr Lys Glu Gln Lys Arg Cys Asn
545                 550                 555                 560

Asn Leu Lys Arg Arg Lys Arg Ser Thr Asn Ile Glu Lys Leu Arg Ser
                565                 570                 575

Met Gly Tyr Ser Leu Thr Gly Ala Val Gln Thr Leu Ser Gln Ile Ser
            580                 585                 590

Asp Ile Asn Asp Glu Arg Leu Gln Gln Gly Val Ser Leu Leu Arg Asp
        595                 600                 605

His Val Val Thr Leu Met Glu Ala Ala Leu His Asp Ile Thr Ile Met
    610                 615                 620

Glu Gly Met Leu Ala Ile Gln His Val His Thr His Leu Asn His Leu
625                 630                 635                 640

Lys Thr Ile Leu Leu Met Arg Lys Ile Asp Trp Thr Phe Ile Lys Ser
                645                 650                 655

Asn Trp Ile Lys Glu Gln Leu Gln Lys Thr Glu Asp Glu Met Lys Ile
            660                 665                 670

Ile Arg Arg Thr Ala Lys Ser Leu Val Tyr Tyr Val Thr Gln Thr Ser
        675                 680                 685

Ser Ser Thr Thr Ala Thr Ser Trp Glu Ile Gly Ile Tyr Tyr Glu Ile
    690                 695                 700

Thr Ile Pro Lys His Ile Tyr Leu Asn Asn Trp Gln Val Ile Asn Ile
705                 710                 715                 720

Gly His Leu Val Glu Ser Ala Gly His Leu Thr Leu Ile Arg Val Lys
                725                 730                 735

His Pro Tyr Glu Val Ile Asn Lys Glu Cys Thr Tyr Glu Gln Tyr Leu
            740                 745                 750

His Leu Glu Asp Cys Ile Ser Gln Asp Tyr Val Ile Cys Asp Thr Val
        755                 760                 765

Gln Ile Val Ser Pro Cys Gly Asn Ser Thr Thr Ser Asp Cys Pro
    770                 775                 780

Val Thr Ala Glu Lys Val Lys Glu Pro Tyr Val Gln Val Ser Ala Leu
785                 790                 795                 800

Lys Asn Gly Ser Tyr Leu Val Leu Thr Ser Arg Thr Asp Cys Ser Ile
                805                 810                 815

Pro Ala Tyr Val Pro Ser Ile Val Thr Val Asn Glu Thr Val Lys Cys
            820                 825                 830

Phe Gly Val Glu Phe His Lys Pro Leu Tyr Ser Glu Ser Lys Val Ser
        835                 840                 845

Phe Glu Pro Gln Val Pro His Leu Lys Leu Arg Leu Pro His Leu Val
    850                 855                 860

Gly Ile Ile Ala Asn Leu Gln Asn Leu Glu Ile Glu Val Thr Ser Thr
865                 870                 875                 880

Gln Glu Ser Ile Lys Asp Gln Ile Glu Arg Ala Lys Ser Gln Leu Leu
                885                 890                 895

Arg Leu Asp Ile His Glu Gly Asp Phe Pro Ala Trp Ile Gln Gln Leu
```

```
                    900             905             910
Ala Ser Ala Thr Arg Asp Val Trp Pro Ala Ala Arg Ala Leu Gln
        915             920             925
Gly Ile Gly Asn Val Leu Ser Asn Thr Ala Gln Gly Ile Phe Gly Thr
        930             935             940
Thr Val Ser Ile Leu Ser Tyr Ala Lys Pro Ile Leu Gly Ile Gly
945             950             955             960
Val Ile Leu Leu Ile Ala Phe Leu Phe Lys Ile Val Ser Trp Leu Pro
            965             970             975
Gly Lys Lys Lys Arg Asn
        980

<210> SEQ ID NO 36
<211> LENGTH: 980
<212> TYPE: PRT
<213> ORGANISM: Squirrel monkey foamy virus
<220> FEATURE:
<223> OTHER INFORMATION: Env (GenBank: ADE05996.1)

<400> SEQUENCE: 36

Met Ala Arg Pro Met Thr Leu His Glu Trp Leu Lys Trp Lys Lys Thr
1               5               10              15
Asn Ala Val Arg Gln Leu Thr Glu Asn Leu Gln Ser Leu Pro Pro Glu
            20              25              30
Gln Lys Glu Leu Leu Ile Gln Glu Ile Glu Glu Glu Asp Val Pro Thr
        35              40              45
Pro Ser Trp Thr Gln Lys Cys Ser Tyr Met Cys Tyr Leu Ala Cys Ala
50              55              60
Thr Thr Thr Arg Ile Met Gly Trp Ile Ile Phe Thr Leu Ile Ile Ala
65              70              75              80
Ser Val Ile Leu Val Thr Cys Phe Val Val Met Ala Arg Ile Gln Trp
            85              90              95
Arg Asn Ala Ile Thr Val Pro Gly Ile Ile Leu Asp Trp Asn Ser Thr
        100             105             110
Ser His Glu Val Phe Pro Met Pro Gln Asn Lys Arg Arg Ser Ala Arg
    115             120             125
Asp Leu Ile Arg Ile Leu Glu Glu Asn Ile Val Glu Ile Asn Thr Thr
130             135             140
Ser Leu Pro Gln Gly Ile Leu Phe Glu Pro His Pro Lys Pro Ile Ile
145             150             155             160
Gly Lys Glu Arg Val Leu Gly Leu Ser Gln Val Ile Leu Ile Asn Ser
            165             170             175
Glu Ser Ile Ala Thr Ser Leu Glu Ile Lys Gln Glu His Lys His Ile
        180             185             190
Leu Val Glu Met Ile Lys Glu Glu Leu Leu Ser Leu Gln Asn Val Met
    195             200             205
Leu Asn Phe Asp Leu Pro Leu Gly Asp Pro Lys Thr Gln Gln Glu Tyr
    210             215             220
Ile Ser Gln Arg Cys Phe Gln Glu Phe Lys His Cys Tyr Leu Val Ala
225             230             235             240
Tyr Asn Glu Thr Gln Lys Pro Trp Pro Thr Asp Asp Val Val Gln Asp
            245             250             255
Met Cys Pro Leu Pro Gly Asn Gly Tyr Ser Pro Gln Asn Ala Trp Asp
        260             265             270
Tyr Tyr Leu Glu Ile Lys Asn Ile Arg Pro Glu Asn Trp Thr Ser Lys
```

-continued

```
              275                 280                 285
Asp Tyr Phe Gly Ser Ala Arg Met Gly Gly Phe Trp Val Pro Pro Trp
290                 295                 300

Leu Arg Gln Asn Asn Tyr Thr His Val Leu Phe Cys Ser Asp Gln Leu
305                 310                 315                 320

Tyr Glu Lys Trp Tyr Ile Pro Tyr Gly Leu Thr Glu Asn Asp Val
                325                 330                 335

Lys Leu Met Asn Lys Leu Lys Thr Leu Leu Asn Gly Thr Asn Lys Leu
                340                 345                 350

Lys Ala Arg Ala Leu Ser Ala Tyr Trp His Pro Gln Gly Gln Asn Lys
                355                 360                 365

Leu Phe Arg Asn Ile Thr Arg Leu Asp Tyr Cys Lys Tyr Pro Glu Ala
370                 375                 380

Val Ile Leu Leu Asn Thr Thr Lys Ser Asp Tyr Ser Leu Trp Glu Gly
385                 390                 395                 400

Asp Cys Asn Ile Trp Ala His Asn Ile Thr Val His Pro Ala Cys Lys
                405                 410                 415

Asn Phe Asn Phe Ser Glu Lys Ser Lys Val His Pro Tyr Thr Cys Arg
                420                 425                 430

His Trp Arg Phe Lys Glu Gly Pro Glu Gln Thr Lys Cys Leu Glu Asp
                435                 440                 445

Lys Thr Gln Cys Leu Tyr Tyr Ser Glu Tyr Ser Ser Pro Ser Tyr Leu
450                 455                 460

Gln Asp Phe Gly Trp Leu Ala Tyr Gln Gly His Phe Pro Ser Pro Ile
465                 470                 475                 480

Cys Glu Lys Glu Thr Lys Ile Arg Met Pro Gly Tyr Thr Val Tyr Ser
                485                 490                 495

Leu Phe Gly Glu Cys Leu Asn Ala Ala Gln Gln His Gly Ile Glu Arg
                500                 505                 510

Ala Leu Ile Gly Leu His Ala Phe Met Asn Phe Thr Lys Thr Pro Leu
                515                 520                 525

Gln Glu Val Asn Lys Glu Arg Ala Phe Ile Gly Leu Asp Ser Pro Lys
530                 535                 540

Trp Pro Pro Thr Tyr Pro Asn Ile Thr Ile Phe Ser Val Asp Lys Cys
545                 550                 555                 560

Lys Thr Glu Lys Arg Lys Lys Arg Glu Ile His Asn Trp Gly Lys Leu
                565                 570                 575

Gln Ala Val Gly Phe Thr Ile Thr Asn Thr Val Ser Lys Ile Ala Arg
                580                 585                 590

Ile Ile Asp Leu Asn Asn Glu His Leu Val Ser Gly Leu Tyr Leu Leu
                595                 600                 605

Lys Asp His Leu Val Thr Leu Met Glu Ser Thr Leu His Asp Ile Ser
                610                 615                 620

Ile Leu Gly Asn Ala Val Ala Ile Gln His Phe His Thr His Leu Thr
625                 630                 635                 640

Gln Leu Lys Leu Leu Leu Met Glu Asn Arg Met Asp Trp Thr Phe Ile
                645                 650                 655

Asp Ser Ser Trp Ile Gln Asp Gln Leu Lys Leu Ser Asp Glu Asp Met
                660                 665                 670

Lys Ile Leu Arg Arg Ala Ser Arg Ala Leu Val Tyr Lys Val Glu Glu
                675                 680                 685

Ile Gly Glu Gly Val Thr Ser Thr Ile Trp Glu Ile Gly Ile Tyr Tyr
                690                 695                 700
```

Glu Ile Ile Ile Pro Arg Val Ile Tyr Ser Thr Asn Trp Lys Ile Met
705                 710                 715                 720

Asn Leu Gly His Leu Val Tyr Ser Ala Asp Asn Leu Val Gln Ile Asn
            725                 730                 735

Val Glu Gln Pro Tyr Glu Ile Leu Asn Val Glu Cys Gly Lys Ser Thr
        740                 745                 750

Tyr Leu His Ile Asp Lys Cys Glu Glu Gln Asp Tyr Val Ile Cys Glu
    755                 760                 765

Val Ile Gln Glu Lys Gln Pro Cys Gly Asn Gln Ser Gly Ser Asp Cys
770                 775                 780

Pro Val Lys Ala Arg Thr Ile Glu Lys Gly Tyr Thr Tyr Ile Gln Pro
785                 790                 795                 800

Leu Lys Asn Gly Ser Tyr Val Val Met Ser His Phe Gln Asp Cys His
            805                 810                 815

Ile Lys Pro Tyr Ile Pro Gln Ile Val Thr Val Asn Ala Thr Val Lys
        820                 825                 830

Cys Leu Gly Glu Val Phe Gln Pro Pro Leu Val Pro Gly Asn Ser Ser
    835                 840                 845

Thr Glu Val Leu Pro Val Thr Thr Ser Leu Lys Leu Gln Leu Pro His
850                 855                 860

Leu Val Gly Ile Ile Thr Lys Leu Lys Gly Phe Gln Val Gln Ile Thr
865                 870                 875                 880

Ser Thr Trp Glu Ser Ile Lys Gly Gln Val Glu Gln Ala Gln Ala Glu
            885                 890                 895

Leu Leu Arg Leu Asp Leu His Glu Gly Asp Ser Gly Gln Trp Ile Lys
        900                 905                 910

Gln Leu Ala Ser Ala Ser Lys Asp Ile Trp Pro Ala Ala Ala Thr Val
    915                 920                 925

Leu Gly Lys Ile Gly Asp Phe Leu Gly Gly Thr Ala Gly Ser Ile Phe
930                 935                 940

Gly Ile Phe Gly Tyr Leu Lys Pro Ile Phe Ile Gly Leu Thr Ile Leu
945                 950                 955                 960

Ile Leu Ile Val Leu Val Phe Lys Ile Leu Ser Trp Leu Pro Thr Lys
            965                 970                 975

Arg Lys Ala Gln
            980

<210> SEQ ID NO 37
<211> LENGTH: 986
<212> TYPE: PRT
<213> ORGANISM: equine foamy virus
<220> FEATURE:
<223> OTHER INFORMATION: Env (NCBI Reference: NP_054717.1)

<400> SEQUENCE: 37

Met Thr Pro Pro Met Thr Leu Pro Glu Trp Met Gln Trp Arg Tyr Arg
1               5                   10                  15

Gln Asn Val Asn Lys Ile Arg Glu Ala Ile Pro Asp Val Gln Ile Asp
            20                  25                  30

Leu Pro Val Tyr Asn Pro Asp Met Thr Lys Pro Leu Pro Leu Cys Leu
        35                  40                  45

Arg Ile Lys Tyr Trp Met Tyr Leu Leu Cys Ala Thr Ser Pro Arg Val
    50                  55                  60

Met Ala Trp Leu Leu Phe Val Cys Val Leu Ile Ser Val Met Ile Ile
65                  70                  75                  80

```
Ala Val Ile Val Thr Val Phe Arg Met Gln Trp Lys Ala Ala Ile Asp
                85                  90                  95

Val Pro Gly Pro Val Leu Phe Trp Asn His Thr Asp Val Leu Thr His
            100                 105                 110

Val Pro Pro Val Gly Pro His Val Thr Arg Leu Arg Arg Ala Val His
        115                 120                 125

Leu Ala Asp Arg Ala Val Asn Ile Asn Ile Thr His Ile Pro Gln Gly
130                 135                 140

Val Phe Leu Glu Pro Phe Pro Lys Pro Ile Ile Asp Lys Glu Arg Val
145                 150                 155                 160

Leu Gly Ile Ser Gln Ile Val Met Ile Asp Ser Gly Ser Ile Ala Gln
                165                 170                 175

Ser Met Asn Leu Asp Leu Tyr Met Lys His Leu Leu Val Asp Met Ile
            180                 185                 190

Asn Glu Glu Met Val Ala Leu Ser Asn Val Val Leu Pro Phe Glu Leu
        195                 200                 205

Pro Val Gly Asp Pro Ser Thr Gln Asp Gln Tyr Ile His Lys Arg Cys
210                 215                 220

Tyr Gln Gln Phe Ala His Cys Tyr Ile Val Trp Gln Pro Gly Arg Arg
225                 230                 235                 240

Val Trp Pro Thr Ser Glu Ile Ile Gln Asp Gln Cys Pro Leu Pro Asp
                245                 250                 255

His Pro Tyr Arg Pro Leu Gly Tyr Met Gln Gln Asn Ala Tyr Asp Leu
            260                 265                 270

Tyr Leu Gln Pro Pro Arg Tyr Gly Leu Gln Asn Val Asn Leu Thr Ser
        275                 280                 285

Leu Tyr Gly Ile Ala Arg Ile Gly Ala Tyr Arg Val Leu Tyr Pro Glu
290                 295                 300

Gln Tyr Asn Ala Thr Ile Phe Cys Ser Asp Gln Leu Tyr Gly Asn Trp
305                 310                 315                 320

Trp Tyr Leu Asn Arg Thr Ser Glu Gln Lys Glu Thr Tyr Arg Lys
                325                 330                 335

Lys Met Leu Asn Leu Thr Glu Asn Asn Ser Ser Ile Leu Lys Asp Arg
            340                 345                 350

Ala Leu Pro Pro Thr Trp Thr Pro Lys Gly Gln Ala Arg Leu Phe Arg
        355                 360                 365

Glu Leu Asn Pro Leu Asp Phe Cys Thr Lys Pro Glu Ala Val Met Leu
370                 375                 380

Leu Asn Gln Ser Tyr Tyr Thr Trp Ser Leu Trp Glu Gly Asp Cys Tyr
385                 390                 395                 400

Val Tyr Ser Arg Asn Ile Ser Phe Pro Pro Glu Cys Ile Asn Tyr Thr
                405                 410                 415

Arg Ile Ala Asn Lys Thr Ala His Pro Tyr Ala Cys Arg His Trp Arg
            420                 425                 430

Leu Leu Ser Thr Asn Asn Glu Gly Lys Asp Glu Ile Lys Cys Ser Glu
        435                 440                 445

Tyr Gly Cys Leu Phe Tyr Pro Lys Tyr Asp Gln Phe Glu Leu Ala Asn
450                 455                 460

Asp Phe Gly Phe Leu Ala Tyr Gln Lys Met Phe Pro Ser Pro Ile Cys
465                 470                 475                 480

Ile Gln Asn Tyr Ser Leu Ser Thr Glu Pro Tyr Lys Val Gln Ser Leu
                485                 490                 495
```

```
Tyr Gln Glu Cys Ile Gln Lys Gly Thr Ser Tyr Asp Leu Glu Asp Val
                500                 505                 510

Ile Asn Gln Leu Leu Arg Val Leu Gln Asn Asn Gly Ile Asp Leu Gly
            515                 520                 525

Lys Val Pro Ala Ser Arg Ala Phe Thr Pro Phe Tyr Asn Gln Met Pro
        530                 535                 540

Val Ser Tyr Lys Lys Arg Asp Val Thr Lys Arg Lys Ser Cys Gly Arg
545                 550                 555                 560

Arg Lys Arg Gly Asp Asn Phe Arg Lys Leu Gln Thr Ser Gly Leu Ser
                565                 570                 575

Met Asn Gln Ala Ile Ser Thr Leu Ala Lys Ile Ser Asp Leu Asn Asp
            580                 585                 590

Glu Asn Leu Ala Ala Gly Ile His Leu Leu Gln Glu His Ile Val Thr
        595                 600                 605

Leu Met Glu Ala Thr Val His Asp Ile Ser Met Leu Glu Ala Ala His
    610                 615                 620

Gly Leu Gln Ile Leu His Thr His Leu Ser Thr Leu Arg Leu Leu Leu
625                 630                 635                 640

Thr Glu Asn Arg Val Asp Trp Asn Leu Ile Asp Ser Thr Trp Ile Gln
                645                 650                 655

Gln Gln Leu Gln Ala Asp Glu Ala Leu Met Asn Val Ile Arg Arg Thr
            660                 665                 670

Ala Arg Ser Met Thr Tyr Arg Val Ile Gln Gln Ile Asn Arg Pro Asp
        675                 680                 685

Met Thr Leu Trp Glu Leu Gly Ile Tyr Tyr Glu Leu Ile Ile Pro Lys
    690                 695                 700

Lys Val Trp Leu Thr Asn Trp Lys Ile Gln Asn Ile Gly His Leu Ile
705                 710                 715                 720

Lys Asn Ala Gly His Leu Ala Arg Val Glu Leu Gln His Pro Tyr Glu
                725                 730                 735

Ile Val Asn Gln Asp Cys Glu Gln Leu Thr Tyr Leu Glu Leu Lys Gly
            740                 745                 750

Cys Gln Glu Leu Asp Tyr Leu Val Cys Glu Glu Ile Leu Gln His Glu
        755                 760                 765

Pro Cys Gly Asn Gln Thr Gly Ser Asp Cys Pro Val Thr Ala Gln Lys
    770                 775                 780

Ile Lys Asp Pro Tyr Val Trp Ile Tyr Pro Leu Lys Asn Gly Ser Tyr
785                 790                 795                 800

Leu Ile Met Ser Ser His Thr Asp Cys Ala Ile Pro Pro Tyr Glu Pro
                805                 810                 815

Val Leu Val Thr Val Asn Asp Thr Val Arg Cys Phe Gly Thr Thr Leu
            820                 825                 830

Lys Lys Pro Leu Arg Thr Ser Leu Glu Thr Phe Thr Phe Gln Pro His
        835                 840                 845

Ile Pro Gln Leu Gln Val Arg Leu Pro His Leu Val Gly Leu Ile Ala
    850                 855                 860

Lys Ile Lys Gly Leu Lys Ile Glu Ile Thr Ser Thr Trp Glu Asn Ile
865                 870                 875                 880

Lys Asp Gln Ile Lys Arg Ser Glu Ala Glu Leu Leu Arg Leu Asp Leu
                885                 890                 895

His Glu Gly Asp Tyr Ala Glu Trp Thr Lys Gln Leu Gly Lys Ala Leu
            900                 905                 910

Glu Asp Ile Trp Pro Ala Ala Ala Gln Thr Val Ser Lys Ile Gly Asp
```

915                 920                 925
Phe Leu Gly Lys Ile Ala Asp Gly Ile Phe Thr Thr Phe Ser Leu
            930                 935                 940
Leu Thr Tyr Ala Lys Pro Val Ile Ile Gly Ile Val Ile Val Leu
945                 950                 955                 960
Leu Ile Leu Ile Ile Arg Ile Leu Ser Trp Leu Ala Ala Leu Gly Pro
            965                 970                 975
Arg Arg Arg Arg Arg Glu Asp Lys Gly Glu
            980                 985

<210> SEQ ID NO 38
<211> LENGTH: 990
<212> TYPE: PRT
<213> ORGANISM: Bovine Foamy Virus
<220> FEATURE:
<223> OTHER INFORMATION: Env (GenBank: AFR79240.1)

<400> SEQUENCE: 38

Met Ala Pro Pro Met Thr Leu Gln Gln Trp Leu Gln Trp Arg Tyr Asn
1               5                   10                  15
Leu Glu Thr Thr Asn Leu Leu Gln Met Asn Pro Lys Met Glu Ser Ile
            20                  25                  30
Cys Leu Pro Asp Phe Glu Pro Pro Gly Asp Glu Glu Val Ser Leu Arg
        35                  40                  45
Met Lys Cys Lys Tyr Trp Ile Tyr Leu Cys Cys Ala Thr Ser Thr Arg
    50                  55                  60
Ile Met Ala Trp Ile Val Phe Ile Phe Thr Val Leu Ser Ile Leu Leu
65                  70                  75                  80
Ile Ser Val Leu Ile Ala Val Phe Arg Leu Gln Trp Lys Gly Ala Ile
                85                  90                  95
Glu Ser Pro Gly Pro Ile Leu Val Trp Asn Asn Ser Asn Ser Ile Asn
            100                 105                 110
Ala Gln Ser Thr Thr Pro Pro His Tyr Ser Arg Leu Arg Arg Ala Ile
        115                 120                 125
His Leu Ala Gln Lys Pro Val Gln Val Asn Phe Thr Ser Ile Pro Gln
    130                 135                 140
Gly Leu Phe Leu Glu Pro His Pro Lys Pro Ile Ile Ser Lys Glu Arg
145                 150                 155                 160
Val Leu Gly Leu Ser Gln Val Val Met Val Asp Ser Ser Ser Leu Thr
                165                 170                 175
Gln Lys Leu Asn Leu Val Gly Glu Ala Lys Ser Leu Leu Ile Lys Thr
            180                 185                 190
Ile Asn Glu Glu Leu Ile Ser Leu Gln Asp Val Val Leu Asn Phe Asp
        195                 200                 205
Leu Pro Leu Gly Asp Pro His Thr Gln Glu Glu Tyr Ile Ala Lys Arg
    210                 215                 220
Cys Tyr Gln His Phe Gly His Cys Tyr Val Val His Ile Pro Gly Gly
225                 230                 235                 240
Lys Glu Trp Pro Thr Arg Glu Ile Ile Gln Asp Gln Cys Pro Leu Asn
                245                 250                 255
Asn Ser Trp Leu Thr Ala Leu His Tyr Asp Tyr Leu Pro Ala Trp Asp
            260                 265                 270
Tyr Tyr Asn Gln Pro Pro Arg Gln Leu Ser Leu Glu Asp Phe Arg
        275                 280                 285
Lys Tyr Asn Ile Ser Asn Asn Gly Ser Arg Tyr Glu Ala Tyr Arg Leu

-continued

```
            290                 295                 300
Pro Leu Gln Asp Lys Ile Gly Ala Val Ala Phe Cys Ser Pro Thr Leu
305                 310                 315                 320

Tyr Ser Ser Trp Trp Asn Tyr Thr Gln Ser Ser Arg Glu Arg Glu Glu
                325                 330                 335

Leu Phe Arg Arg Lys Leu Glu Thr Phe Leu Asn Pro Gln Thr Gly Cys
                340                 345                 350

Leu Asn Pro Glu Ala Leu Pro Gly Thr Trp His Thr Leu Gly Lys Gly
                355                 360                 365

Glu Trp Phe Lys Asp Leu Thr Thr Tyr Asp Phe Cys Lys Lys Pro Glu
        370                 375                 380

Ala Val Phe Gly Leu Asn Lys Thr Tyr Tyr Ser Trp Ser Leu Trp Glu
385                 390                 395                 400

Gly Asp Cys Gly Arg Gln Gly Asn Asp Thr Gln Asn Tyr Pro Pro Glu
                405                 410                 415

Cys Arg Asn Tyr Glu Lys Arg Asp Gly Val His Val Tyr Gly Cys Arg
                420                 425                 430

Tyr Trp Arg Thr Tyr Ser Gln Thr Ala His Thr Ser Asp Asn Val Ser
        435                 440                 445

Cys Tyr Leu Ser Glu Asp His Cys Leu Phe Gln Pro Lys Trp Asp Ser
450                 455                 460

Ala Glu Ile Arg Ser Asp Leu Gly Tyr Leu Ala Tyr Leu Gly Ala Phe
465                 470                 475                 480

Pro Ser Pro Ile Cys Ile Glu Ala Lys Asn Leu Thr Asp Gln Asp Tyr
                485                 490                 495

Lys Val Thr Ser Ile Tyr Ala Glu Cys Val Lys Gln Gly Lys Gln Tyr
                500                 505                 510

Asp Ile Ala Asp Val Thr Arg Gln Leu Ala Ser Lys Leu Thr Arg Arg
                515                 520                 525

Gly Val Phe Leu Gly Asp Leu Pro Ala Asp Arg Ala Phe Ser Leu Leu
        530                 535                 540

Ser Asp Phe Ser Leu Pro Asp Ser Tyr Gln Asn Lys Thr Gln Asp Gly
545                 550                 555                 560

Arg Arg Arg Val Cys Ser Ser Lys Arg Thr Arg Ser Ile Asn Asn
                565                 570                 575

Trp Arg Arg Leu Gln Ile Ala Gly Gln Ser Met Asn Gln Ala Ile Thr
                580                 585                 590

Thr Leu Ser Lys Leu Ser Asp Leu Asn Asp Glu Asn Leu Ala Ala Gly
        595                 600                 605

Ile His Leu Leu Gln Asp His Ile Ile Thr Leu Met Glu Ala Thr Leu
        610                 615                 620

His Asp Val Ser Leu Leu Gly His Met Ala Ser Ile Gln His Leu His
625                 630                 635                 640

Thr His Leu Ala Thr Phe Lys Asn Leu Leu Ile Gly Asn Arg Val Asp
                645                 650                 655

Trp Ser Val Leu Glu Ser Arg Trp Ile Gln Glu Leu Lys Tyr Thr
                660                 665                 670

Asp Glu Val Met Asn Val Ile Arg Arg Thr Ala Arg Ser Ile Thr Tyr
                675                 680                 685

Asp Val Gln Asn Val Lys Asn Thr Ser Asp Ser Thr Ile Trp Glu Ile
        690                 695                 700

Tyr Ile Tyr Tyr Glu Leu Ile Leu Pro Glu Arg Ile Trp Ile Arg Asn
705                 710                 715                 720
```

```
Trp Gln Val Ala Asn Leu Gly His Leu Thr Tyr Asn Ser Gly His Leu
                725                 730                 735

Thr His Val Thr Ile His His Pro Tyr Glu Ile Val Asn Gln Asp Cys
            740                 745                 750

Glu Glu Leu Thr Phe Leu His Leu Val Asp Cys His Glu Gln Asp Tyr
        755                 760                 765

Leu Ile Cys Glu Glu Val Val Glu Val Glu Pro Cys Gly Asn Leu Thr
    770                 775                 780

Gly Ser Asp Cys Pro Val Leu Ala Glu Asn Ile Gln Ala Pro Tyr Val
785                 790                 795                 800

Tyr Leu His Pro Leu Lys Asn Gly Ser Tyr Leu Leu Met Ala Ser His
                805                 810                 815

Thr Asp Cys Ser Leu Pro Pro Tyr Glu Pro Val Val Thr Val Asn
            820                 825                 830

Asp Ser Leu Glu Cys Tyr Gly Lys Pro Leu Lys Arg Pro Leu Thr Ser
        835                 840                 845

His Thr Glu Ile Lys Leu Phe Ala Pro Gln Ile Pro Gln Leu Arg Val
    850                 855                 860

Arg Leu Pro His Leu Val Gly Ile Ile Ala Lys Leu Lys Ser Leu Lys
865                 870                 875                 880

Ile Lys Val Thr Ser Thr Trp Glu Ser Ile Lys Asp Gln Ile His Arg
                885                 890                 895

Ser Glu Gln Glu Leu Leu Arg Leu Asp Leu His Glu Gly Asp Tyr Ser
            900                 905                 910

Asp Trp Ile Leu Gln Leu Gly Asn Ala Leu Glu Asp Val Trp Pro Val
        915                 920                 925

Ala Ala Ser Ala Val Ser Thr Ile Gly Thr Leu Leu Glu Lys Ala Ala
    930                 935                 940

Gly Thr Leu Phe Gly Asn Val Phe Ser Ile Leu Ala Tyr Ala Lys Pro
945                 950                 955                 960

Val Ile Ile Gly Ile Ile Leu Ile Ile Leu Leu Leu Val Ile Arg
                965                 970                 975

Ile Leu Arg Trp Leu Ala Val Gly Arg Arg Lys Gln Glu
            980                 985                 990

<210> SEQ ID NO 39
<211> LENGTH: 982
<212> TYPE: PRT
<213> ORGANISM: Feline Foamy virus
<220> FEATURE:
<223> OTHER INFORMATION: Env (GenBank: CAA11582.1)

<400> SEQUENCE: 39

Met Glu Gln Glu His Val Met Thr Leu Lys Glu Trp Met Glu Trp Asn
1               5                   10                  15

Ala His Lys Gln Leu Gln Lys Leu Gln Ser Thr His Pro Glu Leu His
            20                  25                  30

Val Asp Ile Pro Glu Asp Ile Pro Leu Val Pro Glu Lys Val Pro Leu
        35                  40                  45

Lys Met Arg Met Arg Tyr Arg Cys Tyr Thr Leu Cys Ala Thr Ser Thr
    50                  55                  60

Arg Ile Met Phe Trp Ile Leu Phe Phe Leu Cys Phe Ser Ile Val
65                  70                  75                  80

Thr Leu Ser Thr Ile Ile Ser Ile Leu Arg Tyr Gln Trp Lys Glu Ala
                85                  90                  95
```

```
Ile Thr His Pro Gly Pro Val Leu Ser Trp Gln Val Thr Asn Ser His
            100                 105                 110

Val Thr Met Gly Gly Asn Thr Ser Ser Ser Arg Arg Arg Arg Asp
            115                 120                 125

Ile Gln Tyr His Lys Leu Pro Val Glu Val Asn Ile Ser Gly Ile Pro
            130                 135                 140

Gln Gly Leu Phe Phe Ala Pro Gln Pro Lys Pro Ile Phe His Lys Glu
145                 150                 155                 160

Arg Thr Leu Gly Leu Ser Gln Val Ile Leu Ile Asp Ser Asp Thr Ile
            165                 170                 175

Thr Gln Gly His Ile Lys Gln Gln Lys Ala Tyr Leu Val Ser Thr Ile
            180                 185                 190

Asn Glu Glu Met Glu Gln Leu Gln Lys Thr Val Leu Pro Phe Asp Leu
            195                 200                 205

Pro Ile Lys Asp Pro Leu Thr Gln Lys Glu Tyr Ile Glu Lys Arg Cys
            210                 215                 220

Phe Gln Lys Tyr Gly His Cys Tyr Val Ile Ala Phe Asn Gly Asn Lys
225                 230                 235                 240

Val Trp Pro Ser Gln Asp Leu Ile Gln Asp Gln Cys Pro Leu Pro Pro
            245                 250                 255

Arg Phe Gly Asn Asn Leu Lys Tyr Arg Asn His Thr Ile Trp Lys Tyr
            260                 265                 270

Tyr Ile Pro Leu Pro Phe Lys Val Ser Ser Asn Trp Thr Arg Val Glu
            275                 280                 285

Ser Tyr Gly Asn Ile Arg Ile Gly Ser Phe Lys Val Pro Asp Glu Phe
            290                 295                 300

Arg Gln Asn Ala Thr His Gly Ile Phe Cys Ser Asp Ala Leu Tyr Ser
305                 310                 315                 320

Asn Trp Tyr Pro Arg Asp Leu Pro Ser Ser Val Gln Gln Ser Phe Ala
            325                 330                 335

Gln Ala Tyr Ile Thr Lys Val Leu Met Lys Arg Lys Lys Gln Pro Thr
            340                 345                 350

Leu Arg Asp Ile Ala Phe Pro Lys Glu Leu Ser Pro Val Gly Ser Gly
            355                 360                 365

Met Leu Phe Arg Pro Ile Asn Pro Tyr Asp Ile Cys Asn Met Pro Arg
            370                 375                 380

Ala Val Leu Leu Leu Asn Lys Thr Tyr Tyr Thr Phe Ser Leu Trp Glu
385                 390                 395                 400

Gly Asp Cys Gly Tyr Tyr Gln His Asn Leu Thr Leu His Pro Ala Cys
            405                 410                 415

Lys Asn Phe Asn Arg Thr Arg Gln Asp His Pro Tyr Ala Cys Arg Phe
            420                 425                 430

Trp Arg Asn Lys Tyr Asp Ser Glu Ser Val Gln Cys Tyr Asn Asn Asp
            435                 440                 445

Met Cys Tyr Tyr Arg Pro Leu Tyr Asp Gly Thr Glu Asn Thr Glu Asp
            450                 455                 460

Trp Gly Trp Leu Ala Tyr Thr Asp Ser Phe Pro Ser Pro Ile Cys Ile
465                 470                 475                 480

Glu Glu Lys Arg Ile Trp Lys Lys Asn Tyr Thr Leu Ser Ser Val Leu
            485                 490                 495

Ala Glu Cys Val Asn Gln Ala Met Glu Tyr Gly Ile Asp Glu Val Leu
            500                 505                 510
```

```
Ser Lys Leu Asp Leu Ile Phe Gly Asn Leu Thr His Gln Ser Ala Asp
            515                 520                 525

Glu Ala Phe Ile Pro Val Asn Asn Phe Thr Trp Pro Arg Tyr Glu Lys
530                 535                 540

Gln Asn Lys Gln Gln Lys Thr Ser Cys Glu Arg Lys Lys Gly Arg Arg
545                 550                 555                 560

Gln Arg Arg Ser Val Ser Thr Glu Asn Leu Arg Arg Ile Gln Glu Ala
                565                 570                 575

Gly Leu Gly Leu Ala Asn Ala Ile Thr Thr Val Ala Lys Ile Ser Asp
            580                 585                 590

Leu Asn Asp Gln Lys Leu Ala Lys Gly Val His Leu Leu Arg Asp His
            595                 600                 605

Val Val Thr Leu Met Glu Ala Asn Leu Asp Asp Ile Val Ser Leu Gly
610                 615                 620

Glu Gly Ile Gln Ile Glu His Ile His Asn His Leu Thr Ser Leu Lys
625                 630                 635                 640

Leu Leu Thr Leu Glu Asn Arg Ile Asp Trp Arg Phe Ile Asn Asp Ser
                645                 650                 655

Trp Ile Gln Glu Glu Leu Gly Val Ser Asp Asn Ile Met Lys Val Ile
            660                 665                 670

Arg Lys Thr Ala Arg Cys Ile Pro Tyr Asn Val Lys Gln Thr Arg Asn
            675                 680                 685

Leu Asn Thr Ser Thr Ala Trp Glu Ile Tyr Leu Tyr Tyr Glu Ile Ile
            690                 695                 700

Ile Pro Thr Thr Ile Tyr Thr Gln Asn Trp Asn Ile Lys Asn Leu Gly
705                 710                 715                 720

His Leu Val Arg Asn Ala Gly Tyr Leu Ser Lys Val Trp Ile Gln Gln
                725                 730                 735

Pro Phe Glu Val Leu Asn Gln Glu Cys Gly Thr Asn Ile Tyr Leu His
            740                 745                 750

Met Glu Glu Cys Val Asp Gln Asp Tyr Ile Ile Cys Glu Glu Val Met
            755                 760                 765

Glu Leu Pro Pro Cys Gly Asn Gly Thr Gly Ser Asp Cys Pro Val Leu
770                 775                 780

Thr Lys Pro Leu Thr Asp Glu Tyr Leu Glu Ile Glu Pro Leu Lys Asn
785                 790                 795                 800

Gly Ser Tyr Leu Val Leu Ser Ser Thr Thr Asp Cys Gly Ile Pro Ala
                805                 810                 815

Tyr Val Pro Val Val Ile Thr Val Asn Asp Thr Ile Ser Cys Phe Asp
            820                 825                 830

Lys Glu Phe Lys Arg Pro Leu Lys Gln Glu Leu Lys Val Thr Lys Tyr
            835                 840                 845

Ala Pro Ser Val Pro Gln Leu Glu Leu Arg Val Pro Arg Leu Thr Ser
850                 855                 860

Leu Ile Ala Lys Ile Lys Gly Ile Gln Ile Glu Ile Thr Ser Ser Trp
865                 870                 875                 880

Glu Thr Ile Lys Glu Gln Val Ala Arg Ala Lys Ala Glu Leu Leu Arg
                885                 890                 895

Leu Asp Leu His Glu Gly Asp Tyr Pro Glu Trp Leu Gln Leu Leu Gly
            900                 905                 910

Glu Ala Thr Lys Asp Val Trp Pro Thr Ile Ser Asn Phe Val Ser Gly
            915                 920                 925

Ile Gly Asn Phe Ile Lys Asp Thr Ala Gly Gly Ile Phe Gly Thr Ala
```

```
                930               935               940
    Phe Ser Phe Leu Gly Tyr Val Lys Pro Val Leu Gly Phe Val Ile
    945               950               955               960

Ile Phe Cys Ile Ile Leu Ile Ile Lys Ile Ile Gly Trp Leu Gln Asn
                    965               970               975

Thr Arg Lys Lys Asp Gln
                    980

<210> SEQ ID NO 40
<211> LENGTH: 2975
<212> TYPE: DNA
<213> ORGANISM: artificial sequence
<220> FEATURE:
<223> OTHER INFORMATION: Description of artificial sequence: Synthetic
      polynucleotide
<220> FEATURE:
<223> OTHER INFORMATION: FV_EM20_HCO_Seq

<400> SEQUENCE: 40
ccatggcccc tcccatgacc ctgcagcagt ggatcatctg gaagaagatg aacaaggccc       60
acgaggccct gcagaacacc accaccgtga ccgagcagca gaaagagcag atcatcctgg      120
acatccagaa cgaggaagtg cagcccacca ggcgggacag gttcagatac ctgctgtaca      180
cctgctgcgc cacctccagc cgggtgctgg cctggatgtt cctggtgtgc atcctgctga      240
tcatcgtgct ggtgtcctgc ttcgtgacca tcagccggat ccagtggaac aaggacatcc      300
aggtgctggg cccccgtgatc gactggaacg tgacccagcg ggccgtgtac cagcccctgc      360
agacccggcg gatcgcccgg tccctgcgga tgcagcaccc cgtgcccaag tacgtggagg      420
tgaacatgac cagcatcccc cagggcgtgt actacgagcc ccaccccgag cccatcgtgg      480
tgaaagaaag agtgctgggc ctgagccaga tcctgatgat caacagcgag aacatcgcca      540
acaacgccaa cctgacccag gaagtgaaga aactgctgac cgagatggtg aacgaagaga      600
tgcagagcct gagcgacgtg atgatcgact tcgagatccc cctgggcgac ccagggacc      660 aggaacagta catccaccgg aagtgctacc aggaatttgc caactgctac ctggtgaagt      720
acaaagagcc caagccctgg cccaaagagg gcctgatcgc cgaccagtgc ccctgcccg      780 gctatcacgc cggcctgacc tacaaccggc agagcatctg ggactactac atcaaggtgg      840
agagcatcag gccgccaac tggaccacca gagcaagta cggccaggcc cggctgggca      900
gcttctacat ccccagcagc ctgcggcaga tcaacgtgag ccacgtgctg ttctgcagcg      960
accagctgta cagcaagtgg tacaacatcg agaacaccat cgagcagaac gagcggttcc     1020
tgctgaacaa gctgaataac ctgaccagcg caccagcgt gctgaagaag agagccctgc     1080
ccaaggactg gtccagccag ggcaagaacg ccctgttccg ggagatcaat gtgctggaca     1140
tctgcagcaa gcccgagagc gtgatcctgc tgaataccag ctactacagc ttcagcctgt     1200
gggagggcga ctgcaacttc accaaggaca tgatcagcca gctggtgccc gagtgcgacg     1260
gcttctacaa caactccaag tggatgcaca tgcacccta cgcctgccgg ttctggcgga     1320
gcaagaacga gaaagaggaa accaagtgcc gggacggcga gaccaagcgg tgcctgtact     1380
accccctgtg ggacagccct gagagcacct acgacttcgg ctacctggcc taccagaaga     1440
acttccccag ccccatctgc atcgaacagc agaagatccg ggaccaggac tacgaggtgt     1500
acagcctgta ccaggaatgc aagatcgcca gcaaggccta cggcatcgac accgtgctgt     1560
tcagcctgaa gaatttcctg aactacaccg gcacccccgt gaacgagatg cccaacgcca     1620
gggccttcgt gggcctgatt gaccccaagt ccccccccag ctaccccaac gtgacccggg     1680
```

-continued

```
agcactacac cagctgcaac aaccggaagc ggactagcgt ggacaacaac tacgccaagc    1740
tgcggagcat gggctacgct ctgacaggcg ccgtgcagac cctgtcccag atcagcgaca    1800
tcaacgacga gaacctgcag cagggcatct acctgctgcg ggaccacgtg atcaccctga    1860
tggaagccac cctgcacgac atcagcgtga tggaaggcat gttcgccgtg cagcacctgc    1920
acacccacct gaatcacctg aaaaccatgc tgctggaacg gcgcatcgac tggacctaca    1980
tgagcagcac ctggctgcag cagcagctgc agaaaagcga cgacgagatg aaggtgatca    2040
agcggatcgc cagatctctg gtgtactacg tgaagcagac ccacagcagc cccaccgcca    2100
ccgcctggga gatcggcctg tactatgagc tggtgatccc caagcacatc tacctgaaca    2160
actggaatgt ggtgaacatc ggccacctgg tgaaagcgc cggacagctg acccacgtga    2220
ccatcgccca ccctacgag atcatcaaca agaatgcgt ggagaccatc tatctgcacc    2280
tggaagattg cacccggcag gactacgtga tctgcgacgt ggtgaagatc gtgcagccct    2340
gcggcaacag cagcgacacc agcgactgcc ccgtgtgggc cgaggccgtg aaagaaccct    2400
tcgtgcaggt gaaccccctg aagaacggct cctacctggt gctggccagc agcaccgact    2460
gccagatccc ccctacgtg cccagcatcg tgaccgtgaa tgagaccacc tcctgcttcg    2520
gcctggactt caagcggccc ctggtggccg aggaaagact gagcttcgag ccccggctgc    2580
ccaacctgca gctgaggctg ccccacctgg tgggcatcat cgccaagatc aagggcatca    2640
agatcgaggt gaccagcagc ggcgagagca tcaaagaaca gatcgagcgg gccaaggccg    2700
agctgctgcg gctggatatc cacgagggcg acacacccgc ctggatccag cagctggccg    2760
ccgccaccaa ggacgtgtgg cccgctgcag ccagcgccct gcagggcatc ggcaactttc    2820
tgagcggcac cgcccagggc atcttcggca ccgccttctc cctgctgggc tacctgaagc    2880
ccatcctgat cggcgtgggc gtgattctgc tggtgattct gatcttcaag atcgtgagct    2940
ggatccccac caagaaaaag aaccagtgac tcgag    2975
```

<210> SEQ ID NO 41
<211> LENGTH: 2967
<212> TYPE: RNA
<213> ORGANISM: artificial sequence
<220> FEATURE:
<223> OTHER INFORMATION: Description of artificial sequence: Synthetic polynucleotide
<220> FEATURE:
<223> OTHER INFORMATION: FV_EM20_HCO_Seq

<400> SEQUENCE: 41

```
auggcccuc ccaugacccu gcagcagugg aucaucugga agaagaugaa caaggcccac     60
gaggcccugc agaacaccac caccgugacc gagcagcaga agagcagau cauccuggac    120 auccagaacg aggaagugca gcccaccagg cgggacaagu ucagauaccu gcuguacacc    180
ugcugcgcca ccuccagccg ggugcuggcc uggauguucc ugguguggca ucugcugauc    240 aucgucugg uguccugcuu cgugaccauc agccggaucc aguggaacaa ggacauccag    300
gugcugggcc ccgugaucga cuggaacgug acccagcggg ccgguaccca gccccugcag    360
acccggcgga ucgccggguc ccugcggaug cagcaccccg ugcccaagua cguggaggug    420
aacaugacca gcauccccca gggcgugua uacgagcccc accccgagcc caucguggug    480
aaagaaagag ugcuggggccu gagccagauc cugaugauca cagcgagaa caucgccaac    540 aacgccaacc ugacccagga agugaagaaa cugcugaccg agauggugaa cgaagagaug    600
cagagccuga gcgacgugau gaucgacuuc gagauccccc ugggcgaccc cagggaccag    660
```

-continued

```
gaacaguaca uccaccggaa gugcuaccag gaauuugcca acugcuaccu ggugaaguac    720
aaagagccca agcccuggcc caaagagggc cugaucgccg accagugccc ccugcccggc    780
uaucacgccg ccugaccua caaccggcag agcaucuggg acuacuacau caagguggag    840
agcaucaggc ccgccaacug gaccaccaag agcaaguacg ccaggcccg gcugggcagc    900 uucuacaucc ccagcagccu gcggcagauc aacgugagcc acgugcuguu cugcagcgac    960
cagcuguaca gcaaguggua caacaucgag aacaccaucg agcagaacga gcgguuccug   1020
cugaacaagc ugaauaaccu gaccagcggc accagcgugc ugaagaagag agcccugccc   1080
aaggacuggu ccagccaggg caagaacgcc cuguuccggg agaucaaugu gcuggacauc   1140
ugcagcaagc ccgagagcgu gauccugcug aauaccagcu acuacagcuu cagccugugg   1200
gagggcgacu gcaacuucac caaggacaug aucagcagc uggugcccga gugcgacggc   1260
uucuacaaca cuccaagugu gaugcacaug caccccuacg ccugccgguu cuggcggagc   1320
aagaacgaga agaggaaac caagugccgg gacggcgaga ccaagcggug ccuguacuac   1380
ccccugaggg acagcccuga gagcaccuac gacuucggcu accuggccua ccagaagaac   1440
uuccccagcc ccaucugcau cgaacagcag aagauccggg accaggacua cgagguguac   1500
agccuguacc aggaaugcaa gaucgccagc aaggccuacg gcaucgacac cgugcuguuc   1560
agccugaaga auuccugaa cuacaccggc accccguga cgagaugcc caacgccagg   1620 gccuucgugg gccugauuga ccccaaguuc ccccccagcu accccaacgu gacccgggag   1680
cacuacacca gcugcaacaa ccggaagcgg acuagcgugg acaacaacua cgccaagcug   1740
cggagcaugg gcuacgcucu gacaggcgcc gugcagaccc ugucccagau cagcgacauc   1800
aacgacgaga accugcagca gggcaucuac cugcugcggg accacgugau caccccugaug  1860 gaagccaccc ugcacgacau cagcgugaug gaaggcaugu cgccgugca gcaccugcac   1920 acccaccuga aucaccugaa aaccaugcug cuggaacggc gcaucgacug gaccuacaug   1980
agcagcaccu ggcugcagca gcagcugcag aaaagcgacg acgagaugaa ggugaucaag   2040
cggaucgcca gaucucuggu guacuacgug aagcagaccc acagcagccc caccgccacc   2100
gccugggaga ucgccuguga cuaugagcug gugauccca agcacaucua ccugaacaac   2160
uggaaugugg ugaacaucgg ccaccuggug aaaagcgccg acagcugac ccacgugacc   2220 aucgccaccc ccuacgagau caucaacaaa gaaugcgugg agaccaucua ucugcaccug   2280
gaagauugca cccggcagga cuacgugauc ugcgacgugg ugaagaucgu gcagcccugc   2340
ggcaacagca gcgacaccag cgacugcccc gugugggccg aggccgugaa agaacccuuc   2400 gugcaggguga accccugaa gaacggcucc uaccuggugc uggccagcag caccgacugc   2460 cagaucccc ccuacgugcc cagcaucgug accgugaaug agaccaccuc cugcuucggc   2520
cuggacuuca gcggcccccu ggugggcgag gaaagacuga gcuucgagcc ccggcugccc   2580
aaccugcagc ugaggcugcc ccaccuggug ggcaucaucg ccaagaucaa gggcaucaag   2640 aucgaggugga ccagcagcgg cgagagcauc aaagaacaga ucgagcgggc caaggccgag   2700
cugcugcggc uggauauucca cgagggcgac acacccgccu ggauccagca gcuggccgcc   2760
gccaccaagg acgugguggcc cgcugcagcc agcgcccugc agggcaucgg caacuuucug   2820
agcggcaccg cccagggcau cuucggcacc gccuucuccc ugcugggcua ccugaagccc   2880
auccugaucg gcgugggcgu gauucugcug gugauucuga ucuucaagau cgugagcugg   2940 aucccccacca agaaaaagaa ccaguga                                     2967
```

-continued

```
<210> SEQ ID NO 42
<211> LENGTH: 988
<212> TYPE: PRT
<213> ORGANISM: artificial sequence
<220> FEATURE:
<223> OTHER INFORMATION: Description of artificial sequence: Synthetic
      polypeptide
<220> FEATURE:
<223> OTHER INFORMATION: FV_EM20_HCO_Seq

<400> SEQUENCE: 42

Met Ala Pro Pro Met Thr Leu Gln Gln Trp Ile Ile Trp Lys Lys Met
1               5                   10                  15

Asn Lys Ala His Glu Ala Leu Gln Asn Thr Thr Thr Val Thr Glu Gln
            20                  25                  30

Gln Lys Glu Gln Ile Ile Leu Asp Ile Gln Asn Glu Glu Val Gln Pro
        35                  40                  45

Thr Arg Arg Asp Lys Phe Arg Tyr Leu Leu Tyr Thr Cys Cys Ala Thr
    50                  55                  60

Ser Ser Arg Val Leu Ala Trp Met Phe Leu Val Cys Ile Leu Leu Ile
65                  70                  75                  80

Ile Val Leu Val Ser Cys Phe Val Thr Ile Ser Arg Ile Gln Trp Asn
                85                  90                  95

Lys Asp Ile Gln Val Leu Gly Pro Val Ile Asp Trp Asn Val Thr Gln
            100                 105                 110

Arg Ala Val Tyr Gln Pro Leu Gln Thr Arg Arg Ile Ala Arg Ser Leu
        115                 120                 125

Arg Met Gln His Pro Val Pro Lys Tyr Val Glu Val Asn Met Thr Ser
    130                 135                 140

Ile Pro Gln Gly Val Tyr Tyr Glu Pro His Pro Glu Pro Ile Val Val
145                 150                 155                 160

Lys Glu Arg Val Leu Gly Leu Ser Gln Ile Leu Met Ile Asn Ser Glu
                165                 170                 175

Asn Ile Ala Asn Asn Ala Asn Leu Thr Gln Glu Val Lys Lys Leu Leu
            180                 185                 190

Thr Glu Met Val Asn Glu Met Gln Ser Leu Ser Asp Val Met Ile
        195                 200                 205

Asp Phe Glu Ile Pro Leu Gly Asp Pro Arg Asp Gln Glu Gln Tyr Ile
    210                 215                 220

His Arg Lys Cys Tyr Gln Glu Phe Ala Asn Cys Tyr Leu Val Lys Tyr
225                 230                 235                 240

Lys Glu Pro Lys Pro Trp Pro Lys Glu Gly Leu Ile Ala Asp Gln Cys
                245                 250                 255

Pro Leu Pro Gly Tyr His Ala Gly Leu Thr Tyr Asn Arg Gln Ser Ile
            260                 265                 270

Trp Asp Tyr Tyr Ile Lys Val Glu Ser Ile Arg Pro Ala Asn Trp Thr
        275                 280                 285

Thr Lys Ser Lys Tyr Gly Gln Ala Arg Leu Gly Ser Phe Tyr Ile Pro
    290                 295                 300

Ser Ser Leu Arg Gln Ile Asn Val Ser His Val Leu Phe Cys Ser Asp
305                 310                 315                 320

Gln Leu Tyr Ser Lys Trp Tyr Asn Ile Glu Asn Thr Ile Glu Gln Asn
                325                 330                 335

Glu Arg Phe Leu Leu Asn Lys Leu Asn Asn Leu Thr Ser Gly Thr Ser
            340                 345                 350
```

```
Val Leu Lys Arg Ala Leu Pro Lys Asp Trp Ser Gln Gly Lys
        355                 360                 365
Asn Ala Leu Phe Arg Glu Ile Asn Val Leu Asp Ile Cys Ser Lys Pro
    370                 375                 380
Glu Ser Val Ile Leu Leu Asn Thr Ser Tyr Tyr Ser Phe Ser Leu Trp
385                 390                 395                 400
Glu Gly Asp Cys Asn Phe Thr Lys Asp Met Ile Ser Gln Leu Val Pro
                405                 410                 415
Glu Cys Asp Gly Phe Tyr Asn Asn Ser Lys Trp Met His Met His Pro
                420                 425                 430
Tyr Ala Cys Arg Phe Trp Arg Ser Lys Asn Glu Lys Glu Glu Thr Lys
        435                 440                 445
Cys Arg Asp Gly Glu Thr Lys Arg Cys Leu Tyr Tyr Pro Leu Trp Asp
450                 455                 460
Ser Pro Glu Ser Thr Tyr Asp Phe Gly Tyr Leu Ala Tyr Gln Lys Asn
465                 470                 475                 480
Phe Pro Ser Pro Ile Cys Ile Glu Gln Gln Lys Ile Arg Asp Gln Asp
                485                 490                 495
Tyr Glu Val Tyr Ser Leu Tyr Gln Glu Cys Lys Ile Ala Ser Lys Ala
                500                 505                 510
Tyr Gly Ile Asp Thr Val Leu Phe Ser Leu Lys Asn Phe Leu Asn Tyr
        515                 520                 525
Thr Gly Thr Pro Val Asn Glu Met Pro Asn Ala Arg Ala Phe Val Gly
        530                 535                 540
Leu Ile Asp Pro Lys Phe Pro Pro Ser Tyr Pro Asn Val Thr Arg Glu
545                 550                 555                 560
His Tyr Thr Ser Cys Asn Asn Arg Lys Arg Thr Ser Val Asp Asn Asn
                565                 570                 575
Tyr Ala Lys Leu Arg Ser Met Gly Tyr Ala Leu Thr Gly Ala Val Gln
        580                 585                 590
Thr Leu Ser Gln Ile Ser Asp Ile Asn Asp Glu Asn Leu Gln Gln Gly
        595                 600                 605
Ile Tyr Leu Leu Arg Asp His Val Ile Thr Leu Met Glu Ala Thr Leu
610                 615                 620
His Asp Ile Ser Val Met Glu Gly Met Phe Ala Val Gln His Leu His
625                 630                 635                 640
Thr His Leu Asn His Leu Lys Thr Met Leu Leu Glu Arg Arg Ile Asp
            645                 650                 655
Trp Thr Tyr Met Ser Ser Thr Trp Leu Gln Gln Gln Leu Gln Lys Ser
            660                 665                 670
Asp Asp Glu Met Lys Val Ile Lys Arg Ile Ala Arg Ser Leu Val Tyr
        675                 680                 685
Tyr Val Lys Gln Thr His Ser Ser Pro Thr Ala Thr Ala Trp Glu Ile
        690                 695                 700
Gly Leu Tyr Tyr Glu Leu Val Ile Pro Lys His Ile Tyr Leu Asn Asn
705                 710                 715                 720
Trp Asn Val Val Asn Ile Gly His Leu Val Lys Ser Ala Gly Gln Leu
                725                 730                 735
Thr His Val Thr Ile Ala His Pro Tyr Glu Ile Ile Asn Lys Glu Cys
                740                 745                 750
Val Glu Thr Ile Tyr Leu His Leu Glu Asp Cys Thr Arg Gln Asp Tyr
            755                 760                 765
Val Ile Cys Asp Val Val Lys Ile Val Gln Pro Cys Gly Asn Ser Ser
```

```
Asp Thr Ser Asp Cys Pro Val Trp Ala Glu Ala Val Lys Glu Pro Phe
785                 790                 795                 800

Val Gln Val Asn Pro Leu Lys Asn Gly Ser Tyr Leu Val Leu Ala Ser
                805                 810                 815

Ser Thr Asp Cys Gln Ile Pro Pro Tyr Val Pro Ser Ile Val Thr Val
            820                 825                 830

Asn Glu Thr Thr Ser Cys Phe Gly Leu Asp Phe Lys Arg Pro Leu Val
            835                 840                 845

Ala Glu Glu Arg Leu Ser Phe Glu Pro Arg Leu Pro Asn Leu Gln Leu
        850                 855                 860

Arg Leu Pro His Leu Val Gly Ile Ile Ala Lys Ile Lys Gly Ile Lys
865                 870                 875                 880

Ile Glu Val Thr Ser Ser Gly Glu Ser Ile Lys Glu Gln Ile Glu Arg
                885                 890                 895

Ala Lys Ala Glu Leu Leu Arg Leu Asp Ile His Glu Gly Asp Thr Pro
            900                 905                 910

Ala Trp Ile Gln Gln Leu Ala Ala Ala Thr Lys Asp Val Trp Pro Ala
        915                 920                 925

Ala Ala Ser Ala Leu Gln Gly Ile Gly Asn Phe Leu Ser Gly Thr Ala
        930                 935                 940

Gly Gly Ile Phe Gly Thr Ala Phe Ser Leu Leu Gly Tyr Leu Lys Pro
945                 950                 955                 960

Ile Leu Ile Gly Val Gly Val Ile Leu Leu Val Ile Leu Ile Phe Lys
                965                 970                 975

Ile Val Ser Trp Ile Pro Thr Lys Lys Lys Asn Gln
            980                 985
```

<210> SEQ ID NO 43
<211> LENGTH: 3924
<212> TYPE: DNA
<213> ORGANISM: artificial sequence
<220> FEATURE:
<223> OTHER INFORMATION: Description of artificial sequence: Synthetic
      polynucleotide
<220> FEATURE:
<223> OTHER INFORMATION: FV_Geno_Seq-GFP (3924 bp)

<400> SEQUENCE: 43

```
ccatgggagc tcttcactac tcgctgcgtc gagagtgtac gagactctcc aggtttggta     60
agaaatattt tatattgtta taatgttact atgatccatt aacactctgc ttatagattg    120
taagggtgat tgcaatgctt tctgcataaa actttggttt tcttgttaat caataaaccg    180
acttgattcg agaacctact catatattat tgtctctttt atactttatt aagtaaaagg    240
atttgtatat tagccttgct aagggagaca tctagtgata taagtgtgaa ctacacttat    300
cttaaatgat gtaactcctt aggataatca atatacaaaa ttccatgaca attggcgccc    360
aacgtggggc tcgaatataa gtcgggttta tttgtaaatt atccctaggg acctccgagc    420
atagcgggag gcatataaaa gccaatagac actggcttaa ggaagtaatg ttgaagaata    480
tgaacttgat gttgaagctc tggttgtaat tttaagagat agaaatatac caagaaatcc    540
tttacatgga gaagttatag gtcttcgcct tactgaagga tggtggggac aaattgagag    600
atttcagatg gtacgtctaa tattacaaga tgatgataat gaacctttac agagacctta    660
attaaggcta tggatttggc cttgggacaa gaaattattg tttatagtcc cattgtatct    720
atgactaaaa tacaaaaaac tccactacca gaaagaaaag ctttacccat tagatggata    780
```

```
acatggatga cttatttaga agatccaaga atccaatttc attatgataa aaccttacca    840
gaacttaagc atattccaga tgtatataca tctagtcagt ctcctgttaa acatccttct    900
caatatgaag gagtgtttta tactgatggc tcggccatca aaagtcctga tcctacaaaa    960
agcaataatg ctggcatggg aatagtacat gccacataca aacctgaata tcaagttttg   1020
aatcaatggt caataccact aggtaatcat actgctcaga tggctgaaat agctgcagtt   1080
gaatttgcct gtaaaaaagc tttaaaaata cctggtcctg tattagttat aactgatagt   1140
ttctatgtag cagaaagtgc taataaagaa ttaccatact ggaaatctaa tgggtttgtt   1200
aataataaga aaaagcctct taaacatatc tccaaatgga aatctattgc tgagtgttta   1260
tctatgaaac cagacattac tattcaacat gaaaaaggca tcagcctaca aataccagta   1320
ttcatactga aaggcaatgc cctagcagat aagcttgcca cccaaggaag ttatgtggtt   1380
aattgtaata ccaaaaaacc aaacctggat gcagagttgg atcaattatt acagggtcat   1440
tatataaaag gattattgga cctttgccac cttcacaggg ataccatata tgattagtag   1500
ttgttgatgg aatgacagga ttcacttggt tatacccccac taaggctcct tctactagcg   1560
caactgttaa atctctcaat gtactcacta gtattgcaat tccaaaggtg attcactctg   1620
atcaaggtgc agcattcact tcttcaacct ttgctgaatg ggcaaaggaa agaggtatac   1680
atttggaatt cagtactcct tatcaccccc aaagtggtag taaggtggaa aggaaaaata   1740
gtgatataaa acgacttta actaaactgc tagtaggaag acccacaaag tggtatgacc   1800
tattgcctgt tgtacaactt gctttaaaca cacctatag ccctgtatta aaatatactc   1860
cacatcaact cttatttggt atagattcaa atactccatt tgcaaatcaa gatacacttg   1920
acttgaccag agaagaagaa ctttctcttt tacaggaaat tcgtacttct ttataccatc   1980
catccacccc tccagcctcc tctcgttcct ggtctcctgt tgttggccaa ttggtccagg   2040
agagggtggc taggcctgct tctttgagac ctcgttggca taaaccgtct actgtactta   2100
agagtcgacc tagctgcagt aacgccattt tgcaaggcat ggaaaaatac caaaccaaga   2160
atagagaagt tcagatcaag ggcgggtaca tgaaaatagc taacgttggg ccaaacagga   2220
tatctgcggt gagcagtttc ggccccggcc cggggccaag aacagatggt caccgcagtt   2280
tcggccccgg cccgaggcca agaacagatg tccccagat atggcccaac cctcagcagt   2340
ttcttaagac ccatcagatg tttccaggct cccccaagga cctgaaatga ccctgcgcct   2400
tatttgaatt aaccaatcag cctgcttctc gcttctgttc gcgcgcttct gcttcccgag   2460
ctctataaaa gagctcacaa ccctcactc ggcgcgccag tcctccgaca gactgagtct   2520
acgtagccac gatggtgagc aagggcgagg agctgttcac cggggtggtg cccatcctgg   2580
tcgagctgga cggcgacgta aacggccaca agttcagcgt gtccggcgag ggcgagggcg   2640
atgccaccta cggcaagctg accctgaagt tcatctgcac caccggcaag ctgcccgtgc   2700
cctggcccac cctcgtgacc accctgacct acggcgtgca gtgcttcagc cgctaccccg   2760
accacatgaa gcagcacgac ttcttcaagt ccgccatgcc cgaaggctac gtccaggagc   2820
gcaccatctt cttcaaggac gacggcaact acaagacccg cgccgaggtg aagttcgagg   2880
gcgacaccct ggtgaaccgc atcgagctga agggcatcga cttcaaggag gacggcaaca   2940
tcctggggca aagctggag tacaactaca acagccacaa cgtctatatc atggccgaca   3000
agcagaagaa cggcatcaag gtgaacttca agatccgcca caacatcgag gacggcagcg   3060
tgcagctcgc cgaccactac cagcagaaca ccccatcgg cgacggcccc gtgctgctgc   3120
```

| | |
|---|---:|
| ccgacaacca ctacctgagc acccagtccg ccctgagcaa agaccccaac gagaagcgcg | 3180 |
| atcacatggt cctgctggag ttcgtgaccg ccgccgggat cactctcggc atggacgagc | 3240 |
| tgtacaagta agctagctgg cagcctcgac tgtgccttct agttgccagc catctgttgt | 3300 |
| ttgcccctcc cccgtgcctt ccttgaccct ggaaggtgcc actcccactg tcctttccta | 3360 |
| ataaaatgag gaaattgcat cgcattgtct gagtaggtgt cattctattc tggggggtgg | 3420 |
| ggtggggcag gacagcaagg gggaggattg gaagacaat agcaggcatg ctggggatgc | 3480 |
| ggtgggctct atggacgcgt tgtggtggaa tgccactaga aactagggaa aactaggagg | 3540 |
| agagtattac agggaaggaa gtgaagaacc tcgtgaccca atactcctg ctcctcatag | 3600 |
| acgtacctgg gatgagagac acaaggttct taaattgtcc tcattcgcta ctccctctga | 3660 |
| catccaacgc tgggctacta aagcattgcc ttatggctgg aaagtggtca cttgtacggg | 3720 |
| agctcttcac tactcgctgc gtcgagagtg tacgagactc tccaggtttg gtaagaaata | 3780 |
| ttttatattg ttataatgtt actatgatcc attaacactc tgcttataga ttgtaagggt | 3840 |
| gattgcaatg ctttctgcat aaaactttgg ttttcttgtt aatcaataaa ccgacttgat | 3900 |
| tcgagaacct accagctgct cgag | 3924 |

<210> SEQ ID NO 44
<211> LENGTH: 3918
<212> TYPE: RNA
<213> ORGANISM: artificial sequence
<220> FEATURE:
<223> OTHER INFORMATION: Description of artificial sequence: Synthetic
      polynucleotide
<220> FEATURE:
<223> OTHER INFORMATION: FV_Geno_Seq-GFP (3924 bp)

<400> SEQUENCE: 44

| | |
|---|---:|
| gagcucuuca cuacucgcug cgucgagagu guacgagacu cuccagguuu gguaagaaau | 60 |
| auuuuauauu guuauaaugu uacuaugauc cauuaacacu cugcuuauag auuguaaggg | 120 |
| ugauugcaau gcuuucugca uaaaacuuug guuuucuugu uaaucaauaa accgacuuga | 180 |
| uucgagaacc uacucauaua uuauugucuc uuuuauacuu uauuaaguaa aaggauuugu | 240 |
| auauuagccu ugcuaaggga gacaucuagu gauauaagug uaacuacac uuaucuuaaa | 300 |
| ugauguaacu ccuuaggaua aucaauauac aaaauuccau gacaauuggc gcccaacgug | 360 |
| gggcucgaau auaagucggg uuuauuugua auuuaucccu agggaccucc gagcauagcg | 420 |
| ggaggcauau aaaagccaau agacacuggc uuaaggaagu aauguugaag aauaugaacu | 480 |
| ugauguugaa gcucuggung uaauuuuaag agauagaaau auaccaagaa auccuuuaca | 540 |
| uggagaaguu auaggucuuc gccuuacuga aggauggugg ggacaaauug agagauuuca | 600 |
| gauggucacgu cuaauauuac aagaugauga uaaugaaccu uuacagagac cuuauuaag | 660 |
| gcuauggauu uggccuuggg acaagaaaua uuaguuuaua gucccauugu aucuaugacu | 720 |
| aaaaucacaaa aaacuccacu accagaaaga aagcuuuac ccauuagaug gauaacaugg | 780 |
| augacuuauu uagaagaucc aagaauccaa uuucauuaug auaaaaccuu accagaacuu | 840 |
| aagcauauuc cagauguaua uacaucuagu cagucuccug uuaacaucc uucucaauau | 900 |
| gaaggagugu uuuauacuga uggcucggcc aucaaaaguc cugauccuac aaaaagcaau | 960 |
| aaugcuggca ugggaauagu acaugccaca uacaaaccug aauaucaagu uuugaaucaa | 1020 |
| uggucaauac cacuaggaa ucauacgcu cagauggcg aaauagcgc aguugaauuu | 1080 |
| gccuguaaaa aagcuuuaaa aauaccuggu ccuguauuag uuauaacuga uaguuucuau | 1140 |

```
guagcagaaa gugcuaauaa agaauuacca uacuggaaau cuauggguu uguuaauaau     1200 aagaaaaagc cucuuaaaca uaucuccaaa uggaaaucua ugcugagug uuuaucuaug     1260 aaaccagaca uuacuauuca acaugaaaaa ggcaucagcc uacaaauacc aguauucaua    1320
cugaaaggca augcccuagc agauaagcuu gccacccaag gaaguuaugu gguuaauugu    1380
aauaccaaaa aaccaaaccu ggaugcagag uuggaucaau uauuacaggg ucauuauaua    1440
aaaggauuau uggaccuuug ccaccuucac agggauaccu auauguauua guaguuguug    1500
auggaaugac aggauucacu ugguuauacc ccacuaaggc uccuucuacu agcgcaacug    1560
uuaaaucucu caauguacuc acuaguauug caauuccaaa ggugauucac ucugaucaag    1620
gugcagcauu cacuucuuca accuuugcug aaugggcaaa ggaaagaggu auacauuugg    1680
aauucaguac uccuuaucac ccccaaagug guaguaaggu ggaaaggaaa aauagugaua    1740
uaaaacgacu uuuaacuaaa cugcuaguag gaagacccac aaagugguau gaccuauugc    1800
cuguuguaca acugcuuuua aacaacaccu auagcccugu auuaaaauau acuccacauc    1860
aacucuuauu ugguauagau ucaaauacuc cauuugcaaa ucaagauaca cuugacuuga    1920
ccagagaaga agaacuuucu cuuuuacagg aaauucguac uucuuuauac cauccaucca    1980
ccccuccagc cucucucgu uccuggucuc cuguuguugg ccaaugguc caggagaggg      2040 uggcuaggcc ugcuucuuug agaccucguu ggcauaaacc gucuacugua cuuaagaguc    2100
gaccuagcug caguaacgcc auuuugcaag gcauggaaaa auaccaaacc aagaauagag    2160
aaguucagau caagggcggg uacaugaaaa uagcuaacgu ugggccaaac aggauaucug    2220
cggugagcag uuucggcccc ggcccggggc caagaacaga uggucaccgc aguucggcc     2280 ccggcccgag gccaagaaca gauggucccc agauauggcc caacccucag caguuucuua    2340
agacccauca gauguuucca ggcucccca aggaccugaa augacccugc gccuauuug      2400 aauuaaccaa ucagccugcu ucucgcuucu guucgcgcgc uucugcuucc cgagcucuau    2460
aaaagagcuc acaacccuc acucggcgcg ccagccucc gacagacuga gucuacuag      2520 ccacgauggu gagcaagggc gaggagcugu uccggggu ggugcccauc cuggucgagc      2580
uggacggcga cguaaacggc cacaaguuca gcguguccgg cgaggcgag ggcgaugcca     2640 ccuacggcaa gcugacccug aaguucaucu gcaccaccgg caagcugccc gugcccuggc    2700
ccacccucgu gacccccug accuacggcg ugcagugcuu cagccgcuac cccgaccaca    2760
ugaagcagca cgacuucuuc aaguccgcca ugcccgaagg cuacguccag gagcgcacca    2820
ucuucuucaa ggacgacggc aacuacaaga cccgcgccga ggugaaguuc gagggcgaca    2880
cccuggugaa ccgcaucgag cugaagggca ucgacuucaa ggaggacggc aacauccugg    2940
ggcacaagcu ggaguacaac uacaacagcc acaacgucua uaucauggcc gacaagcaga    3000
agaacggcau caaggugaac uucaagaucc gccacaacau cgaggacggc agcgugcagc    3060
ucgccgacca cuaccagcag aacaccccca ucggcgacgg ccccgugcug cugcccgaca    3120
accacuaccu gagcacccag uccgcccuga gcaaagaccc caacgagaag cgcgaucaca    3180
ugguccugcu ggaguucgug accgccgccg ggaucacucu cggcauggac gagcuguaca    3240
aguaagcuag cuggcagccu cgacugugcc uucuaguugc cagccaucug uuguuugccc    3300
cucccccgug ccuuccuuga cccuggaagg ugccacuccc acuguccuuu ccuaauaaaa    3360
ugaggaaauu gcaucgcauu gucugaguag gugucauucu auucgggggu gggggugggg    3420
gcaggacagc aaggggggagg auuggaaga caauagcagg caugcugggg augcggugggg   3480 cucuauggac gcguuguggu ggaaugccac uagaaacuag gaaaacuag gaggagagua    3540
```

```
uuacagggaa ggaagugaag aaccucguga cccaaauacu ccugcuccuc auagacguac      3600 cuggaugag agacacaagg uucuuaaauu guccucauuc gcuacucccu cugacaucca       3660
acgcugggcu acuaaagcau ugccuuaugg cuggaaagug gucacuugua cgggagcucu     3720
ucacuacucg cugcgucgag aguguacgag acucuccagg uuugguaaga aauauuuuau     3780
auuguuauaa uguuacuaug auccauuaac acucugcuua uagauuguaa gggugauugc     3840
aaugcuuucu gcauaaaacu uugguuuucu uguuaaucaa uaaaccgacu ugauucgaga     3900
accuaccagc ugcucgag                                                   3918
```

<210> SEQ ID NO 45
<211> LENGTH: 239
<212> TYPE: PRT
<213> ORGANISM: artificial sequence
<220> FEATURE:
<223> OTHER INFORMATION: Description of artificial sequence: Synthetic polypeptide
<220> FEATURE:
<223> OTHER INFORMATION: GFP

<400> SEQUENCE: 45

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 46
<211> LENGTH: 3918
<212> TYPE: RNA
<213> ORGANISM: artificial sequence
<220> FEATURE:

<223> OTHER INFORMATION: Description of artificial sequence: Synthetic
      polynucleotide
<220> FEATURE:
<223> OTHER INFORMATION: FV_Geno_Seq-GFP v2

<400> SEQUENCE: 46
gagcucuuca cuacucgcug cgucgagagu guacgagacu cuccagguuu gguaagaaau 60
auuuuauauu guuauaaugu uacuaugauc cauuaacacu cugcuuauag auuguaaggg 120
ugauugcaau gcuuucugca uaaaacuuug guuuucuugu uaaucaauaa accgacuuga 180
uucgagaacc uacucauaua uuauugucuc uuuuauacuu uauuaaguaa aaggauuugu 240
auauuagccu ugcuaaggga gacaucuagu gauauaagug ugaacuacac uuaucuuaaa 300
ugauguaacu ccuuaggaua aucaauauac aaaauuccau gacaauuggc gcccaacgug 360
gggcucgaau auaagucggg uuuauuugua aauuaucccu agggaccucc gagcauagcg 420
ggaggcauau aaaagccaau agacacuggc uuaaggaagu aauguugaag aauaugaacu 480
ugauguugaa gcucugguug uaauuuuaag agauagaaau auaccaagaa auccuuuaca 540
uggagaaguu auaggucuuc gccuuacuga aggauggugg ggacaaauug agagauuuca 600
gaugguacgu cuaauauuac aagaugauga uaaugaaccu uuacagagac cuuaauuaag 660
gcuauggauu uggccuuggg acaagaaaua uuaguuuaua gucccauugu aucuaugacu 720
aaaauacaaa aaacuccacu accagaaaga aaagcuuuac ccauuagaug gauaacaugg 780
augacuuauu uagaagaucc aagaauccaa uuucauuaug auaaaaccuu accagaacuu 840
aagcauauuc cagauguaua uacaucuagu cagucuccug uuaaacaucc uucucaauau 900
gaaggagugu uuuauacuga uggcucggcc aucaaaaguc cugauccuac aaaaagcaau 960
aaugcuggca ugggaauagu acaugccaca uacaaaccug aauaucaagu uuugaaucaa 1020
uggucaauac cacuagguaa ucauacugcu cagauggcug aaauagcugc aguugaauuu 1080
gccuguaaaa aagcuuuaaa aauaccuggu ccuguauuag uuauaacuga uaguuucuau 1140
guagcagaaa gugcuaauaa agaauuacca uacuggaaau cuaaugggUu uguuaauaau 1200
aagaaaaagc cucuuaaaca uaucuccaaa uggaaaucua uugcugagug uuuaucuaug 1260
aaaccagaca uuacuauuca acaugaaaaa ggcaucagcc uacaaauacc aguauucaua 1320
cugaaaggca augcccuagc agauaagcuu gccacccaag gaaguuaugu gguuaauugu 1380
aauaccaaaa aaccaaaccu ggaugcagag uuggaucaau uauuacaggg ucauuauaua 1440
aaaggauuau uggaccuuug ccaccuucac agggauaccu auauguauua guaguuguug 1500
auggaaugac aggauucacu ugguuauacc ccacuaaggc uccuucuacu agcgcaacug 1560
uuaaaucucu caauguacuc acuaguauug caauuccaaa ggugauucac ucugaucaag 1620
gugcagcauu cacuucuuca accuuugcug aaugggcaaa ggaaagaggu auacauuugg 1680
aauucaguac uccuuaucac ccccaaagug guaguaaggu ggaaaggaaa aauagugaua 1740
uaaaacgacu uuuaacuaaa cugcuaguag gaagacccac aaagugguau gaccuauugc 1800
cuguuguaca acuugcuuua aacaacaccu auagcccugu auuaaaaauau acuccacauc 1860 aacucuuauu ugguauagau ucaaauacuc cauuugcaaa ucaagauaca cuugacuuga 1920
ccagagaaga agaacuuucu cuuuuacagg aaauucguac uucuuuauac cauccaucca 1980
ccccuccagc cuccucucgu uccuggucuc cuguuguugg ccaauugguc caggagaggg 2040
uggcuaggcc ugcuucuuug agaccucguu ggcauaaacc gucuacugua cuuaagaguc 2100
gaccuagcug caguaacgcc auuuugcaag gcauggaaaa auaccaaacc aagaauagag 2160

```
aaguucagau caagggcggg uacaugaaaa uagcuaacgu ugggccaaac aggauaucug    2220
cggugagcag uuucggcccc ggcccggggc caagaacaga uggucaccgc aguuucggcc    2280
ccggcccgag gccaagaaca gaugguccc agauauggcc caacccucag caguuucuua    2340
agacccauca gauguuucca ggcuccccca aggaccugaa augacccugc gccuuauuug    2400
aauuaaccaa ucagccugcu ucucgcuucu guucgcgcgc uucugcuucc cgagcucuau    2460
aaaagagcuc acaaccccuc acucggcgcg ccaguccucc gacagacuga gucuacguag    2520
ccacgauggu gagcaagggc gaggagcugu ucaccggggu ggugcccauc cuggucgagc    2580
uggacggcga cguaaacggc cacaaguuca gcguguccgg cgagggcgag ggcgaugcca    2640
ccuacggcaa gcugacccug aaguucaucu gcaccaccgg caagcugccc gugcccuggc    2700
ccacccucgu gaccacccug accuacggcg ugcagugcuu cagccgcuac cccgaccaca    2760
ugaagcagca cgacuucuuc aaguccgcca ugcccgaagg cuacguccag gagcgcacca    2820
ucuucuucaa ggacgacggc aacuacaaga cccgcgccga ggugaaguuc gagggcgaca    2880
cccuggugaa ccgcaucgag cugaagggca ucgacuucaa ggaggacggc aacauccugg    2940
ggcacaagcu ggaguacaac uacaacagcc acaacgucua uaucauggcc gacaagcaga    3000
agaacggcau caaggugaac uucaagaucc gccacaacau cgaggacggc agcgugcagc    3060
ucgccgacca cuaccagcag aacacccca ucggcgacgg ccccgugcug cugcccgaca    3120
accacuaccu gagcacccag uccgcccuga gcaaagaccc caacgagaag cgcgaucaca    3180
ugguccugcu ggaguucgug accgccgccg ggaucacucu cggcauggac gagcuguaca    3240
aguaagcuag cuggcagccu cgacugugcc uucuaguugc cagccaucug uuguugccc    3300 cuccccgug ccuuccuuga cccuggaagg ugccacuccc acugucccu ccuaauaaaa    3360 ugaggaaauu gcaucgcauu gucugaguag gugucauucu auucggggg gugggguggg    3420 gcaggacagc aagggggagg auugggaaga caauagcagg caugcugggg augcgguggg    3480
cucuauggac gcguuguggu ggaaugccac uagaaacuag ggaaaacuag gaggagagua    3540
uuacagggaa ggaagugaag aaccucguga cccaaauacu ccugcuccuc auagacguac    3600
cugggaugag agacacaagg uucuuaaauu guccucauuc gcuacucccu cugacaucca    3660
acgcugggcu acuaaagcau ugccuuaugg cuggaaagug gucacuugua cgggagcucu    3720
ucacuacucg cugcgucgag aguguacgag acucuccagg uuuugguaaga aauauuuuau    3780 auuguuauaa uguuacuaug auccauuaac acucugcuua uagauuguaa gggugauugc    3840
aaugcuuucu gcauaaaacu uuggguuucu uguuaaucaa uaaaccgacu ugauucgaga    3900
accuaccagc ugcucgag                                                  3918
```

RNA BASED METHOD TO OBTAIN STABLY INTEGRATED RETROVIRAL VECTORS

SEQUENCE LISTING

The instant application contains a Sequence Listing which has been submitted electronically in ASCII format and is hereby incorporated by reference in its entirety. Said ASCII copy, created on Feb. 29, 2016, is named P81312653_US00_Sequence_listing.txt and is 250,255 bytes in size.

FIELD OF THE INVENTION

The present invention relates to a viral transformation method, particularly foamy virus-mediated transformation method. The present invention relates to the stable transfer of transgene into cells by the transient transfection of RNA encoding foamy vector components. The present invention has therefore therapeutic or prophylactic interest, especially in the field of gene therapy.

BACKGROUND OF THE INVENTION

Retroviruses are RNA viruses that replicate through a DNA intermediate. This large family of viruses is found to infect all vertebrates and includes gammaretroviruses, lentiviruses and spumaviruses. Currently, replication-deficient vectors derived from gammaretroviruses or lentiviruses represent the most frequently used tool for stable viral gene transfer. These vectors have a reasonable genetic payload (up to 9 kb), high transducing efficiencies both in vitro and in vivo, and the ability to permanently modify the genetic content of the target cell. Classically, retroviral vector production involves either transient transfection of multiple DNA plasmids encoding required components for viral packaging or alternatively the use of a packaging cell line which stably expresses the proteins required for viral assembly. In both cases, the manipulated cells produce viral particles that are subsequently recovered in the cell supernatant. Although both of these approaches permit production of functional viral vectors, the titers obtained are relatively low, making it difficult to scale production and efficiently obtain large titers. In addition, current processes are often laborious, time consuming and lack robustness. Thus, there is a need for a method to obtain cells containing stably integrated retroviral vectors without the need to pass by a discrete viral vector production process.

Spumaviruses or Foamy viruses (FV) are a subfamily of retroviruses that are endemic to most non-human primates, horses, cattle and cats (Saib 2003; Switzer, Salemi et al. 2005). The foamy virus (FV) replication pathway has been shown to differ from the classical retroviral pathway. FV infection starts with attachment to target cells and binding to an, as yet unknown, but potentially very ubiquitous cellular receptor. Upon arrival of capsids into the cytoplasm, they seem to dock to dynein motor protein complexes and migrate along microtubules towards the microtubule organizing center (MTOC) where they accumulate. Further, the disassembly apparently involving capsid processing by viral and cellular proteases occurs. Before the viral integration, the FV pre-integration complex is localized in the nucleus. Expression of FV genes by the cellular transcription machinery is regulated through a viral transactivator utilizing internal and LTR derived promoter elements. Then, spliced RNAs are exported out of nucleus and FV accessory, capsid and enzymatic genes are translated in the cytoplasm, whereas envelope glycoproteins are translated at the rough ensoplasmatic reticulum to target the secretory pathway. The FV assembly involves transport of Gag to the MTOC where a preassembly of capsids takes place. Unlike orthoretrovirus (a subfamily including gammaretroviruses and lentiviruses), FVs reverse transcribe their encapsidated RNA genome during assembly and/or budding, leading to the production of DNA containing virions. The ability to generate cDNA before budding of the virion has been shown to allow recycling of the genome into the nucleus resulting in intracellular retrotransposition (Heinkelein, Pietschmann et al. 2000; Pietschmann, Zentgraf et al. 2000). In addition, viral particles can also be released into the environment, or transferred by a cell-to-cell mechanism (Heinkelein, Pietschmann et al. 2000; Pietschmann, Zentgraf et al. 2000) (See FIG. 1).

Although foamy viruses were only more recently introduced into the repertoire of vector systems for the correction of inherited diseases (in particular the hematopoietic lineage in mammals) they represent an attractive alternative to gammaretroviruses and lentiviruses, displaying several additional advantages including the absence of FV antibodies in the human population, the benign course of natural FV infections, their very broad host cell range, a safer (i.e. more random) integration profile and an extended packaging limit (12 kb) (Lindemann and Rethwilm 2011).

SUMMARY OF THE INVENTION

Figure 2:
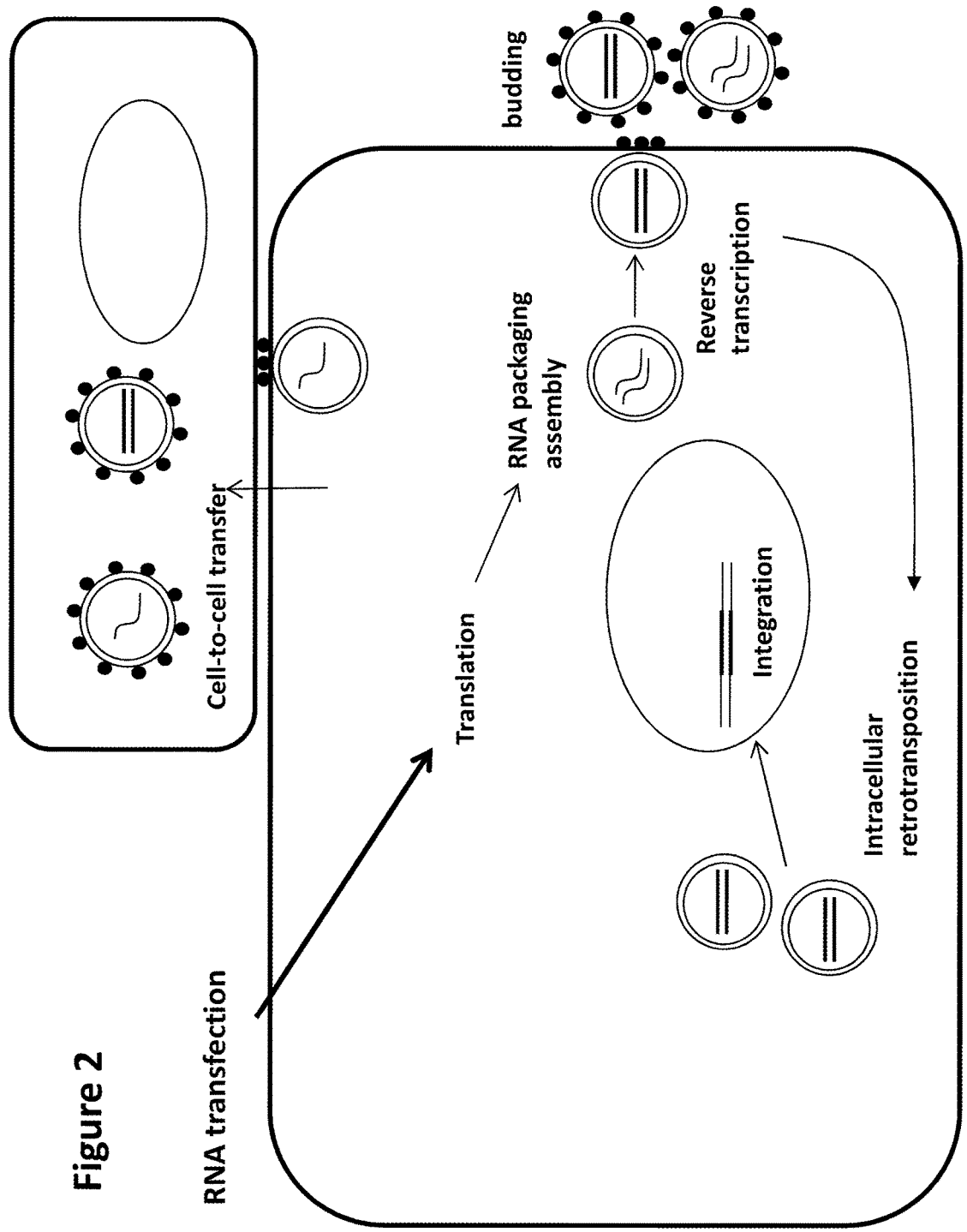

The FV replication pathway differs from the classical retroviral pathway in that the packaged RNA genome can be reverse transcribed after capsid assembly, allowing recycling of the genome into the nucleus and integration through intracellular retrotransposition. Therefore, to obtain stably integrated viral vectors without the need to produce cell-free supernatant, the inventors propose to directly introduce into desired cells or cell lines RNAs encoding gag, pol, FV genomic RNA comprising a desired transgene. Cells that express all three elements will be capable of incorporating the FV genome into a capsid, reverse-transcribing the genome into double-stranded DNA and then stably integrating the FV genome including the desired transgene without the need of obtaining vector through cell-free supernatant (FIG. 2).

Furthermore, there is evidence that efficient retrotransposition can occur in the presence of envelope mutants containing a mutation at the surface (SU)-transmembrane (TM) protein cleavage site that are fusion deficient and thus disabled in virus infection in cell free supernatant (Heinkelein, Pietschmann et al. 2000; Heinkelein, Rammling et al. 2003). Thus, the additional incorporation of RNA for such an envelope mutant (i.e. Arg571->Thr 571) would also allow the stable genetic transfer of the FV genome without the need of obtaining vector through cell-free supernatant.

Alternatively, RNA encoding wild-type envelope protein can be introduced into the cell. In this case infectious viral particles will be produced at a low level by transfected cells, potentially further increasing levels of stable gene transfer.

The RNA encoding Gag, Pol protein, the FV genomic RNA comprising a desired transgene, and optionally the RNA encoded Env protein are preferably electroporated in the cell.

Lastly, the RNA transfection of viral coding sequences will ensure a transient expression of viral proteins and, at the same time, a null risk for integration of viral ORFs. This will in turn abolish the risks of generation of replication competent recombinant vectors that could otherwise be generated through recombination in producer cell lines. Furthermore, the use of a mutant envelope can increase the safety of the viral vector production process.

Other advantages also arise with respect to therapeutic applications. In contrast to plasmids, the vector genomic RNA according to the invention cannot self-replicate and does not contain additional sequences other than those needed for efficient transgene integration. In addition, RNAs are more easily produced under GMP (good manufacturing practices) than plasmids, since these later require cloning and host cell techniques. The present invention has therefore therapeutic interest, especially in the field of gene therapy.

BRIEF DESCRIPTION OF THE FIGURES AND TABLES

In addition to the preceding features, the invention further comprises other features which will emerge from the description which follows, as well as to the appended drawings. A more complete appreciation of the invention and many of the attendant advantages thereof will be readily obtained as the same becomes better understood by reference to the following Figures in conjunction with the detailed description below.

FIG. 1: Schematic overview of the foamy viruses replication cycle. DNA genomes are represented by bold lines, and RNA genomes are represented by curved lines. Characteristics specific to the FV life cycle are denoted by text and arrows.

FIG. 2: Schematic overview of the foamy viruses replication cycle after the mRNA mediated transduction. DNA genomes are represented by bold lines, and RNA genomes are represented by curved lines. Characteristics specific to the FV life cycle are denoted by text and arrows.

Figure 3:
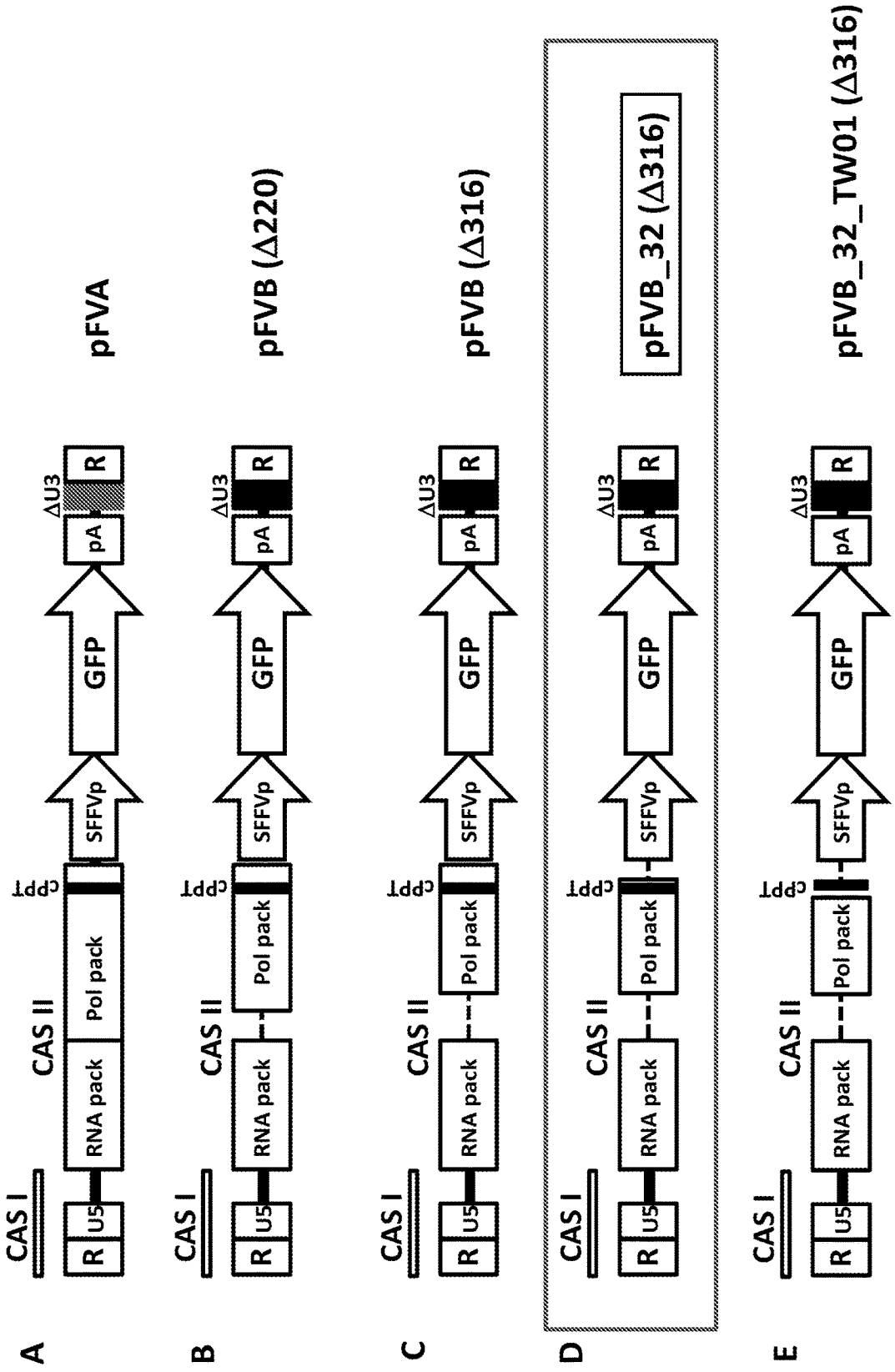

FIG. 3: Schematic representation of the foamy virus (FV) genomic RNA constructs which can be used in the present invention. D represents one of the preferred RNA construct, pFVB-32(Δ316). pFVB-32(Δ316) comprises a CAS I region including a foamy virus R region, FV U5 region, and the beginning of the Gag sequence; a Cas II region which comprises a RNA packaging sequence following by a Pol packaging sequence, including a cPPT sequence; the transgene under the control of the SFFV promoter, the bovine growth hormone (BGH) polyA, the foamy virus partial U3 sequence (Δ3) and finally the R region.

Table 1: Cytopulse program used to electroporate purified T-cells

DISCLOSURE OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Methods of Integrating a Transgene in the Genome of a Cell

Spumavirus vary from the orthoretrovirinae in a number of important ways. FV reverse transcribes their packaged RNA genome after capsid assembly in virus-producing cells. Furthermore, a nuclear reshuttling and reintegration of viral genomes in producer cells can occur as well as cell-to-cell transfer (Heinkelein, Pietschmann et al. 2000; Heinkelein, Rammling et al. 2003). Using this property, the inventors sought a virus system that efficiently and stably infects cells while avoiding the step of production of cell free supernatant. The invention relates to a method of integrating a transgene in host cell genome based on the intracellular retrotransposition of the foamy virus genome.

More particularly the invention relates to the introduction of at least one RNA comprising a sequence encoding FV gag protein, a sequence encoding a FV pol protein, and a foamy viral vector genome sequence comprising a transgene into a cell such that the trangene integrates into the host genome. In a particular said method optionally comprises the steps of culturing the cells and optionally selecting said cell in which said transgene has been integrated within the genome.

Gag protein is the major structural component of the viral particle. Gag functions are, however, not restricted to capsid formation; retroviral Gag proteins have numerous and very complex roles in the viral life cycle. Gag, (i) is the major component involved in intracellular trafficking processes; (ii) orchestrates viral assembly and disassembly; (iii) regulates viral gene expression; (iv) mediates correct encapsidation of Pol, the viral genome, and accessory proteins; (v) is involved in spatiotemporal regulation of the essential, viral, enzymatic reactions; and (vi) is essential for viral budding (Freed 1998). In particular embodiment, the sequence encoding Gag protein of the present invention is a foamy virus Gag sequence (Mullers 2013). In contrast to all other retroviruses, FV only express a Gag, and not a Gag-Pol fusion protein. The FV Gag can be as non limiting examples the prototypic Foamy Virus Pol (PFV) which was originally named human foamy virus (HFV) since it was isolated from a patient with nasopharyngeal carcinoma and was thought to be a human virus (SEQ ID NO: 4), The simian virus (e.g. SEQ ID NO: 5 to SEQ ID NO:7) (e.g. SFV of squirrel monkey, SFV of chimpanzees), the Equine FV (EFV)(SEQ ID NO: 8), bovine FV (BFV) (SEQ ID NO: 9), and feline FV (FFV) (SEQ ID NO: 10) Gag. The Gag RNA can encode a Gag precursor protein, in particular a 71 kDa precursor (p71$^{Gag}$) or FV Gag cleaved versions such as p68$^{Gag}$ and p3$^{Gag}$.

The Gag sequence according to the present invention can encode a functional variant of FV gag protein, which performs similar functions to achieve viral replication, and comprises similar functional domains. Examples of Gag functional domains can be the cytoplasmic targeting and retention signal (CTRS), coil-coil (C-C) domains, L-domain, YXXLGL motif, Glycine (G)-Arginine (R)-boxes. Functional variants of the polypeptide can be prepared by mutations in the polynucleotide which encodes the polypeptide. Such variants or functional variants include, for example, deletions from, or insertions or substitutions of, residues within the amino acid sequence. Any combination of deletion, insertion, and substitution may also be made to arrive at the final construct, provided that the final construct possesses the desired activity.

In a particular embodiment, the RNA(s) according to the present invention comprise sequence encoding Gag protein comprising the amino acid sequence selected from the group consisting of: SEQ ID NO: 3 to 10. The present invention relates to Gag protein comprising an amino acid sequence that has at least 70%, preferably at least 80%, more preferably at least 90%, 95% 97% or 99% sequence identity with an amino acid sequence selected from the group consisting of SEQ ID NO: 3 to 10. In more particular embodiment, RNA(s) comprise Gag sequence SEQ ID NO: 2. More particularly, the RNA according to the present invention comprises a nucleic acid sequence that has at least 60%, 70%, preferably at least 80%, more preferably at least 90%, 95% 97% or 99% sequence identity with a nucleic acid sequence selected from the group consisting of SEQ ID NO: 2.

The present invention relates to method comprising introducing into a cell at least one RNA comprising a sequence encoding a Pol protein. In particular, Pol protein can be a precursor protein comprising (i) a reverse transcriptase which converts the single-stranded viral RNA genome into double-strand DNA (dsDNA), (ii) an integrase which integrate the reverse-transcribed dsDNA into the cell genome, (iii) a protease, preferably an aspartyl protease which cleaves Gag and Pol domains for maturation and RNase H which degrades the RNA strand of an RNA-DNA duplex. The Pol protein of the present invention is preferably a FV Pol protein and particularly the precursor protein p127$^{pol}$ (Lee, Stenbak et al. 2013). FV pol precursor protein is autocatalytically processed into only two subunits, and Pol protein can refer to a larger FV pol protein (PFV p85$^{PR-RT-RN}$) with protease (PR), reverse transcriptase (RT) and RNaseH (RN) enzymatic activities and a smaller one (PFV p40IN) with integrase activity.

The FV Pol can be as non limiting examples the prototypic Foamy Virus Pol (PFV) (SEQ ID NO: 14), the simian FV Pol (e.g. SEQ ID NO: 15 to SEQ ID NO: 17) (e.g. SFV of squirrel monkey, SFV of chimpanzees, the Equine FV (EFV) (SEQ ID NO: 18), bovine FV (BFV)(SEQ ID NO: 19), and feline FV (FFV) (SEQ ID NO: 20) Pol.

The Pol protein according to the present invention can be a functional variant of FV Pol, which performs similar functions and comprises similar functional domains. Functional variants of the polypeptide can be prepared by mutations in the polynucleotide sequence which encodes the polypeptide. Such variants or functional variants include, for example, deletions from, or insertions or substitutions of, residues within the amino acid sequence. Any combination of deletion, insertion, and substitution may also be made to arrive at the final construct, provided that the final construct possesses the desired activity.

In a particular embodiment, the RNA(s) according to the present invention comprise sequence encoding Pol protein comprising the amino acid sequence selected from the group consisting of: SEQ ID NO: 13 to SEQ ID NO: 20. The present invention relates to Pol protein comprising an amino acid sequence that has at least 70%, preferably at least 80%, more preferably at least 90%, 95% 97% or 99% sequence identity with an amino acid sequence selected from the group consisting of SEQ ID NO: 13 to SEQ ID NO: 20. In more particular embodiment, RNA(s) comprise Pol sequence SEQ ID NO: 12. More particularly, the RNA according to the present invention comprises a nucleic acid sequence that has at least 60%, 70%, preferably at least 80%, more preferably at least 90%, 95% 97% or 99% sequence identity with a nucleic acid sequence selected from the group consisting of SEQ ID NO: 12.

The method of the present invention comprises introducing into the cell RNA(s) comprising foamy virus genomic sequence. Components of the foamy viral genome that are not necessary for efficient gene transfer can be removed (Heinkelein, Schmidt et al. 1998; Wiktorowicz, Peters et al. 2009; Lindemann and Rethwilm 2011). As non limiting examples, Foamy virus genomic sequence comprises FV cis-acting sequences (CAS) essential for efficient gene transfer. In particular, CAS are involved in RNA dimerization, and genome packaging, probably in reverse transcription and in the regulation of gene expression at the transcriptional or post-transcriptional level. FV cis-acting sequences can comprise at least one of three regions of the genome: CAS I, CAS II and CAS III regions. Generally, only CAS I and CAS II are necessary for efficient vector transgene transduction. CAS I comprises the primer binding site (PBS), R, U5 region and the beginning of gag. The initiation coding of gag can be mutated in order to avoid expression of a truncated gag peptide that could interfere with viral particle formation. CAS II is located in the 3' Pol region. CAS II is a bipartite element and an internal deletion seems to improve transfection efficiency. CAS II comprises at least one central poly-purine tract (PPT), a RNA packaging sequence and a proposed Pol encapsidation sequence. CAS III comprises about 40 nucleotides upstream of the 3'LTR, including the 3'PPT and the complete R region (Heinkelein, Dressler et al. 2002; Lindemann and Rethwilm 2011). For safety reasons, the 3'LTRs in FV genomic RNA preferably have large deletion in the U3 region encompassing viral promoter and enhancer elements. Examples of FV genomic RNA constructs suitable for the present invention are represented in FIG. 3 ((Heinkelein, Schmidt et al. 1998; Wiktorowicz, Peters et al. 2009; Lindemann and Rethwilm 2011).

The RNA(s) according to the present invention also comprise a transgene, generally inserted within the genomic viral sequence after CAS II region. In a preferred embodiment, this transgene is under the control of an heterologous promoter. In a preferred embodiment heterologous promoter can be a Spleen Focus-Forming Virus U3 (SFFV) promoter. Minimum FV genomic sequence are capable of packaging 11.2 kb of foreign DNA. As used herein, the term transgene means a nucleic acid sequence (encoding, e.g., one or more polypeptides), which is partly or entirely heterologous, i.e., foreign, to the host cell into which it is introduced, or, is homologous to an endogenous gene of the host cell into which it is introduced, but which is designed to be inserted, or is inserted, into the cell genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of the selected nucleic acid encoding polypeptide. As a non limiting example, said FV genomic sequence comprises: a FV R sequence (e.g. SEQ ID NO: 21), FV U5 sequence (e.g. SEQ ID NO: 22), FV CAS I sequence comprising a 5' fragment of Gag coding region and wherein the ATG codon region has been mutated to avoid expression of truncated gag peptide (e.g. SEQ ID NO: 23), FV CAS II sequences (SEQ ID NO: 24 and SEQ ID NO: 25) comprising central PPT (e.g. SEQ ID NO: 26), a promoter sequence (e.g. SFFV promoter sequence (SEQ ID NO: 27)) upstream to a transgene, optionally a 3'PPT sequence (SEQ ID NO: 29), a FV partial U3 sequence (e.g. SEQ ID NO: 28) and finally FV R sequence (e.g. SEQ ID NO: 21) (see FIG. 3 D).

In a particular embodiment, the method further comprises the introduction into the cell of RNA(s) comprising a sequence encoding Envelope (Env) protein. The envelope protein can be a FV Env precursor protein which comprises a signal peptide to target the protein to the rough endoplasmatic reticulum (also named leader peptide), a surface (SU) domain and a transmembrane (TM) domain (US2012/0141440). FV Env protein processing into LP (gp18LP), SU (gp80SU) and TM (gp48TM) subunits occurs along its transport to the cell surface and is mediated by furin or furin-like proteases. FV Env protein according to the present invention can be processed Env proteins. The FV Env can be as non limiting examples the prototypic Foamy Virus Env (PFV) (SEQ ID NO: 33), the simian FV Env (e.g. SEQ ID NO: 34 to SEQ ID NO: 36) (e.g. SFV of squirrel monkey, SFV of chimpanzees), the Equine FV (EFV) (SEQ ID NO: 37), bovine FV (BFV) (SEQ ID NO: 38), and feline FV (SEQ ID NO: 39) (FFV) Env.

The Env protein according to the present invention can be a functional variant of FV Env, which performs similar functions and comprises similar functional domains. Functional variants of the polypeptide can be prepared by mutations in the polynucleotide sequence which encodes the polypeptide. Such variants or functional variants include, for example, deletions from, or insertions or substitutions of, residues within the amino acid sequence. Any combination of deletion, insertion, and substitution may also be made to arrive at the final construct, provided that the final construct possesses the desired activity.

In a preferred embodiment, Envelope sequence encodes a mutated envelope protein which promotes the intracellular retro-transposition or cell-to-cell transfer phenomenons (Heinkelein, Pietschmann et al. 2000; Heinkelein, Rammling et al. 2003). In particular, the mutated envelope protein cannot generate infectious vector virus particle. Said mutation can be a substitution, a deletion, an insertion of at least one nucleotide, or combination thereof. As non limiting example, the Env protein can be a cleavage site mutant Env protein in which the gp130 Env precursor is not processed into the gp80 surface and gp48 transmembrane subunit (Heinkelein, Pietschmann et al. 2000) such that the fusion peptide cannot be exposed. Examples of such mutants are an Envelope protein which has a threonine instead of an arginine in position 571 in the SU-TM cleavage site (SEQ ID NO: 41 encoding SEQ ID NO: 42) or in which the basic residues preceding the SU-TM cleavage site are converted from $Arg_{568}$-Lys-Arg-Arg to $Ala_{568}$-Ala-Glu-Ala (Heinkelein, Rammling et al. 2003).

In a particular embodiment, the RNA according to the present invention comprises a sequence encoding Env protein comprising the amino acid sequence selected from the group consisting of: SEQ ID NO: 32 to SEQ ID NO: 39 and SEQ ID NO: 42. The present invention relates to Env protein comprising an amino acid sequence that has at least 70%, preferably at least 80%, more preferably at least 90%, 95% 97% or 99% sequence identity with an amino acid sequence selected from the group consisting of SEQ ID NO: 32 to SEQ ID NO: 39 and SEQ ID NO: 42. In more particular embodiment, Env sequence is selected from the group consisting of: SEQ ID NO: 31 and SEQ ID NO: 41. More particularly, the RNA according to the present invention comprises a nucleic acid sequence that has at least 60%, 70%, preferably at least 80%, more preferably at least 90%, 95% 97% or 99% sequence identity with a nucleic acid sequence selected from the group consisting of SEQ ID NO: 31 and SEQ ID NO: 41.

In particular embodiment, the different sequences encoding FV components are present in different RNA molecules. In a preferred embodiment, said method comprises the introduction into a cell of a first RNA comprising a sequence encoding FV Gag protein, a second RNA comprising a sequence encoding FV Pol protein, a third RNA comprising a sequence encoding the FV genomic sequence and the transgene. In a more preferred embodiment, said method comprises the introduction into a cell of a fourth RNA comprising a sequence encoding an Env protein, preferably, Env fusion deficient mutant protein. In another embodiment, the different FV components sequences can be included in one RNA molecule. Said RNA molecule can comprise a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al., J. of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA. As non-limiting example, in the present invention, 2A peptides have been used to express into the cell the different FV components.

Those skilled in the art will recognize that, in view of the degeneracy of the genetic code, considerable sequence variation is possible among these RNA molecules. Preferably, the RNA sequences of the present invention are codon-optimized for expression in mammalian cells, preferably for expression in human cells of foamy virus components and functional variants thereof. Codon-optimization refers to the exchange in a sequence of interest of codons that are generally rare in highly expressed genes of a given species by codons that are generally frequent in highly expressed genes of such species, such codons encoding the amino acids as the codons that are being exchanged. Thus, the RNA according to the present invention comprises a nucleic acid sequence that has at least 60%, 70%, preferably at least 80%, more preferably at least 90%, 95% 97% or 99% sequence identity with a nucleic acid sequence selected from the group consisting of SEQ ID NO: 2, SEQ ID NO: 12, SEQ ID NO: 21 to 29, SEQ ID NO: 31, SEQ ID NO: 41 and SEQ ID NO: 44.

In a particular embodiment, RNA according to the present invention can comprise modified nucleotides. As used in the context of the present invention, the term "modified nucleotide" refers to a nucleotide that differs in structure from the standard or "unmodified" nucleotides 2'-deoxy-adenosine, 2'-deoxy-thymidine, 2'-deoxy-cytidine and 2'-deoxy-guanosine, and that is capable of pairing with an unmodified nucleotide or a modified nucleotide. Non limiting examples of modifications on the sugar or base moieties of a nucleotide include the addition (or removal) of acetyl groups, amino groups, carboxyl groups, carboxymethyl groups, hydroxyl groups, methyl groups, phosphoryl groups and thiol groups, as well as the substitution of the carbon and nitrogen atoms of the bases with other atoms (e.g., 7-deaza purines). Modified nucleotide also include dideoxy nucleotides, 2'-O-methyl nucleotides, locked nucleic acids (LNA), peptides nucleic acids (PNA), and morpholinos. The nucleotides of RNA may be linked by phosphodiester, phosphorodiamate bonds, or combinations thereof. Such modified nucleotides are useful for instance to introduce markers, tag, epitopes or reactive groups into the genome. The RNA according to the present invention can also comprise one or more phosphorothioatephosphodiester bonds between terminal base pairs to protect the linear donor polynucleotide from exonucleolytic degradation. These bonds may be in two or more positions at the 5' and/or 3' ends of the molecule and may be added during isolation or synthesis using standard methodology. See, e.g. (Ciafre, Rinaldi et al. 1995). The RNA can also be an RNA cap wherein a modified guanine nucleotide has been added to the 5' end of the messenger RNA shortly after the start transcription. The 5' cap consists of a terminal group which is linked to the first transcribed nucleotide. Said RNA may comprise phosphodiester linkages, phosphorothioate linkages, phosphoramidite linkages, phosphorodiamidate linkages, or combinations thereof. In a particular embodiment, the RNA can also comprise a 3'UTR or 5'UTR region. Preferably RNA comprises at least one 3'UTR or 5'UTR derived from human globin, preferably alpha or beta human globin. In another particular embodiment, RNA according to the present invention can comprise a poly(A). A poly(A) is a series of adenosines attached by polyadenylation to the mRNA. The poly A can be between 50 and 5000, preferably greater than 64, more preferably greater than 100, more preferably greater than 300 or 400. Poly(A) sequences can be modified chemically or enzymatically to modulate mRNA functionality such as localization, stability or efficiency of translation.

The RNA according to the present invention may comprise a sequence encoding a polypeptide (e.g., cDNA), an enhancer sequence, marker genes, cleavage enzyme recognition site, epitope tags. Marker genes can be sequences encoding protein that mediate antibiotic resistance, sequence encoding colored, fluorescent or luminescent proteins. Preferably the markers genes are added in the viral genomic RNA to allow the selection of cells having a transgene integrated into cell genome.

The RNA according to the present invention can be transcribed in vitro. Methods for producing the in vitro transcribed RNA according to the present invention are well-known in the art. As non limiting examples, RNA can be produced by in vitro transcription using vector or PCR-generated template using appropriate primers and RNA polymerase. In another embodiment, said RNA can be a synthetic RNA, particularly synthesized through known methods of oligonucleotide synthesis.

Delivery Methods

The different methods described above involve introducing RNA into a cell. As non-limiting example, said RNA can be introduced as RNA encoded by one or as different RNA molecules. Different FV component sequences can be included in one RNA molecule which comprises a nucleic acid sequence encoding ribosomal skip sequence such as a sequence encoding a 2A peptide. Said RNA can also encode a selection marker which provides for identification and/or selection of cells that received said RNA.

Polypeptides are synthesized in situ in the cell as a result of the introduction of RNAs encoding said polypeptides into the cell. Methods for introducing a RNA construct into cells are known in the art and including as non limiting examples microinjection, electroporation, sonoporation, particle bombardment, calcium phosphate-mediated transfection cationic transfection, liposome transfection, dendrimer transfection, heat shock transfection, nucleofection transfection, magnetofection, lipofection, impalefection, optical transfection, proprietary agent-enhanced uptake of nucleic acids and delivery via liposomes, immunoliposomes, virosomes or artificial virions.

In a more preferred embodiment of the invention, RNA according to the present invention can be introduced directly into the cells, for example by electroporation. The inventors determined the optimal condition for RNA electroporation in T-cell.

The inventor used the cytoPulse technology which allows, by the use of pulsed electric fields, to transiently permeabilize living cells for delivery of material into the cells. The technology, based on the use of PulseAgile (BTX Havard Apparatus, 84 October Hill Road, Holliston, Mass. 01746, USA) electroporation waveforms grants the precise control of pulse duration, intensity as well as the interval between pulses (U.S. Pat. No. 6,010,613 and International PCT application WO2004083379). All these parameters can be modified in order to reach the best conditions for high transfection efficiency with minimal mortality. Basically, the first high electric field pulses allow pore formation, while subsequent lower electric field pulses allow moving the polynucleotide into the cell. In one aspect of the present invention, the inventors describe the steps that led to achievement of >95% transfection efficiency of mRNA in T cells, and the use of the electroporation protocol to transiently express different kind of proteins in T cells. The steps of this electroporation method comprise applying to T cell an agile pulse sequence comprising:

(a) one electrical pulse with a voltage range from 2250 to 3000 V per centimeter, with a pulse width preferably less than 1 ms, more preferably of about 0.1 ms;

(b) one electrical pulse with a voltage range from 2250 to 3000 V with a pulse width from 10 to 500 ms, preferably from 50 to 150, and more preferably of about 100 ms and a pulse interval of 100 ms between the electrical pulse of step (b) and the first electrical pulse of step (c); and (c) at least one to several electrical pulses, preferably between 2 and 5, more preferably 4 pulses with a voltage between 250 and 400 V, preferably of about 325 V with a pulse width of less than 1 ms, preferably of about 0.2 ms and a pulse interval of more than 1 ms, preferably of about 2 ms between each of the electrical pulses.

The pulse interval is generally from 0.2 to 10 ms between the electrical pulses of step (a) and (b), and from 50 to 150, preferably of about a 100 ms, between the electrical pulse of step (b) and the first electrical pulse of step (c).

In particular embodiment, the method of transforming T cell comprising contacting said T cell with RNA and applying to T cell an agile pulse sequence consisting of:

(a) one electrical pulse with a voltage of 2250, 2300, 2350, 2400, 2450, 2500, 2550, 2400, 2450, 2500, 2600, 2700, 2800, 2900 or 3000V per centimeter, a pulse width of about 0.1 ms and a pulse interval of 0.2, 0.5, 1, 2, 3, 4, 5, 6, 7, 8, 9 or 10 ms between the electrical pulses of step (a) and (b);

(b) one electrical pulse with a voltage range from 2250, of 2250, 2300, 2350, 2400, 2450, 2500, 2550, 2400, 2450, 2500, 2600, 2700, 2800, 2900 or 3000V with a pulse width of about 100 ms and a pulse interval of about 100 ms between the electrical pulse of step (b) and the first electrical pulse of step (c); and (c) At least one to several electrical pulses, preferably between 2 and 5, more preferably 4 electrical pulses with a voltage between 300 and 400 V, and preferably of about 325 V with a pulse width from 0.1 to 1 ms, preferably of about 0.2 ms and a pulse interval from 1.5 to 5 ms, preferably of about 2 ms between each of the electrical pulses.

Any values included in the value range described above are disclosed in the present application. Electroporation medium can be any suitable medium known in the art. Preferably, the electroporation medium has conductivity in a range spanning 0.01 to 1.0 milliSiemens. In particular embodiments, as non limiting examples, said RNA encodes at least one component of foamy virus.

Isolated Cells

A variety of cells are suitable for use in the method according to the invention. Cells can be any prokaryotic or eukaryotic living cells, cell lines derived from these organisms for in vitro cultures, primary cells from animal or plant origin.

This method is particularly suitable for hematopoietic cells, particularly immune cells. Said immune cell refers to a cell of hematopoietic origin functionally involved in the initiation and/or execution of innate and/or adaptative immune response. Said isolated cell according to the present invention can be a stem cell. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Said isolated cell can also be a dendritic cell, killer dendritic cell, mast cell, a Natural Killer (NK)-cell, NKT cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes.

A particular aspect of the present invention relates to an isolated cell as previously described modified by one of the method according to the invention. Typically, said isolated cell comprises RNA(s) comprising FV Gag, FV Pol and FV genomic sequences. In a preferred embodiment, said cell according to the invention comprises at least one transgene integrated into the genome of the cell. The resulting modified cell can be used as a cell line for a diversity of applications ranging from bioproduction, animal transgenesis (by using for instance stem cells), plant transgenesis (by using for instance protoplasts), to cell therapy (by using for instance T-cells). The present invention thus expands to the cells lines, transgenic animals or plants resulting from the transformation of such cells according to the invention, as well as to the therapies that may be applied therefrom.

Therapeutic Applications

The method of genetic modification disclosed herein can have a variety of applications. In one embodiment, the method can be used for clinical or therapeutic applications. The method can be used to drive expression of a transgene in order to repair or correct disease-causing genes, as for example a single nucleotide change in sickle-cell disease. The method can also be used for complementation of a disease-causing gene. By complementation, it is meant the interaction between two sets of cellular genes within a cell such that the cell can function even though each set of genes carries a mutated, nonfunctional gene. The method can be used to correct splice junction mutations, deletions, insertions, and the like in other genes or chromosomal sequences that play a role in a particular disease or disease state.

From the above, the isolated cell obtainable by the method according to the invention can be used as a medicament, especially for modulating, activating or inhibiting gene expression. Foamy RNA according to the present invention can be used for the treatment of a genetic disease to correct a mutation at a specific locus or to inactivate a gene the expression of which is deleterious. Such RNA can also be used to genetically modify iPS or primary cells, for instance T-cells, in view of injecting such cells into a patient for treating a disease or infection. Such cell therapy schemes are more particularly developed for treating cancer, viral infection such as caused by CMV or HIV or self-immune diseases.

The present invention also encompasses transgenic animals or plants which comprise modified targeted genetic sequence of interest by the methods described above.

Kit

In another aspect, the invention relates to a kit for the expression of foamy virus RNA in cells. The kit can comprise one or a plurality of RNA(s) comprising sequences encoding the different FV components as described in the present disclosure. In a particular embodiment, the kit can comprise a first RNA comprising sequence encoding FV Gag protein, a second RNA comprising sequence encoding FV Pol protein, a third RNA comprising FV genomic RNA and optionally a fourth RNA comprising sequence encoding FV Env protein, preferably fusion deficient Env protein. This RNA can be under a suitable form for transfection and expression in the selected host cell. In another particular embodiment, the kit can comprise expression vector(s) used to express the RNA(s).

As previously referred to, the kit according to the invention can be used for therapeutic purposes, in particular for treating genetic diseases.

DEFINITIONS

In the description above, a number of terms are used extensively. The following definitions are provided to facilitate understanding of the present embodiments.

As used herein, "a" or "an" may mean one or more than one.

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, g is guanine and u is uracil. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

As used herein, "nucleic acid" or "polynucleotide" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

"Identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting.

A variety of cells are suitable for use in the method according to the invention. Cells can be any prokaryotic or eukaryotic living cells, cell lines derived from these organisms for in vitro cultures, primary cells from animal or plant origin.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines. These cells thus represent a more valuable model to the in vivo state they refer to.

In the frame of the present invention, "eukaryotic cells" refer to a fungal, plant, algal or animal cell or a cell line derived from the organisms listed below and established for in vitro culture. More preferably, the fungus is of the genus *Aspergillus, Penicillium, Acremonium, Trichoderma, Chrysoporium, Mortierella, Kluyveromyces* or *Pichia*; More preferably, the fungus is of the species *Aspergillus niger, Aspergillus nidulans, Aspergillus oryzae, Aspergillus terreus, Penicillium chrysogenum, Penicillium citrinum, Acremonium Chrysogenum, Trichoderma reesei, Mortierella alpine, Chrysosporium lucknowense, Kluyveromyces lactis, Pichia pastoris* or *Pichia ciferrii*. More preferably the plant is of the genus *Arabidopsis, Nicotiana, Solanum, lactuca, Brassica, Oryza, Asparagus, Pisum, Medicago, Zea, Hordeum, Secale, Triticum, Capsicum, Cucumis, Cucurbita, Citrullis, Citrus, Sorghum*; More preferably, the plant is of the species *Arabidospis thaliana, Nicotiana tabaccum, Solanum lycopersicum, Solanum tuberosum, Solanum melongena, Solanum esculentum, Lactuca saliva, Brassica napus, Brassica oleracea, Brassica rapa, Oryza glaberrima, Oryza sativa, Asparagus officinalis, Pisumsativum, Medicago sativa, zea mays, Hordeum vulgare, Secale cereal, Triticuma estivum, Triticum durum, Capsicum sativus, Cucurbitapepo, Citrullus lanatus, Cucumis melo, Citrus aurantifolia, Citrus maxima, Citrus medico, Citrus reticulata*. More preferably the animal cell is of the genus *Homo, Rattus, Mus, Sus, Bos, Danio, Canis, Felis, Equus, Salmo, Oncorhynchus, Gallus, Meleagris, Drosophila, Caenorhabditis*; more preferably, the animal cell is of the species *Homo sapiens, Rattus norvegicus, Mus musculus, Sus scrofa, Bos taurus, Danio rerio, Canis lupus, Felis catus, Equus caballus, Salmo solar, Oncorhynchus mykiss, Gallus gallus, Meleagris gallopavo, Drosophila melanogaster, Caenorhabditis elegans*.

In the present invention, the cell is preferably a plant cell, a mammalian cell, a fish cell, an insect cell or cell lines derived from these organisms for in vitro cultures or primary cells taken directly from living tissue and established for in vitro culture. As non limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells. Are also encompassed in the scope of the present invention stem cells and induced Pluripotent Stem cells (iPS).

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e.g. adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, Spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as non limiting example, that are able to integrate the genome of a target cell. At the opposite by "non integrative lentiviral vectors (or NILV)" is meant efficient gene delivery vectors that do not integrate the genome of a target cell through the action of the virus integrate.

Delivery vectors and vectors can be associated or combined with any cellular permeabilization techniques such as sonoporation or electroporation or derivatives of these techniques.

EXAMPLE

Each foamy virus component: Gag (SEQ ID NO: 1), Pol (SEQ ID NO: 11), FV genomic sequence with GFP transgene (SEQ ID NO: 43), Env (SEQ ID NO: 30) and fusion deficient Env sequences (EnvEM20, SEQ ID NO: 40) was subcloned by restriction enzyme digestion into a mammalian expression vector under the control of the T7 promoter. mRNA encoding foamy virus components was synthesized from each plasmid carrying the coding sequences downstream from the T7 promoter.

T lymphocytes isolated from peripheral blood and preactivated with anti-CD3/CD28 activator beads (Life technologies) were resuspended in cytoporation buffer T and electroporated using the cytopulse program described in table 1 with at least 10 µg of mRNAs encoding FV gag protein (SEQ ID NO: 2 encoding SEQ ID NO: 3), FV Pol protein (SEQ ID NO: 12 encoding SEQ ID NO: 13) and FV genomic RNA comprising eGFP transgene (SEQ ID NO: 44 encoding GFP protein (SEQ ID NO: 45)). In certain conditions, T lymphocytes were also transfected with FV Env RNA (SEQ ID NO: 30 encoding SEQ ID NO: 32) or FV fusion deficient Env RNA (SEQ ID NO: 41 encoding SEQ ID NO: 42) (BTX-Harvard apparatus).

TABLE 1

Cytopulse program used to electroporate purified T-cells.

| Cyto-pulse program | Group 1 | | | | Group 2 | | | | Group 3 | | | |
|---|---|---|---|---|---|---|---|---|---|---|---|---|
| | Pulse | V | duration (ms) | Interval (ms) | Pulse | V | duration (ms) | Interval (ms) | Pulse | V | duration (ms) | Interval (ms) |
| 3 | 1 | 1200 | 0.1 | 0.2 | 1 | 1200 | 0.1 | 100 | 4 | 130 | 0.2 | 2 |

Several days post electroporation, GFP expression was analyzed by flow cytometry on transfected cells to assess GFP transgene expression within the cell.

REFERENCES

Ciafre, S. A., M. Rinaldi, et al. (1995). "Stability and functional effectiveness of phosphorothioate modified duplex DNA and synthetic 'mini-genes'." *Nucleic Acids Res* 23(20): 4134-42.

Freed, E. O. (1998). "HIV-1 gag proteins: diverse functions in the virus life cycle." *Virology* 251(1): 1-15.

Heinkelein, M., M. Dressler, et al. (2002). "Improved primate foamy virus vectors and packaging constructs." *J Virol* 76(8): 3774-83.

Heinkelein, M., T. Pietschmann, et al. (2000). "Efficient intracellular retrotransposition of an exogenous primate retrovirus genome." *Embo J* 19(13): 3436-45.

Heinkelein, M., M. Rammling, et al. (2003). "Retrotransposition and cell-to-cell transfer of foamy viruses." *J Virol* 77(21): 11855-8.

Heinkelein, M., M. Schmidt, et al. (1998). "Characterization of a cis-acting sequence in the Pol region required to transfer human foamy virus vectors." *J Virol* 72(8): 6307-14.

Lee, E. G., C. R. Stenbak, et al. (2013). "Foamy virus assembly with emphasis on pol encapsidation." *Viruses* 5(3): 886-900.

Lindemann, D. and A. Rethwilm (2011). "Foamy virus biology and its application for vector development." *Viruses* 3(5): 561-85.

Mullers, E. (2013). "The foamy virus Gag proteins: what makes them different?" *Viruses* 5(4): 1023-41.

Pietschmann, T., H. Zentgraf, et al. (2000). "An evolutionarily conserved positively charged amino acid in the putative membrane-spanning domain of the foamy virus envelope protein controls fusion activity." *J Virol* 74(10): 4474-82.

Saib, A. (2003). "Non-primate foamy viruses." *Curr Top Microbiol Immunol* 277: 197-211.

Switzer, W. M., M. Salemi, et al. (2005). "Ancient co-speciation of simian foamy viruses and primates." *Nature* 434(7031): 376-80.

Wiktorowicz, T., K. Peters, et al. (2009). "Generation of an improved foamy virus vector by dissection of cis-acting sequences." *J Gen Virol* 90(Pt 2): 481-7.

The invention claimed is:

1. A method comprising:
    (a) providing at least one RNA comprising: (i) a sequence encoding foamy virus Gag protein, (ii) a sequence encoding foamy virus Pol protein; (iii) a Foamy Virus genomic sequence and a transgene; and
    (b) introducing said RNA into a cell by electroporation, such that the transgene is integrated within the genome of the electroporated cell.

2. The method of claim 1 further comprising:
    (c) selecting a cell in which said transgene has been integrated within the genome.

3. The method of claim 1, wherein the Pol protein comprises at least 80% sequence identity with the amino acid sequence of SEQ ID NO: 13.

4. The method of claim 1, wherein the Gag protein comprises at least 80% sequence identity with the amino acid sequence of SEQ ID NO: 3.

5. The method of claim 1, further comprising introducing an RNA comprising a sequence encoding a foamy virus envelope protein.

6. The method of claim 5, wherein said envelope protein is fusion deficient.

7. The method of claim 6, wherein said envelope protein comprises a threonine instead of an arginine at amino acid position 571.

8. The method of claim 5, wherein said envelope protein comprises at least 80% sequence identity with the amino acid sequence of SEQ ID NO: 39.

9. The method of claim 1, wherein said cell is a T cell.

10. The method of claim 2, further comprising administering said cell to a subject.

11. The method of claim 10, wherein said cell is a T cell.

* * * * *